United States Patent
Kaang et al.

(10) Patent No.: US 11,879,895 B2
(45) Date of Patent: Jan. 23, 2024

(54) INTERCELLULAR PROXIMITY LABELING USING EGRASP

(71) Applicant: Seoul National University R&DB Foundation, Seoul (KR)

(72) Inventors: Bong-Kiun Kaang, Seoul (KR); Jun Hyeok Choi, Yongin-si (KR); Ji-il Kim, Seoul (KR); Dong Ii Choi, Seoul (KR); Su-Eon Sim, Pohang-si (KR)

(73) Assignee: SEOUL NATIONAL UNIVERSITY R&DB FOUNDATION, Seoul (KR)

(*) Notice: Subject to any disclaimer, the term of this patent is extended or adjusted under 35 U.S.C. 154(b) by 395 days.

(21) Appl. No.: 17/048,730

(22) PCT Filed: Apr. 25, 2019

(86) PCT No.: PCT/KR2019/005026
§ 371 (c)(1),
(2) Date: Oct. 19, 2020

(87) PCT Pub. No.: WO2019/209056
PCT Pub. Date: Oct. 31, 2019

(65) Prior Publication Data
US 2021/0164986 A1 Jun. 3, 2021

(30) Foreign Application Priority Data
Apr. 26, 2018 (KR) .................. 10-2018-0048458

(51) Int. Cl.
*G01N 33/58* (2006.01)
*C07K 14/705* (2006.01)
*G01N 33/553* (2006.01)
*G01N 33/569* (2006.01)

(52) U.S. Cl.
CPC ......... *G01N 33/582* (2013.01); *C07K 14/705* (2013.01); *G01N 33/553* (2013.01); *G01N 33/569* (2013.01)

(58) Field of Classification Search
None
See application file for complete search history.

(56) References Cited

U.S. PATENT DOCUMENTS

2010/0173307 A1 7/2010 Lin et al.
2013/0058871 A1 3/2013 Kim

FOREIGN PATENT DOCUMENTS

JP 2007-535316 12/2007

OTHER PUBLICATIONS

Pisabarro et al. "Rational design of specific high-affinity peptide ligands for the Abl-SH3 domain." Biochemistry vol. 35,33 (1996): 10634-40. (Year: 1996).*

(Continued)

*Primary Examiner* — Bao-Thuy L Nguyen
*Assistant Examiner* — Alexander Alexandrovic Volkov
(74) *Attorney, Agent, or Firm* — LEX IP MEISTER, PLLC

(57) ABSTRACT

The present disclosure relates to an intercellular proximity labeling technique. According to an embodiment of the present disclosure, intercellular proximities can be distinguished by cell types, in particular, synapses of nerve cells can be distinguished by types.

9 Claims, 45 Drawing Sheets
Specification includes a Sequence Listing.

(56) References Cited

OTHER PUBLICATIONS

Morell et al. "Detection of transient protein-protein interactions by bimolecular fluorescence complementation: the Abl-SH3 case." Proteomics vol. 7,7 (2007): 1023-36. (Year: 2007).*

Tsetsenis et al. "Direct visualization of trans-synaptic neurexin-neuroligin interactions during synapse formation." The Journal of neuroscience : the official journal of the Society for Neuroscience vol. 34,45 (2014): 15083-96. (Year: 2014).*

Haryadi et al. "Optimization of heavy chain and light chain signal peptides for high level expression of therapeutic antibodies in CHO cells." PLoS One. Feb. 23, 2015;10(2):e0116878. (Year: 2015).*

Macpherson et al. "Dynamic labelling of neural connections in multiple colours by trans-synaptic fluorescence complementation." Nat Commun 6, 10024 (2015) (Year: 2015).*

Lee et al. "Advanced Fluorescence Protein-Based Synapse-Detectors." Frontiers in synaptic neuroscience vol. 8 16. Jun. 30, 2016. (Year: 2016).*

KIPO, A PCT Search Report & Written Opinion of PCT/KR2019/005026 dated Aug. 9, 2019.

Hojin Lee et al., "Advanced Fluorescence Protein-Based Synapse-Detectors", Frontiers in Synaptic Neuroscience, Jun. 30, 2016, vol. 8, No. 16, pp. 1-12.

Montse Morell et al., "Detection of transient protein-protein interactions by bimolecular fluorescence complementation: The Abl-SH3 case", Proteomics. 2007, vol. 7, pp. 1023-1036.

Wayne S. Sossin, "Memory Synapses Are Defined by Distinct Molecular Complexes: A Proposal", 4. Frontiers in Synaptic Neuroscience. Apr. 11, 2018, vol. 10, No. 5, pp. 1-14.

Yiming Li et al., "CRASP: CFP reconstitution across synaptic partners", Biochemical and Biophysical Research Communications 469 (2016) 352-356.

Ji-il Kim, "Studies on synaptic changes among engram cells after memory formation", Ph.D. thesis. School of Biological Sciences. The Graduate School of Seoul National University. Apr. 18, 2019.

Jun-Hyeok Choi et al., "Interregional synaptic maps among engram cells underlie memory formation", Science, Apr. 27, 2018, vol. 360, pp. 430-435.

Evan H. Feinberg et al., "GFP Reconstitution Across Synaptic Partners (GRASP) Defines Cell Contacts and Synapses in Living Nervous Systems", Neuron 57, 353-363, Feb. 7, 2008. DOI 10.1016/j.neuron.2007.11.030.

Ahmed A. Heikal et al., "Molecular spectroscopy and dynamics of intrinsically fluorescent proteins: Coral red (dsRed) and yellow (Citrine)", PNAS, vol. 97, No. 22, pp. 11996-12001, Oct. 24, 2000.

Takashi Kawashima et al., "A new era for functional labeling of neurons: activity-dependent promoters have come of age", Frontiers in Neural Circuits, vol. 8, article 37, Apr. 2014.

Karen P. Scott et al., "The green fluorescent protein as a visible marker for lactic acid bacteria in complex ecosystems", FEMS Microbiology Ecology 26 (1998) 219^230.

* cited by examiner

[Fig. 1a]
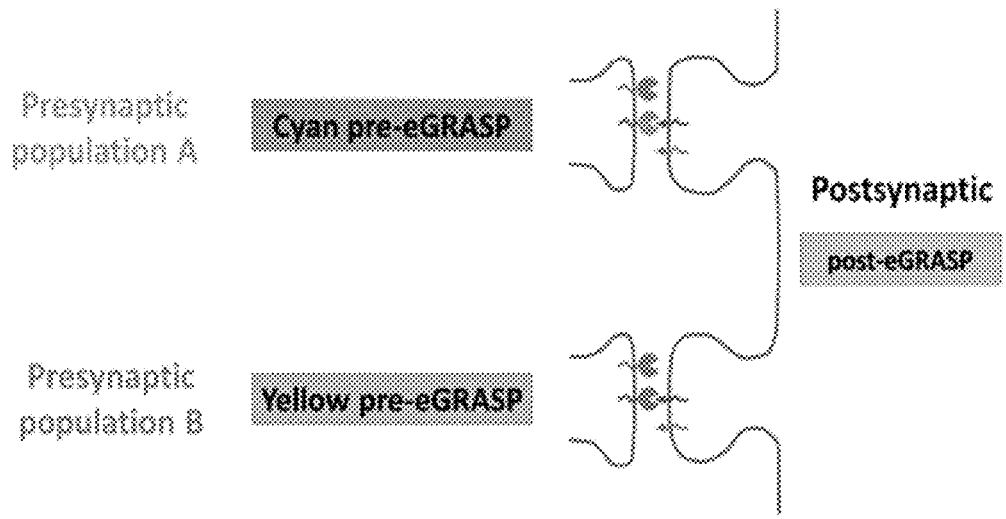

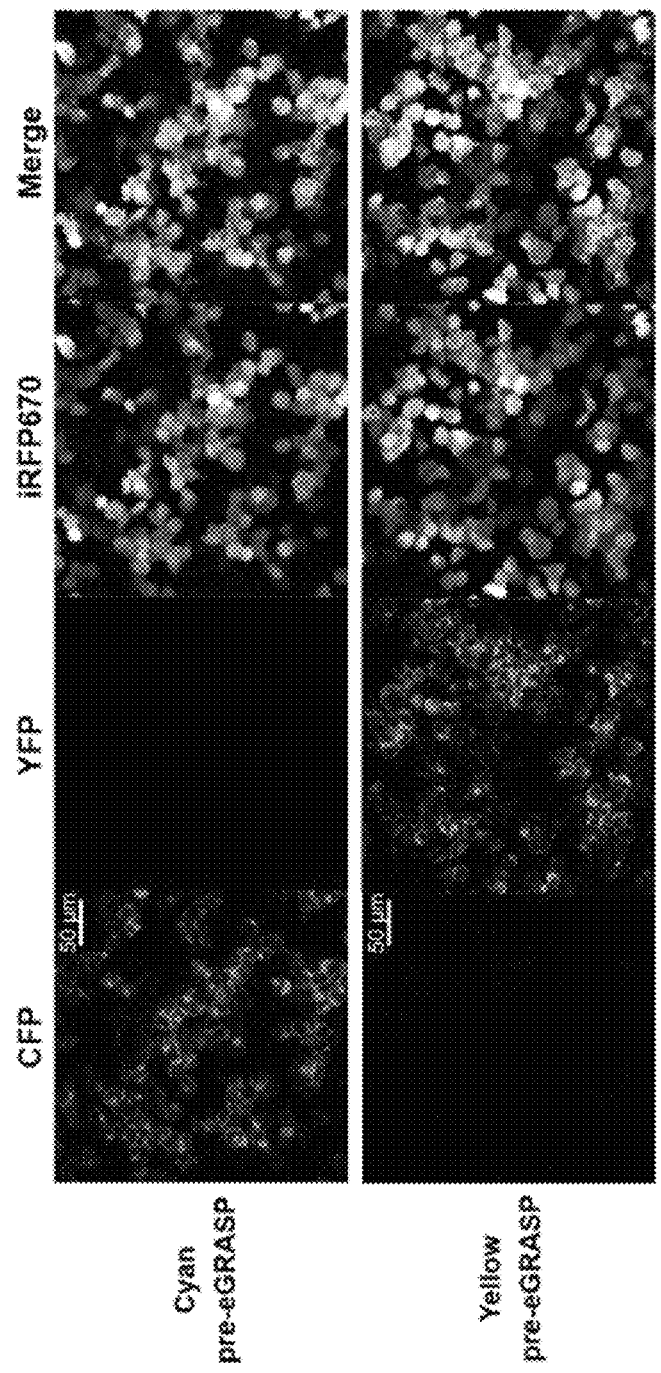
[Fig. 1b]

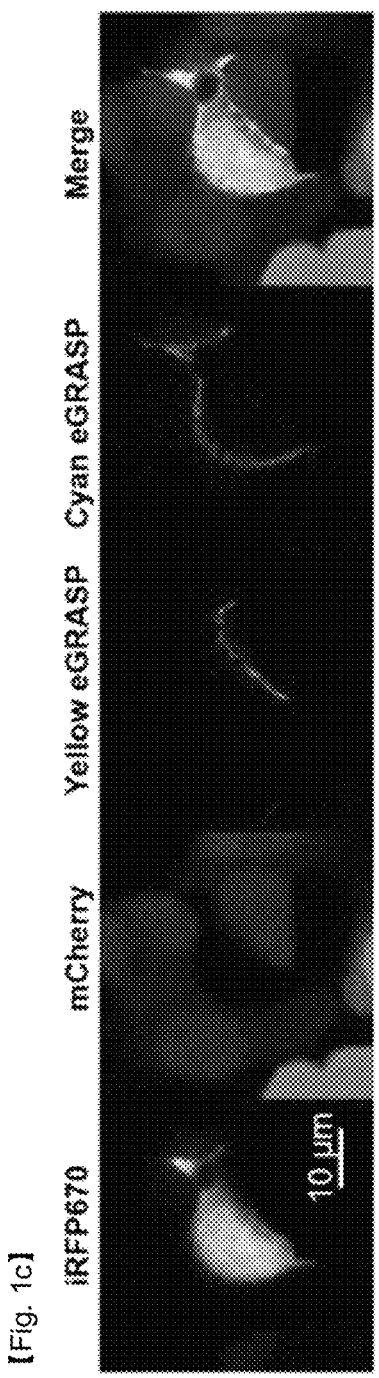
[Fig. 1c]

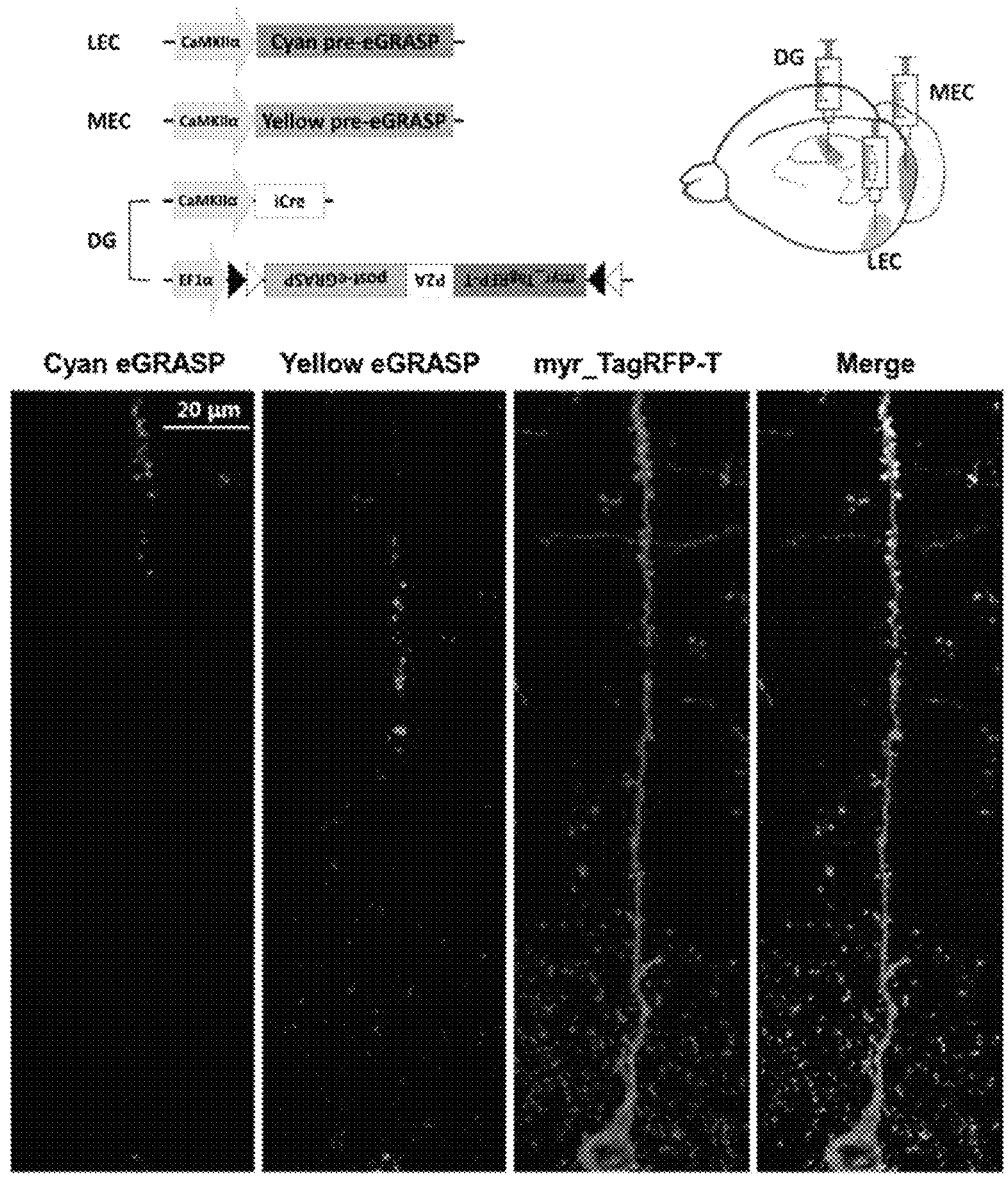

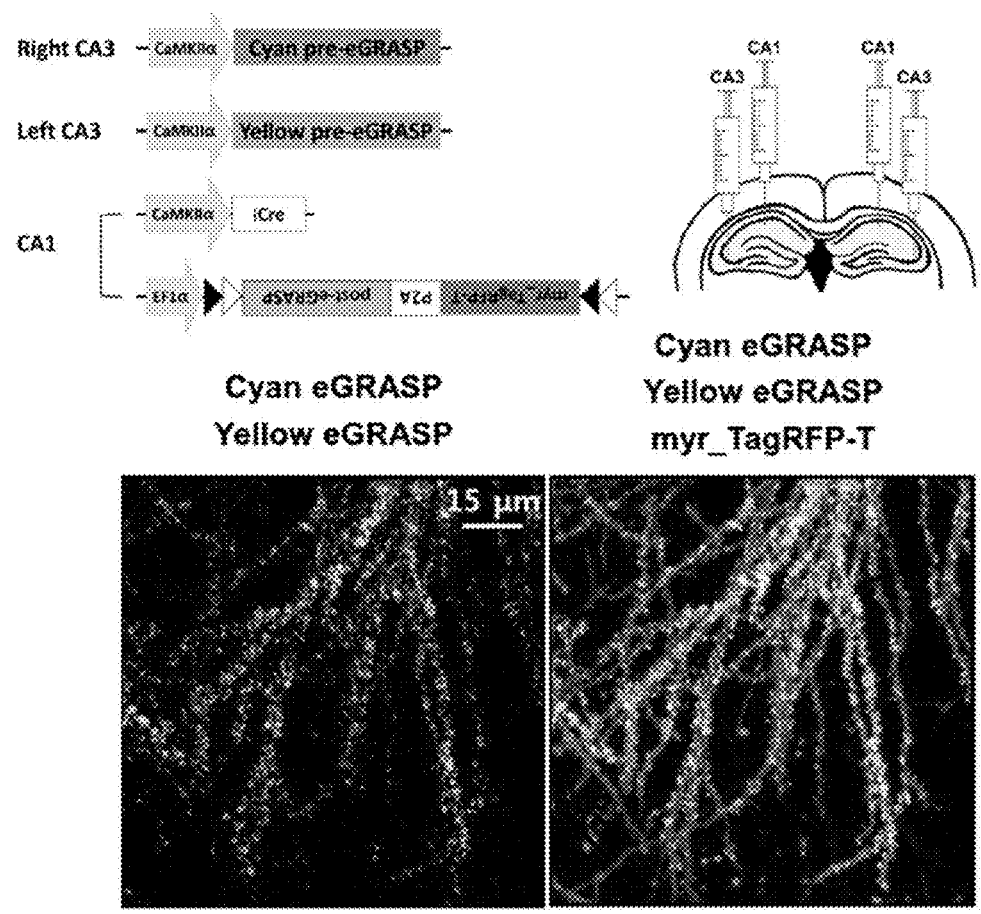

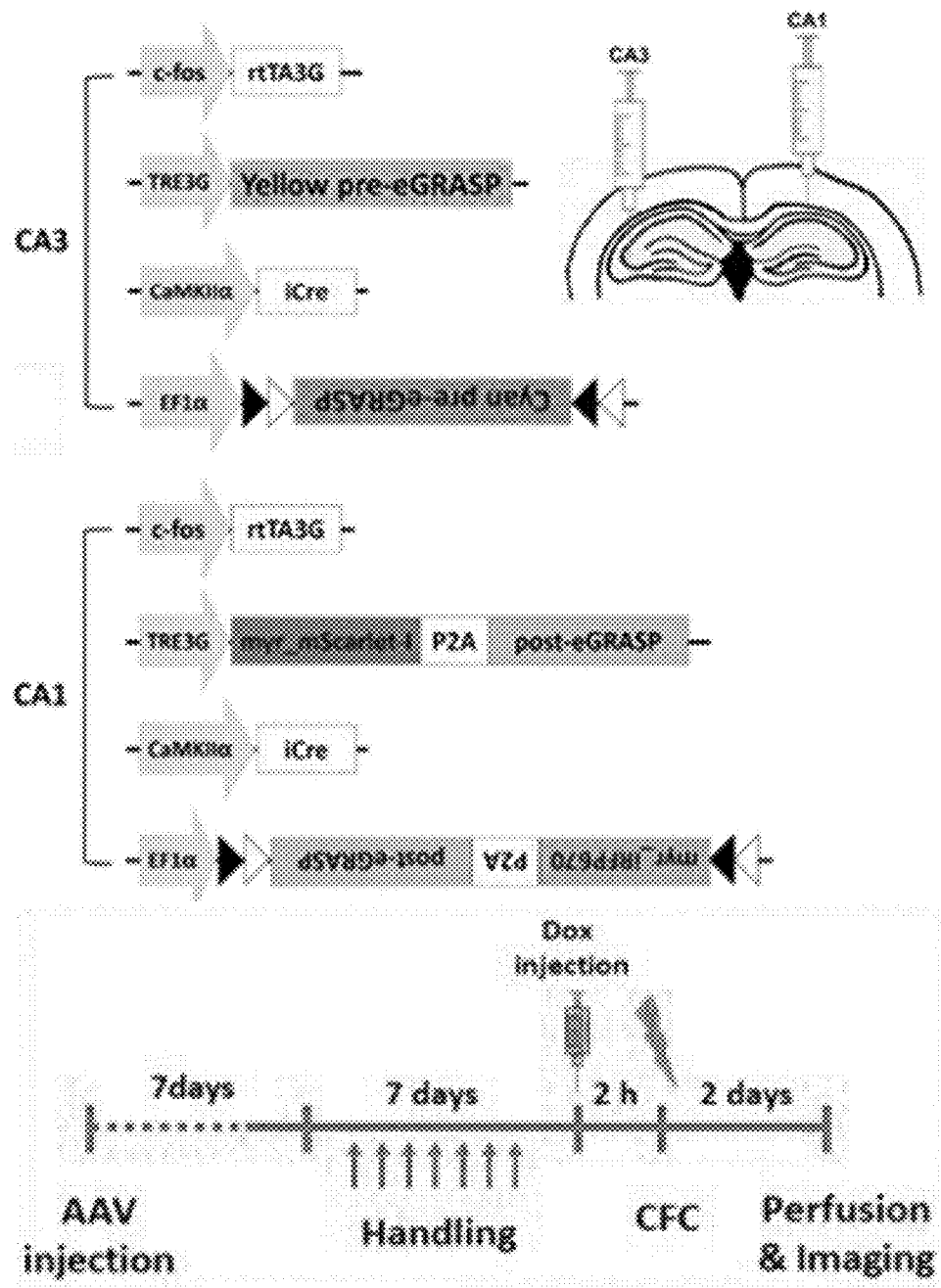
[Fig. 2a]

[Fig. 2b]
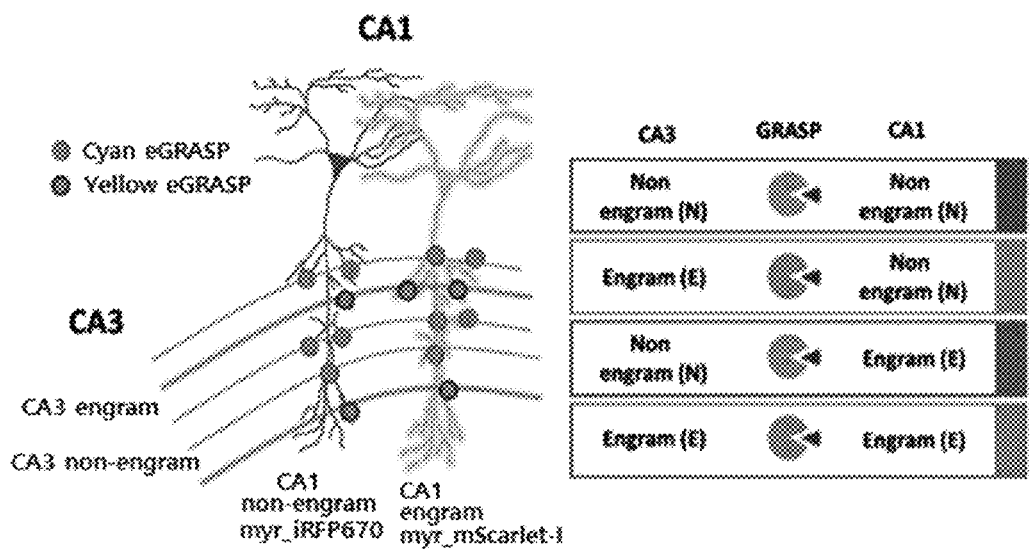
[Fig. 2c]
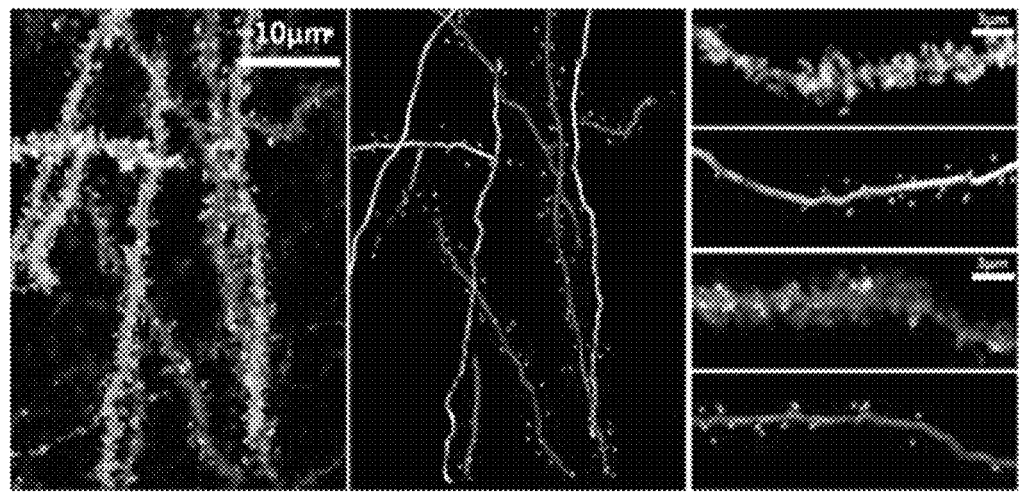

[Fig. 2d]
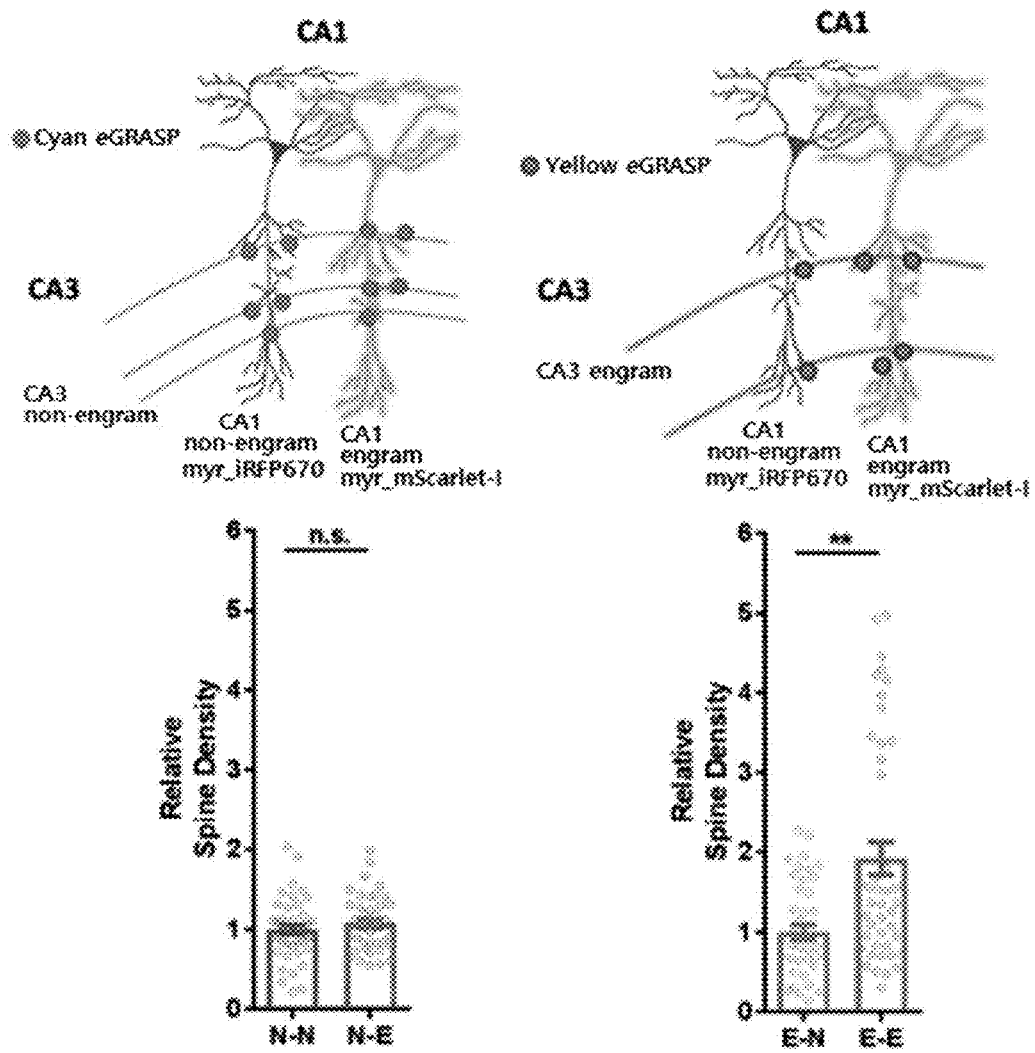

[Fig. 2e]
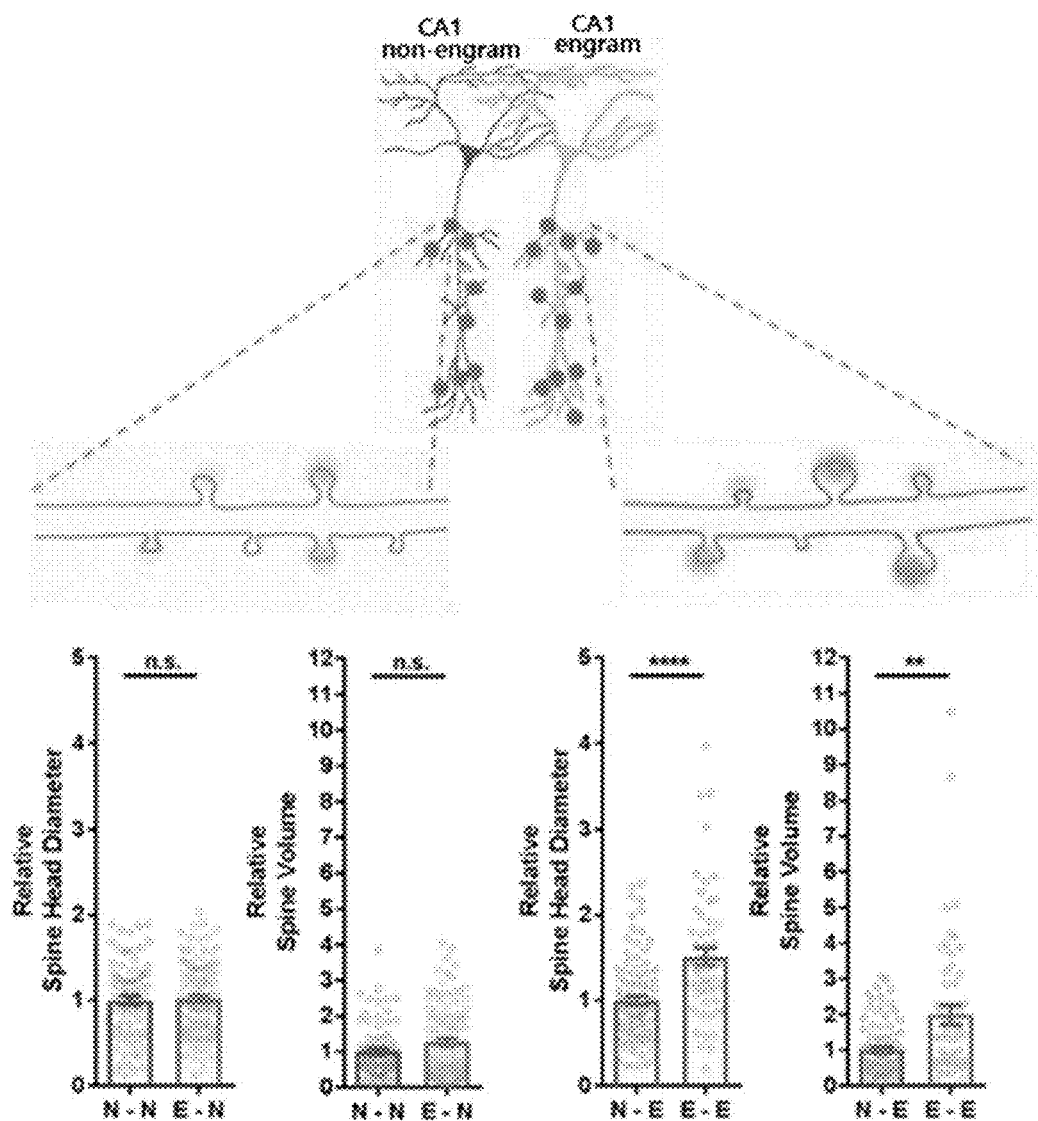

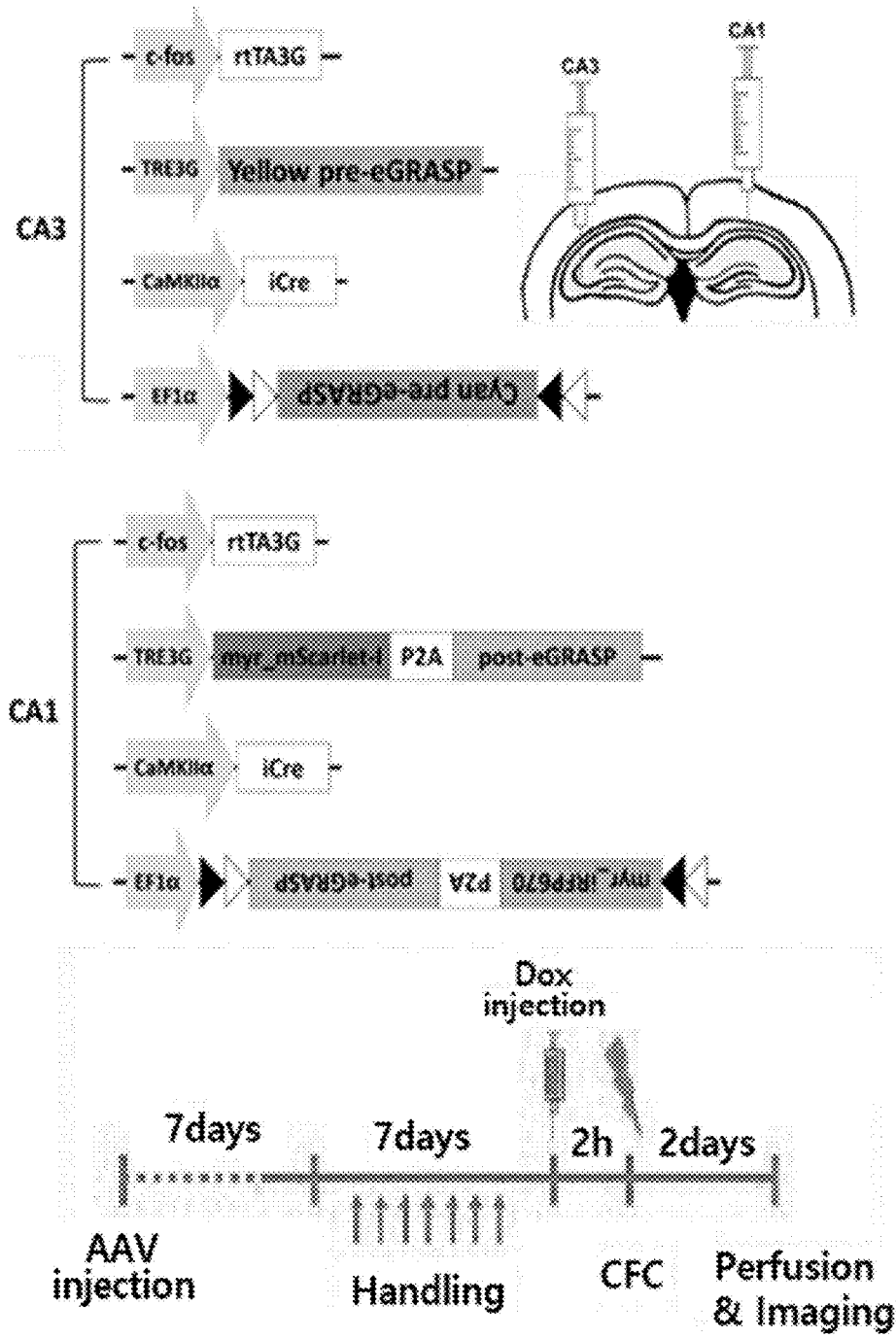

[Fig. 3b]
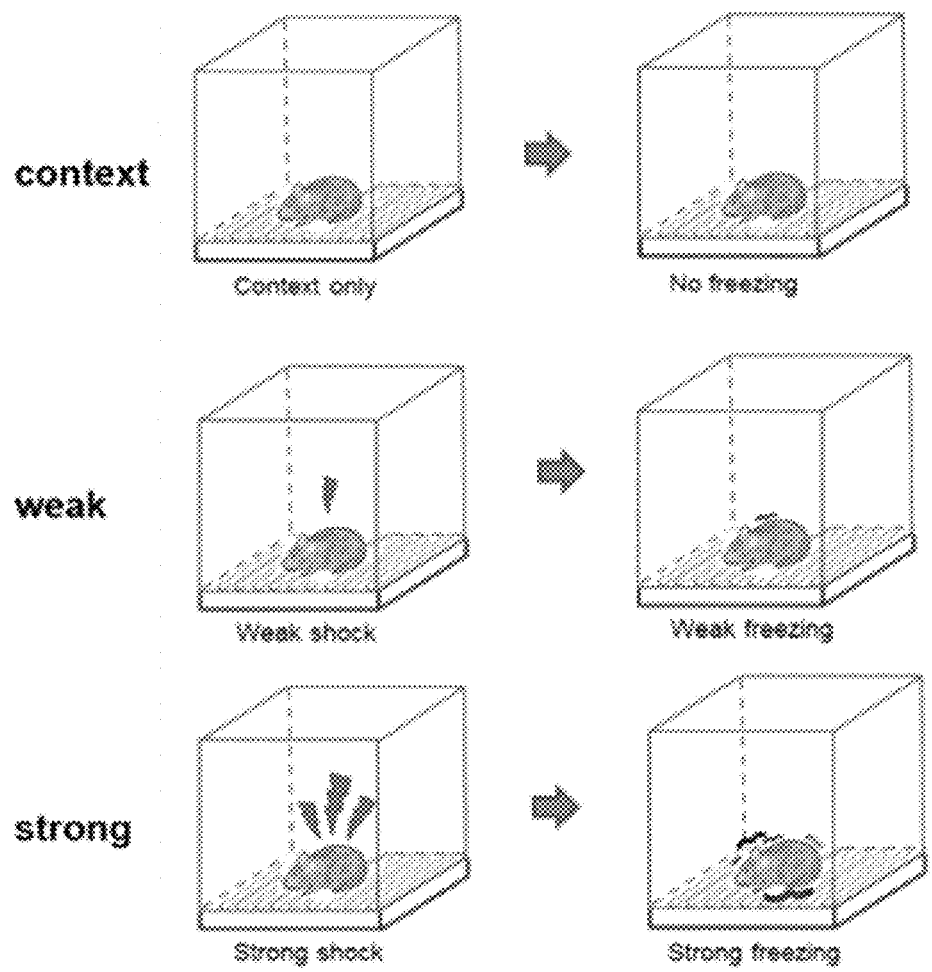

[Fig. 3c]
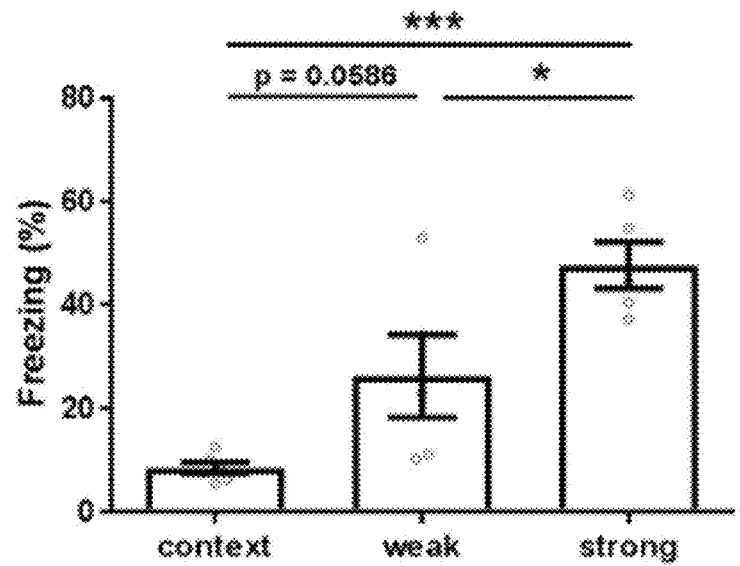
[Fig. 3d]
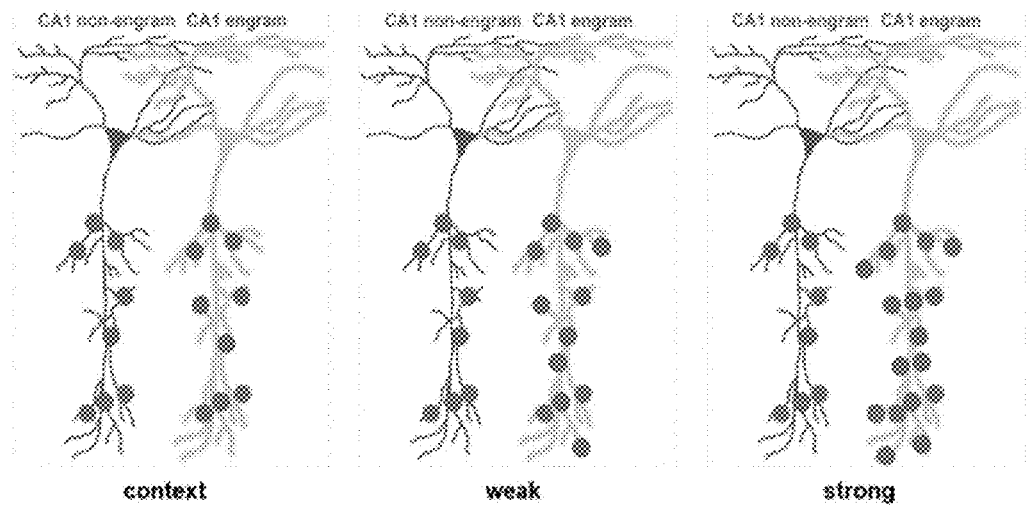

[Fig. 3e]
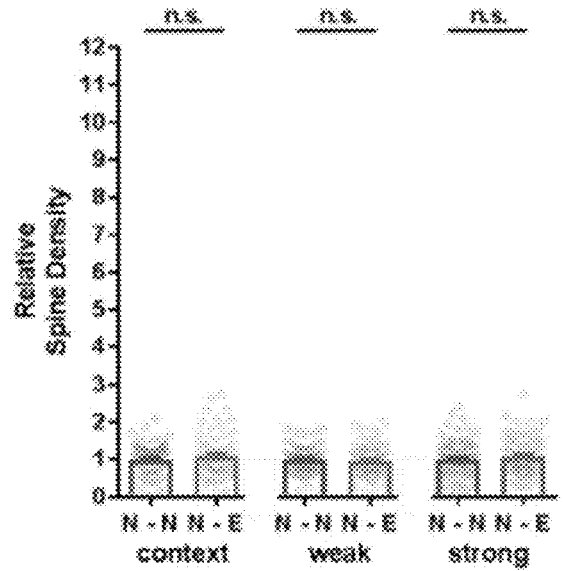
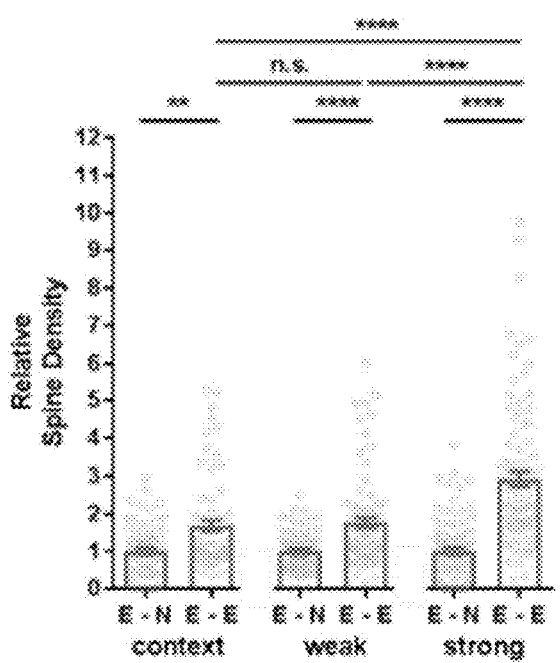

[Fig. 3f]
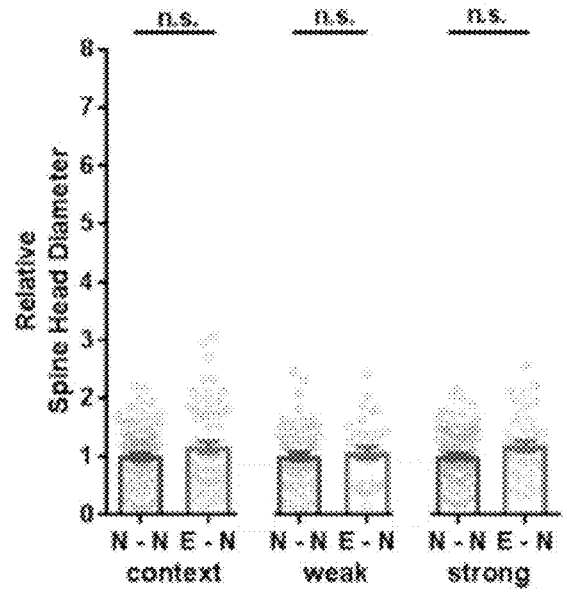
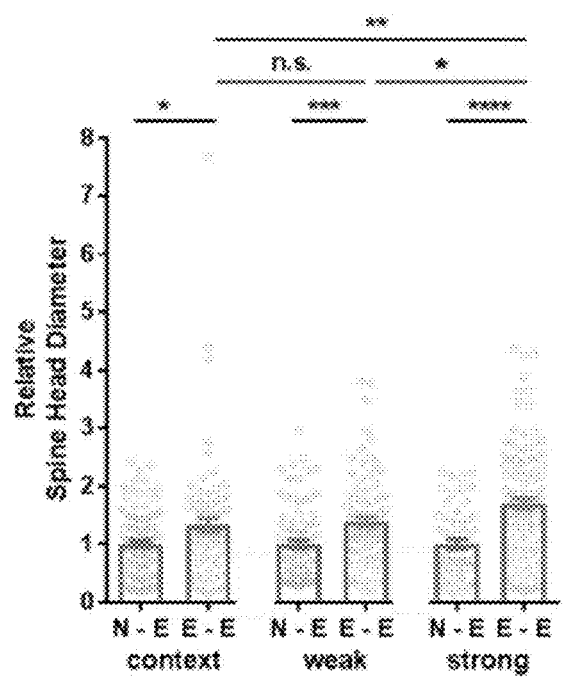

[Fig. 4a]
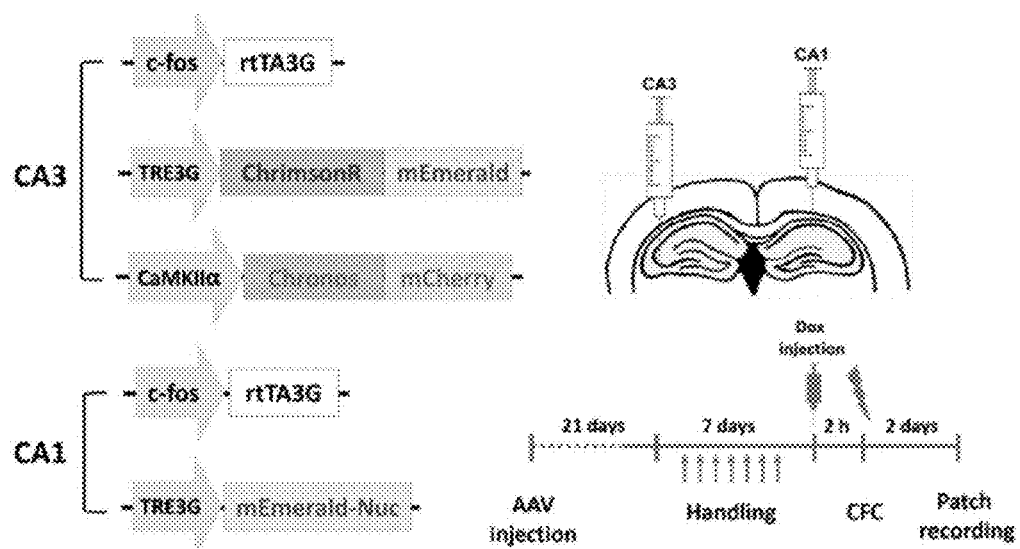
[Fig. 4b]
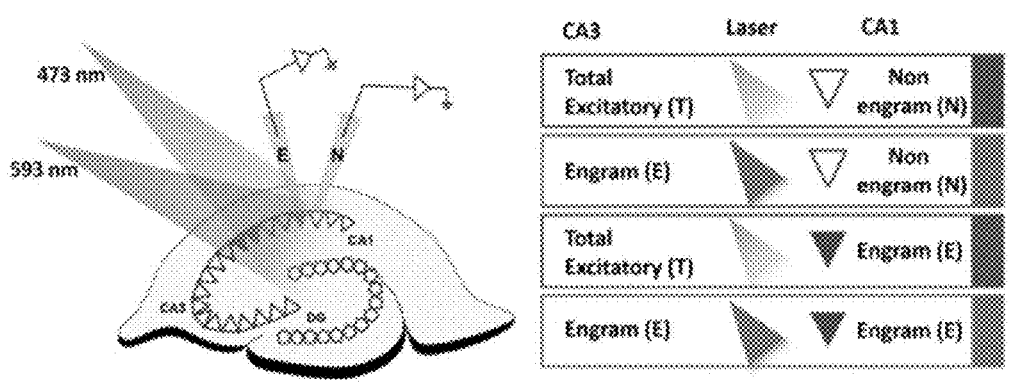

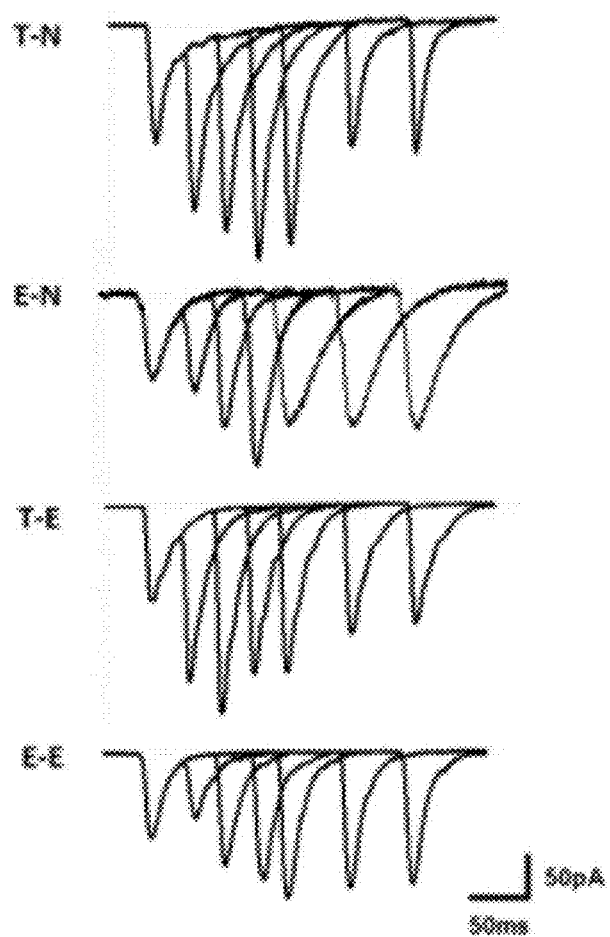
[Fig. 4c]

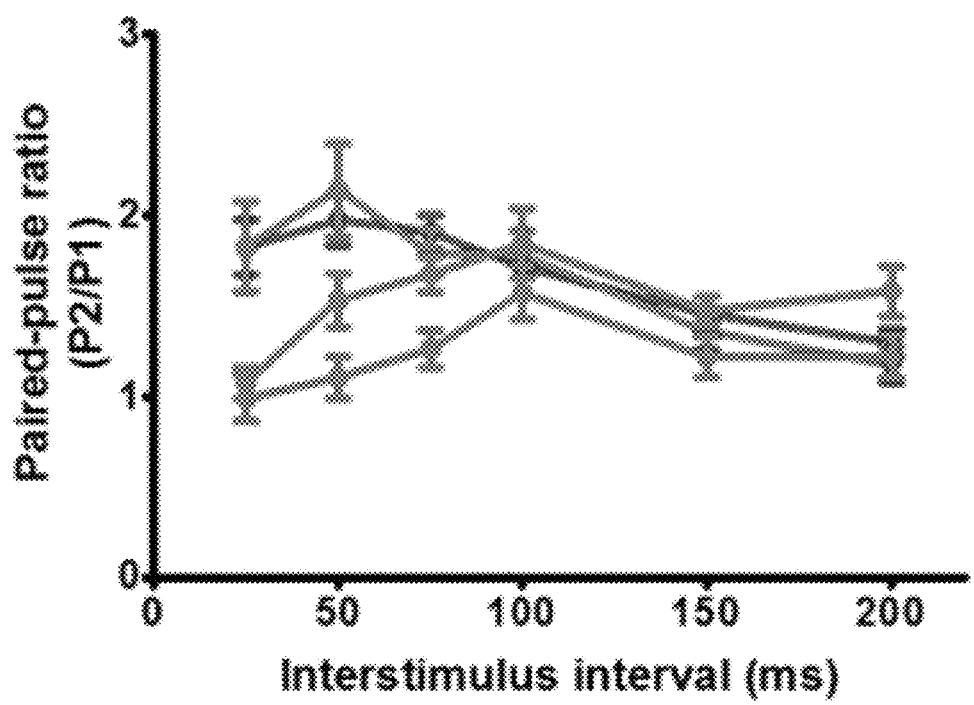
[Fig. 4d]

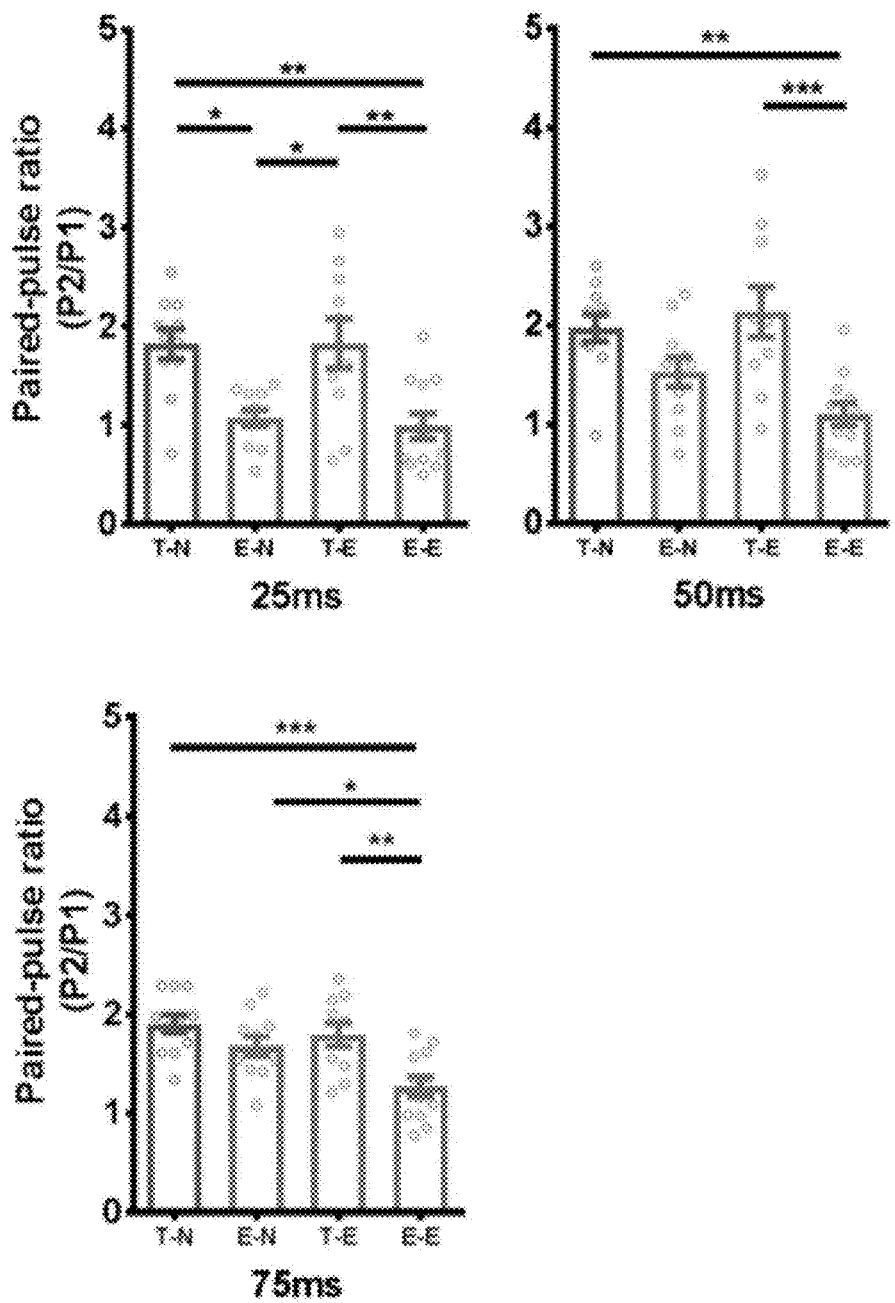
[Fig. 4e]

[Fig. 4f]
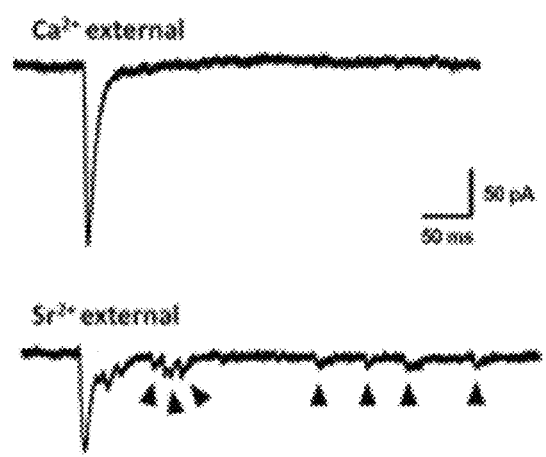
[Fig. 4g]
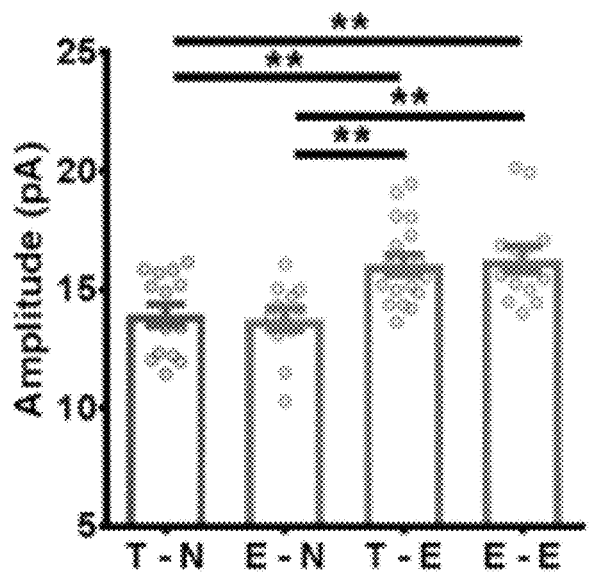

[Fig. 4h]
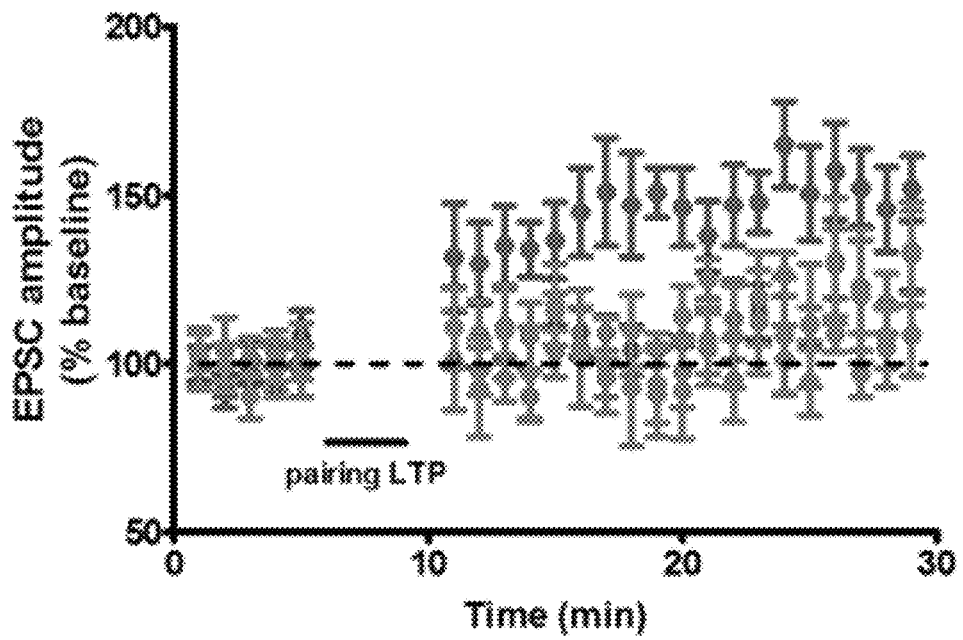
[Fig. 4i]
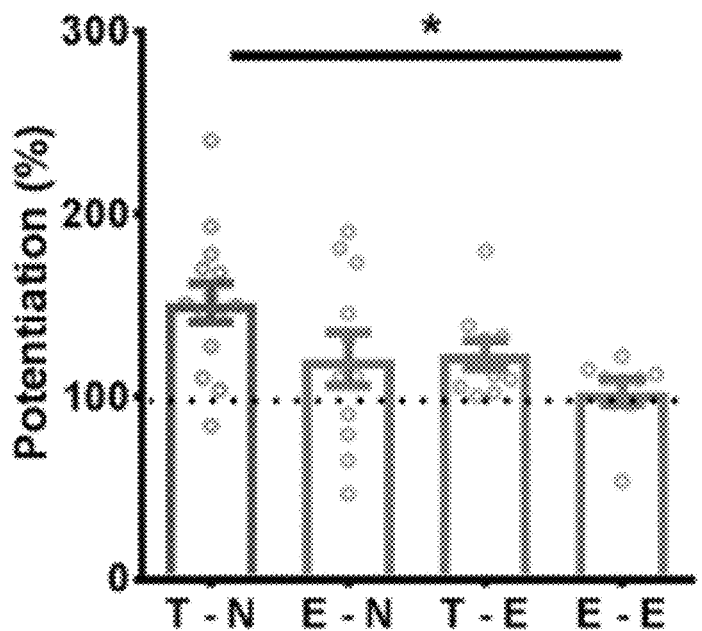

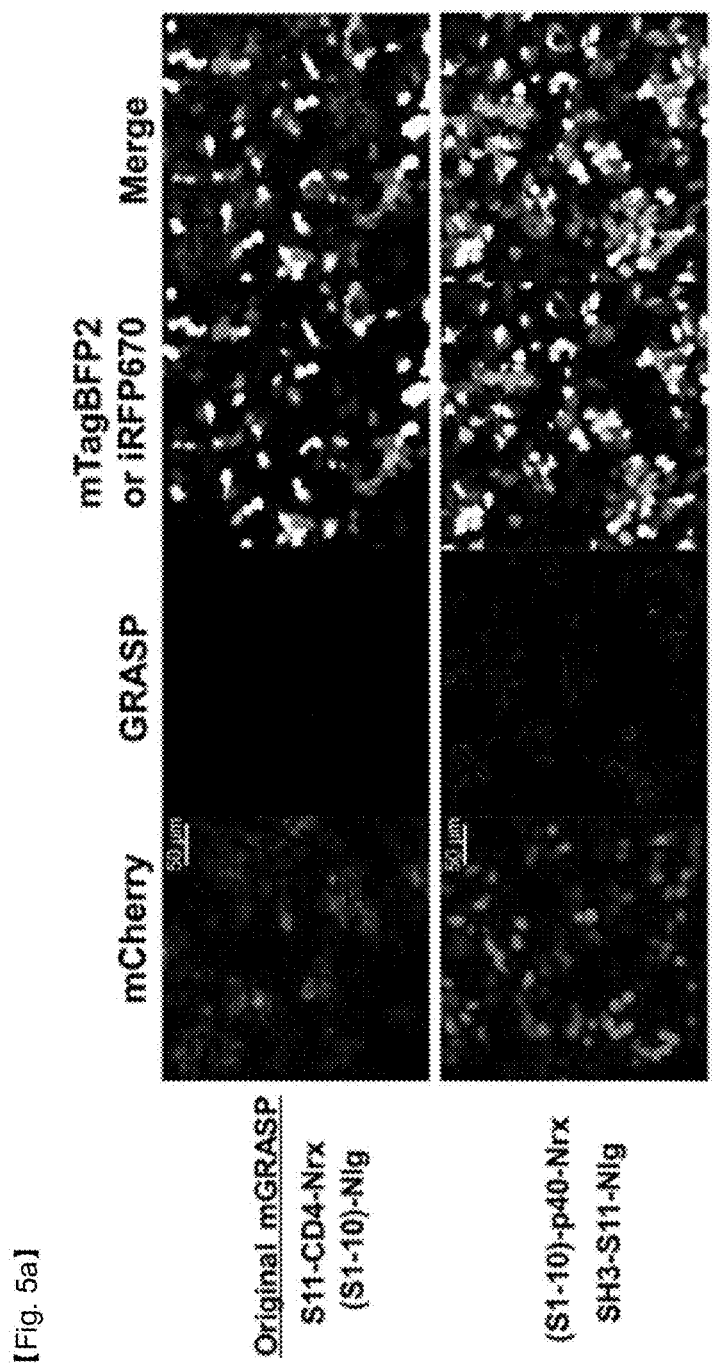
[Fig. 5a]

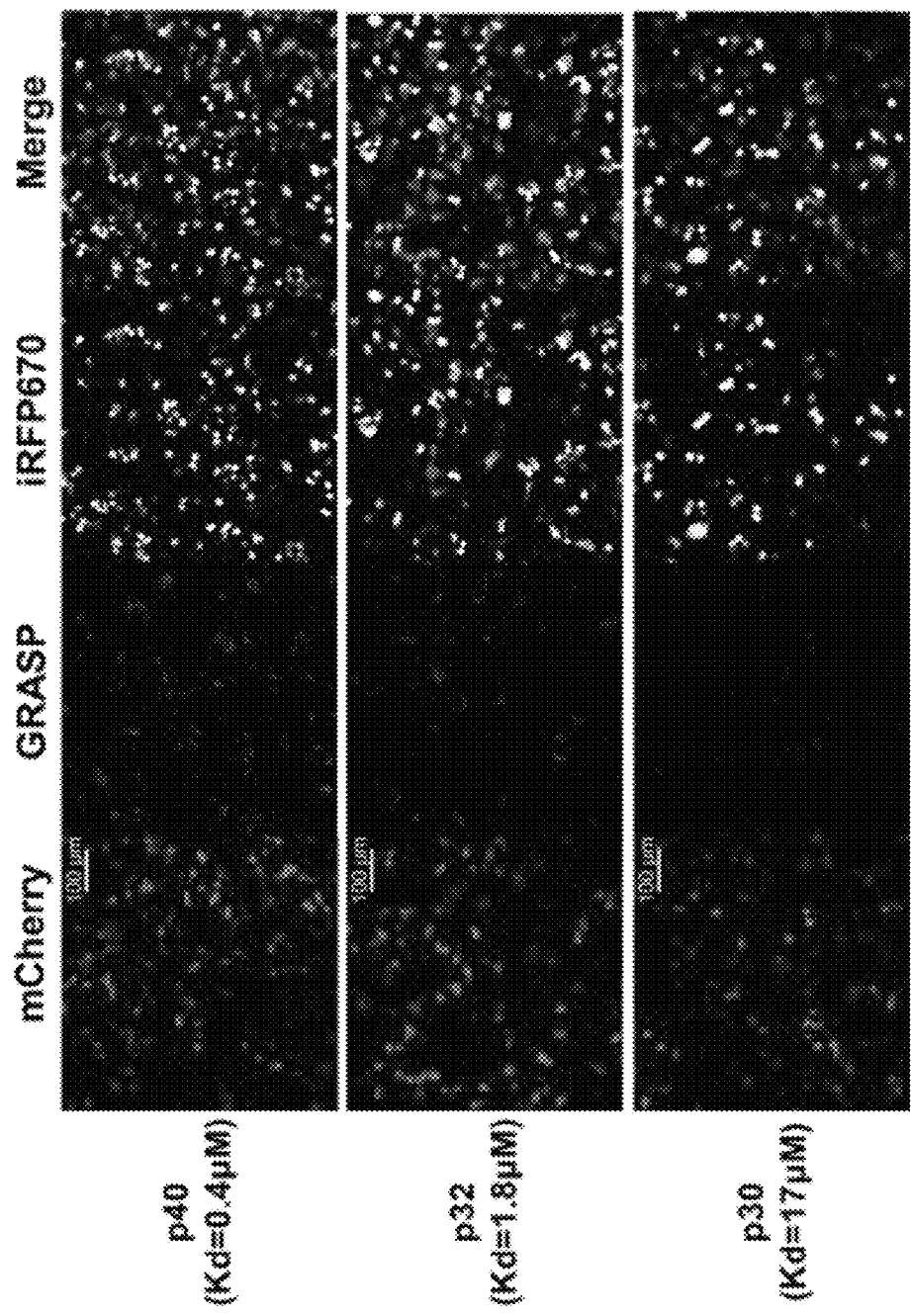
[Fig. 5b]

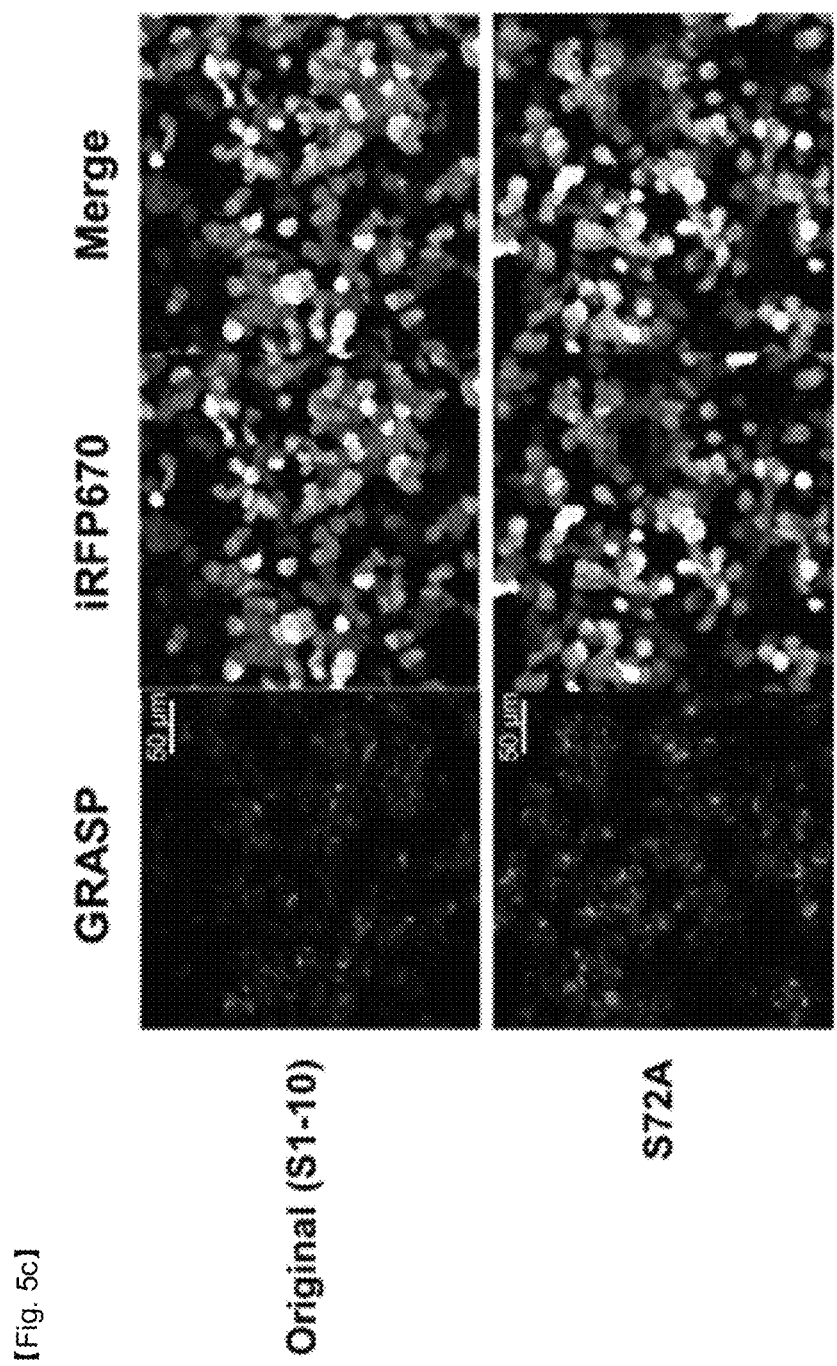
[Fig. 5c]

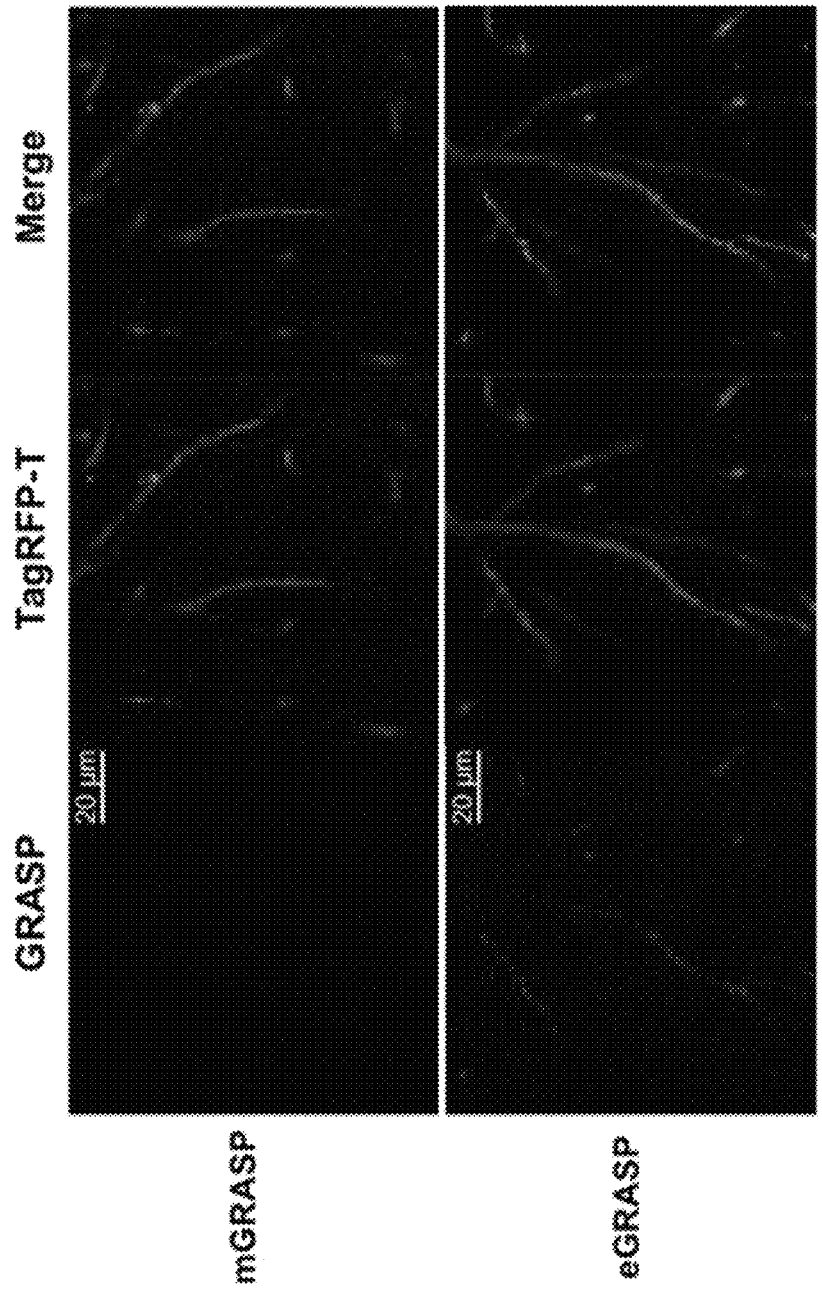
[Fig. 5d]

[Fig. 6a]
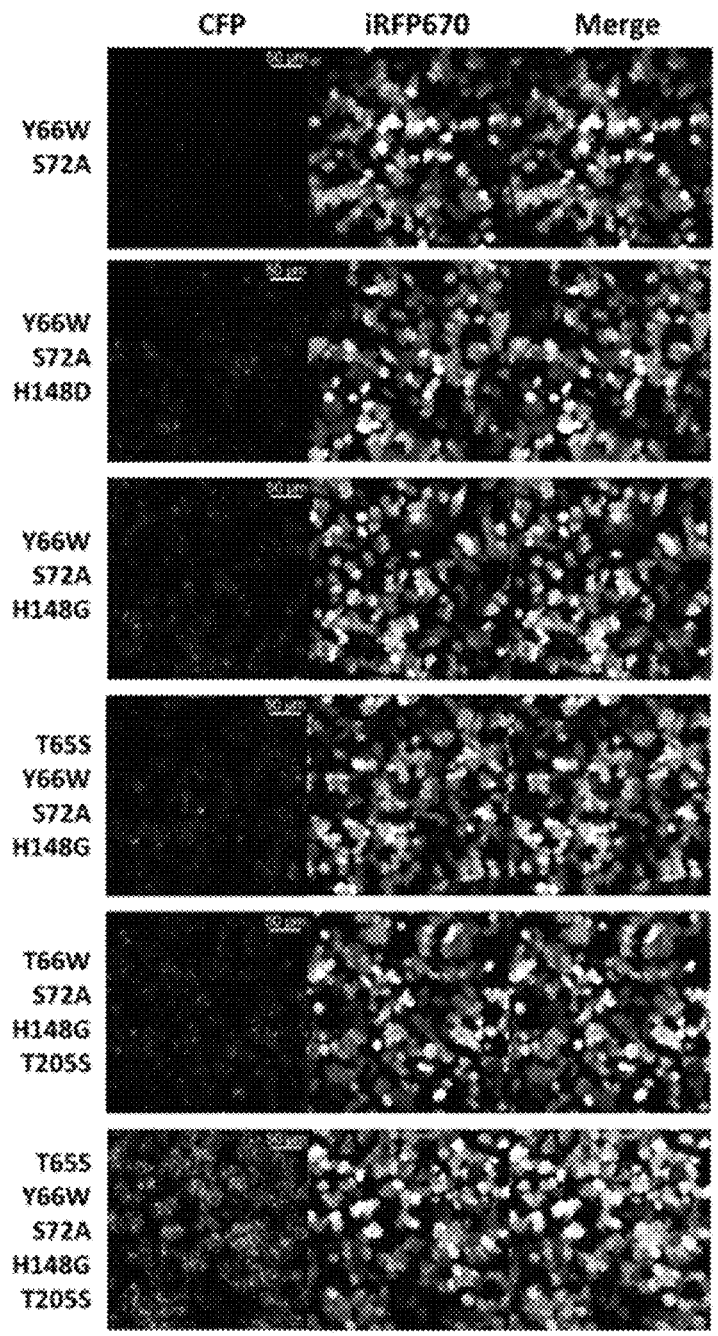

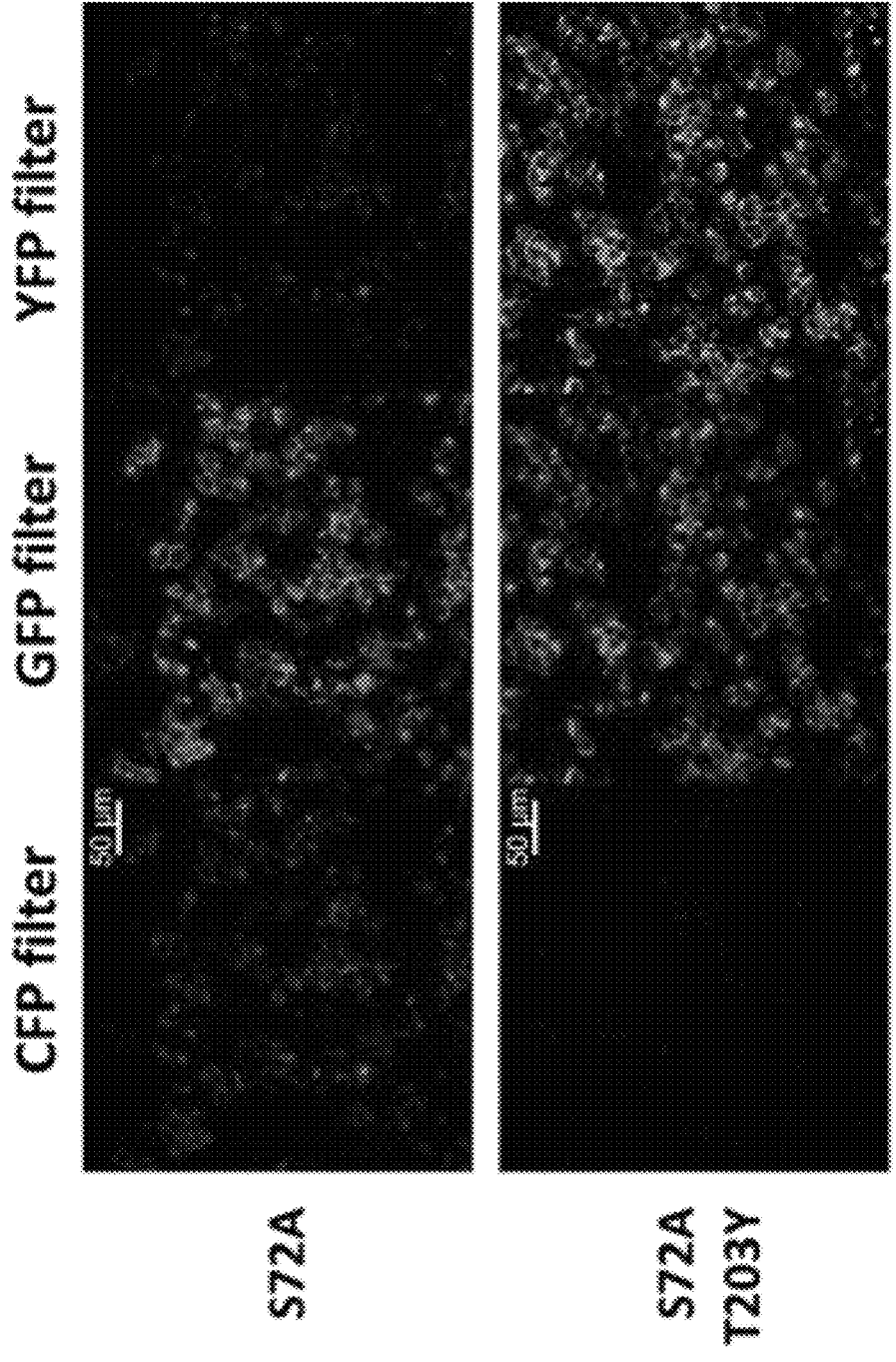
[Fig. 6b]

[Fig. 7a]
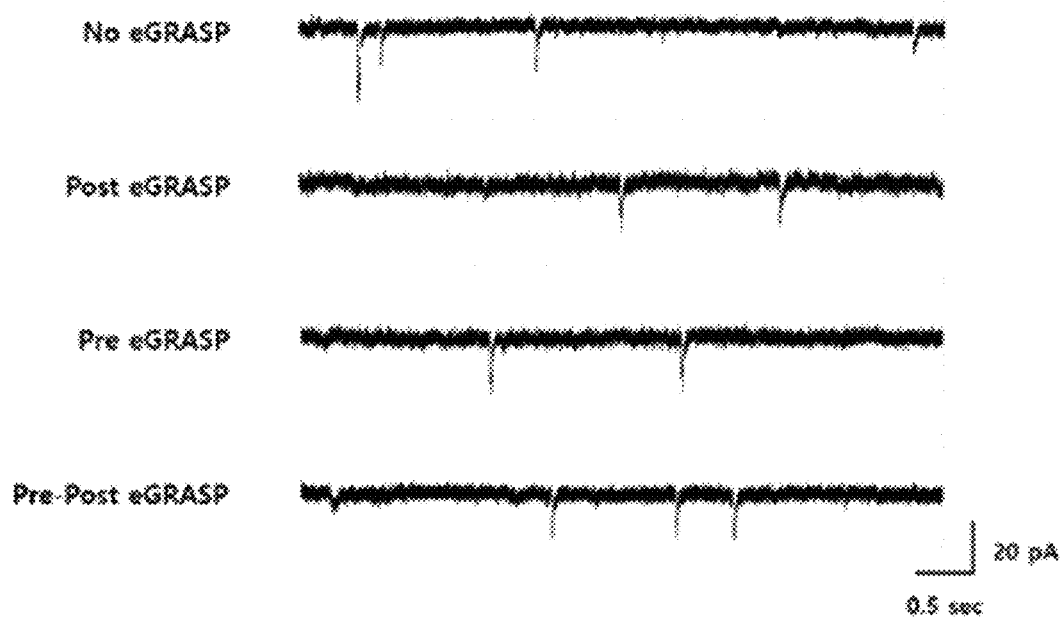

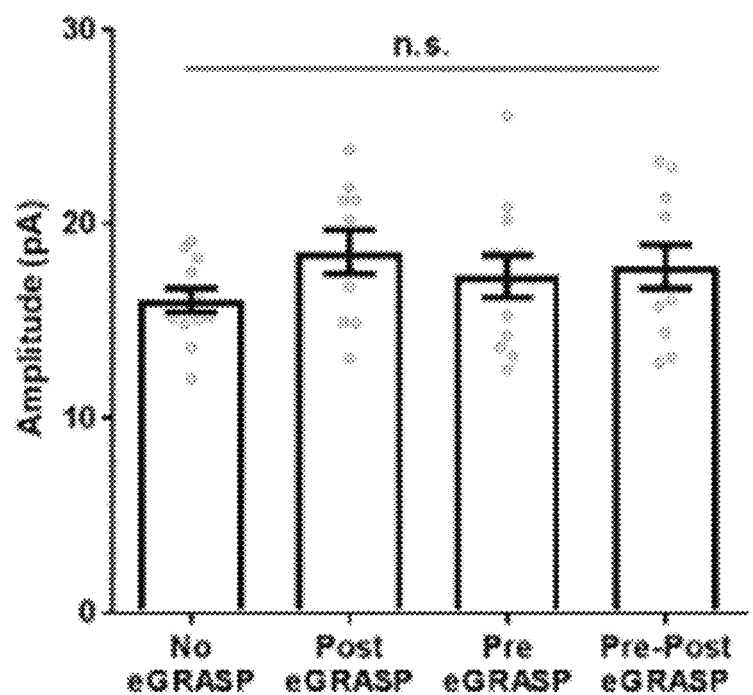
[Fig. 7b]

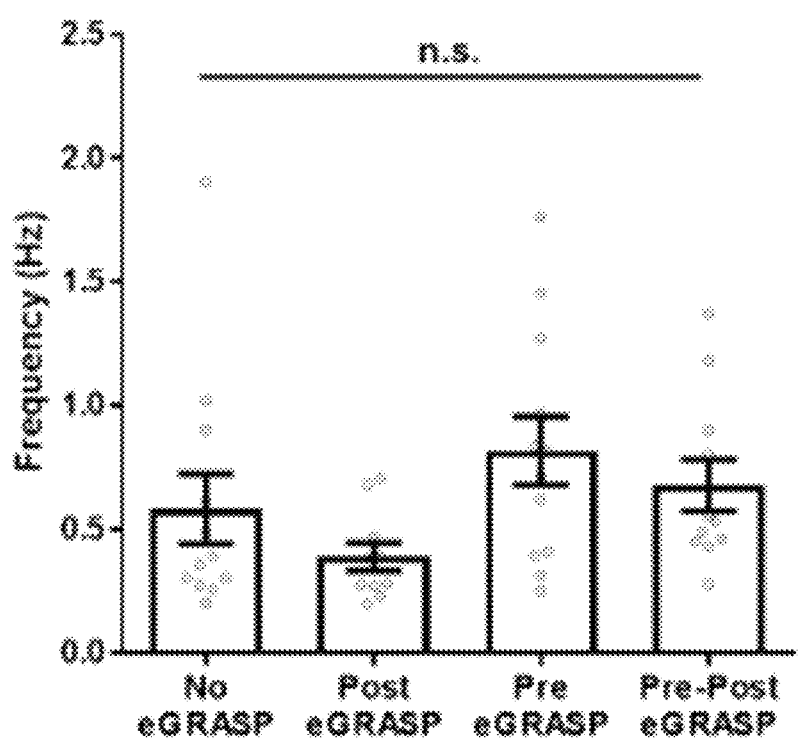
[Fig. 7c]

[Fig. 8a]
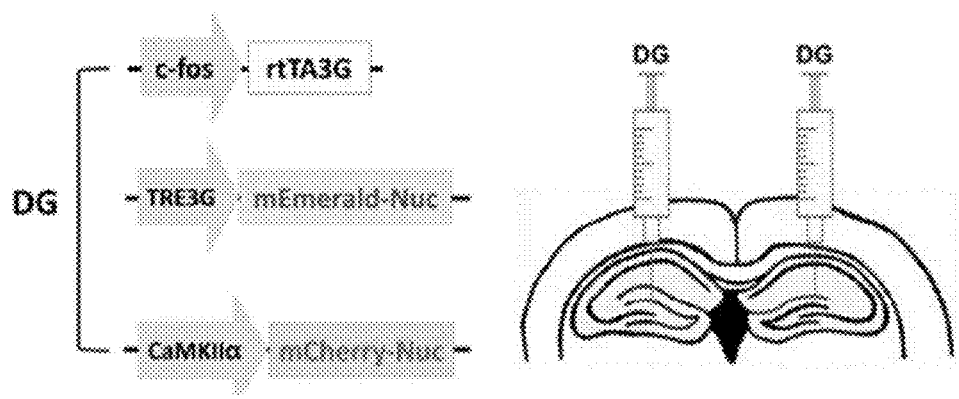
[Fig. 8b]
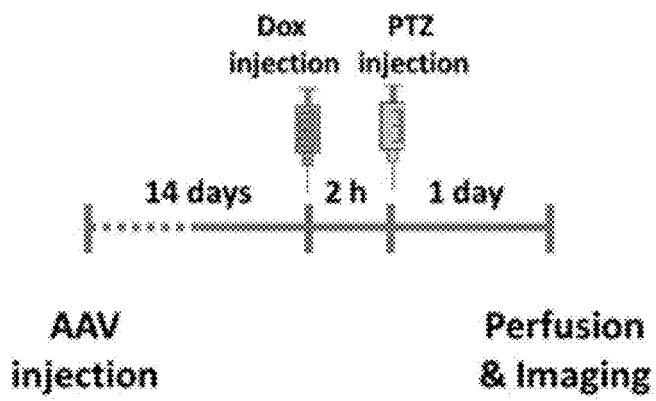

[Fig. 8c]
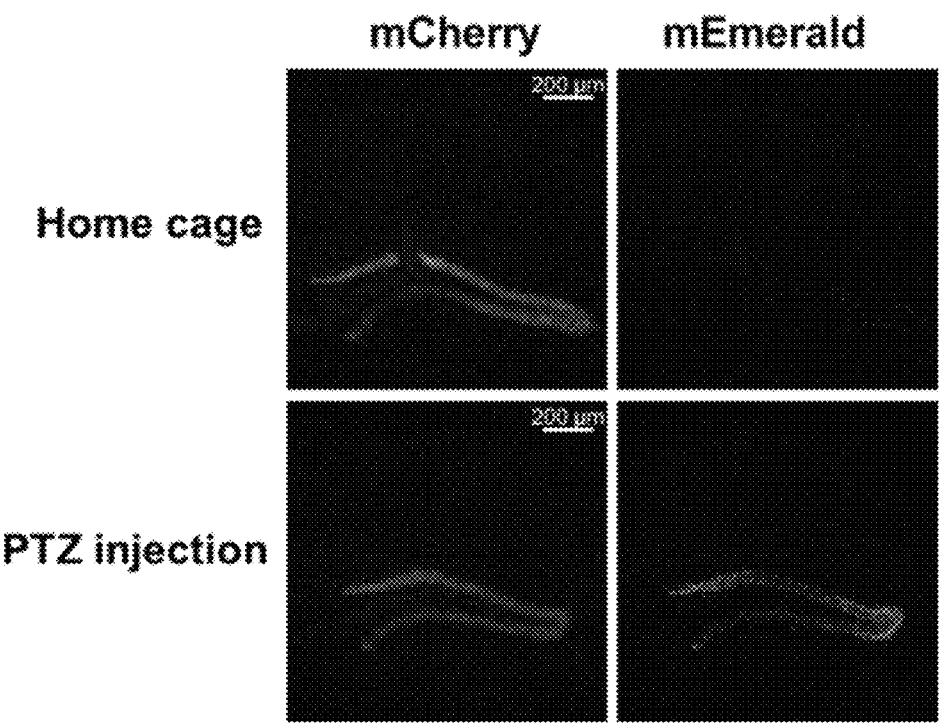

[Fig. 9a]
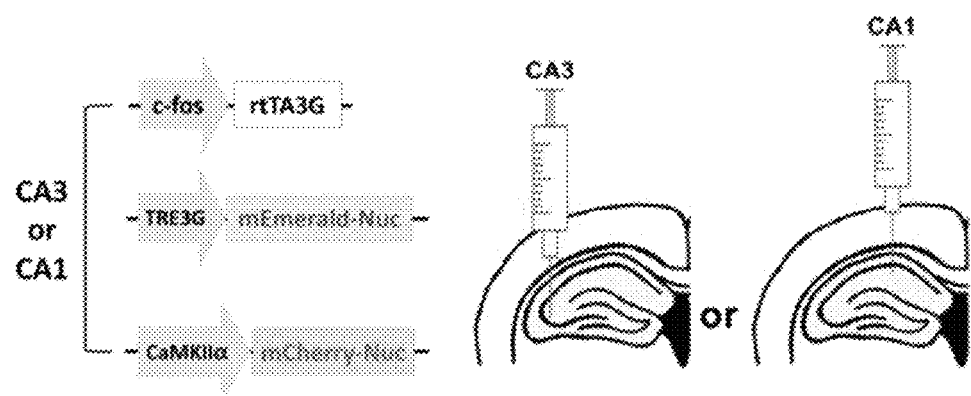
[Fig. 9b]
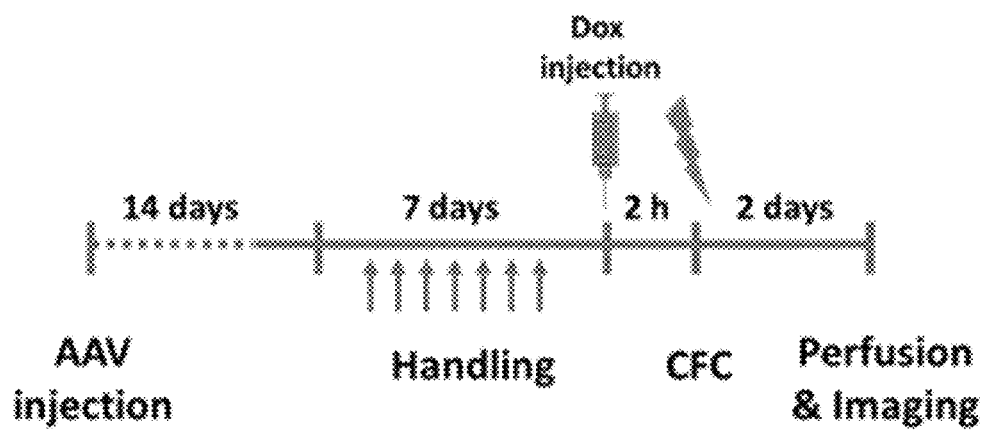

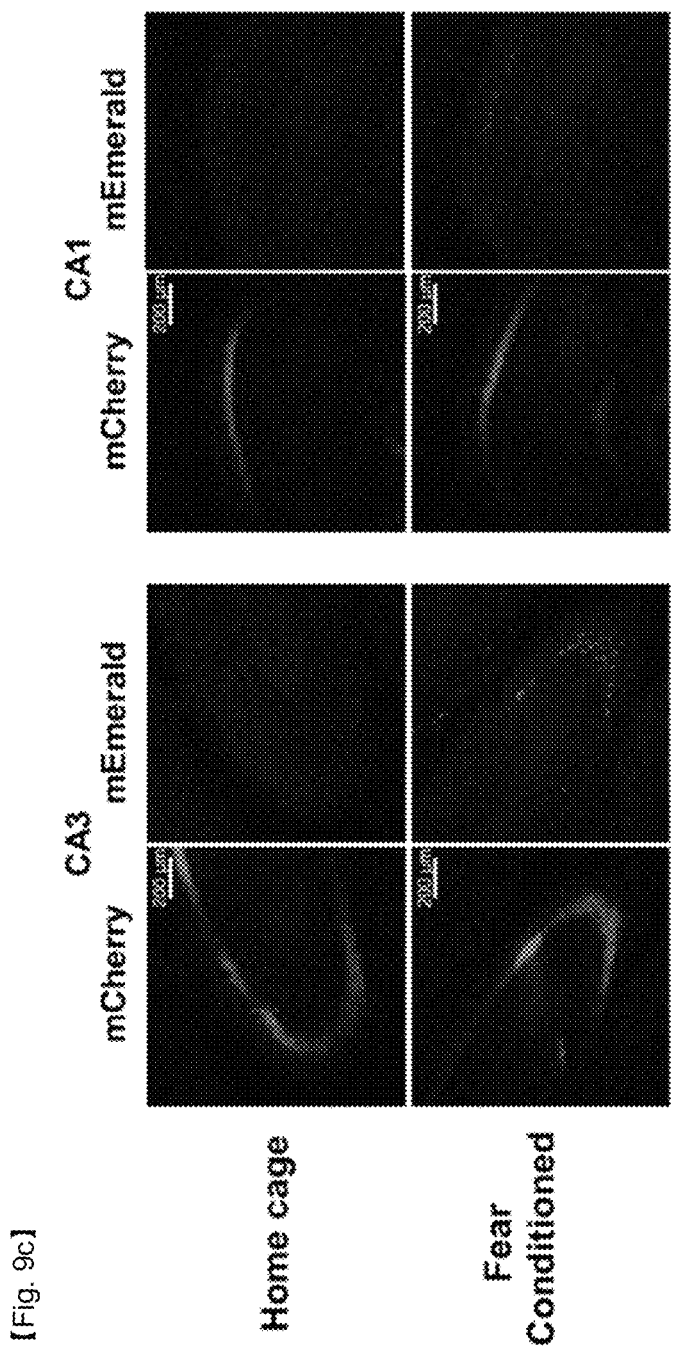
[Fig. 9c]

[Fig. 9d]
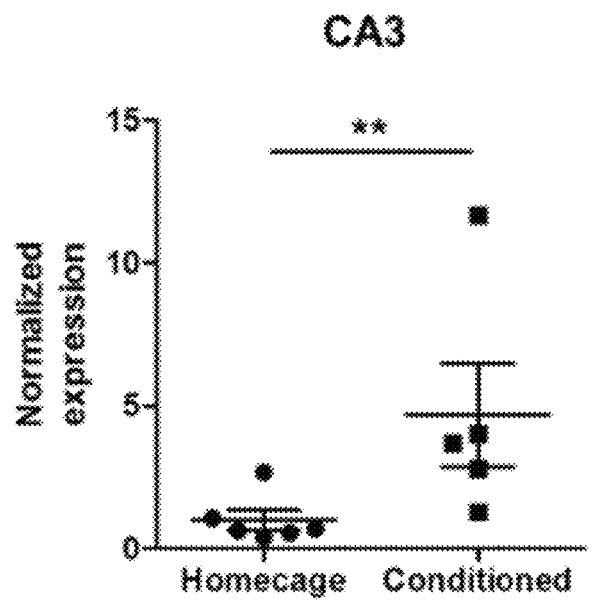
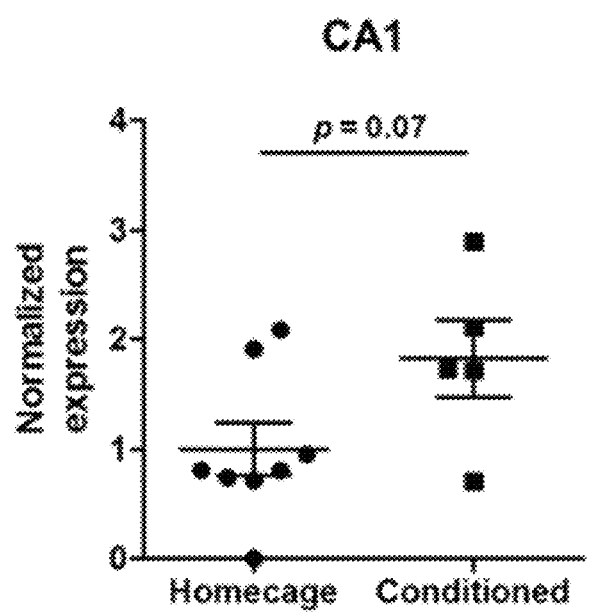

[Fig. 10a]
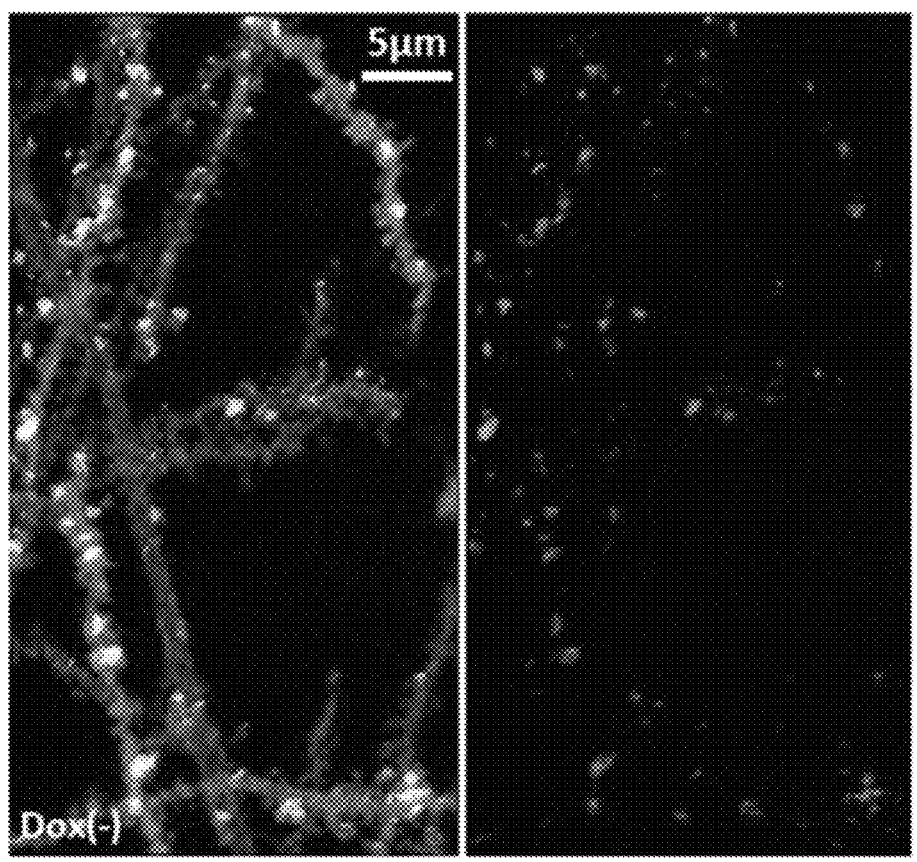

[Fig. 10b]
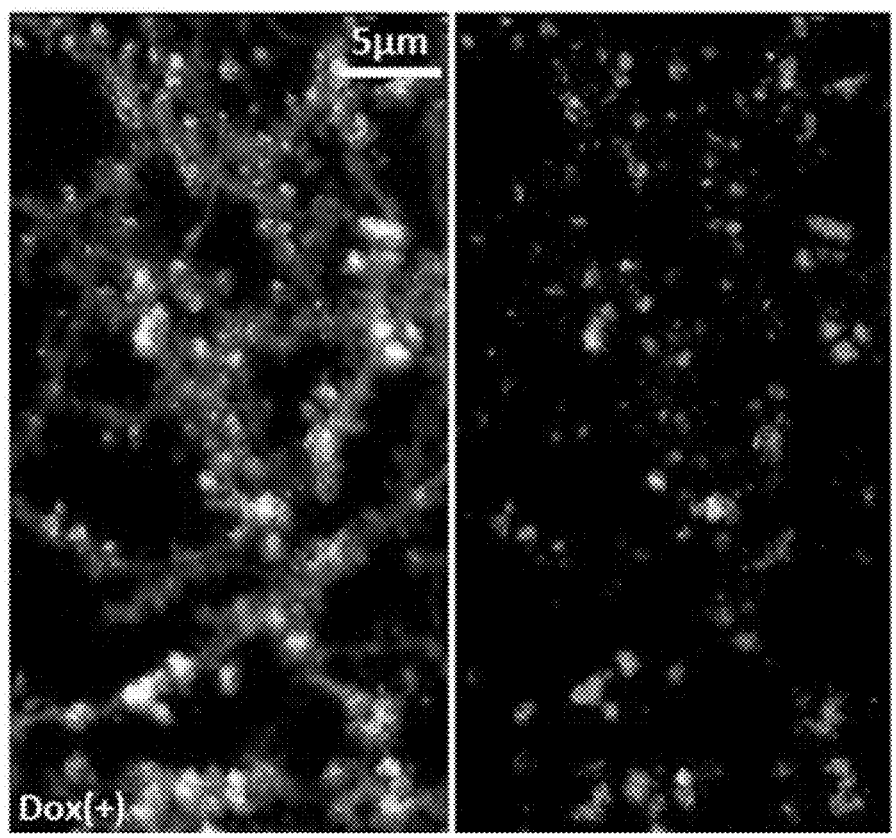

|  | on iRFP670 dendrite |
|---|---|
| cyan & yellow overlap / cyan | 40.25 % |
| cyan & yellow overlap / yellow | 78.38 % |

B

|  | on mScarlet-I dendrite |
|---|---|
| cyan & yellow overlap / cyan | 50.00 % |
| cyan & yellow overlap / yellow | 80.37% |

C

| iRFP670 & mScarlet-I overlap / iRFP670 | 20.93 % |
|---|---|
| iRFP670 & mScarlet-I overlap / mScarlet-I | 11.61% |

[Fig. 12]
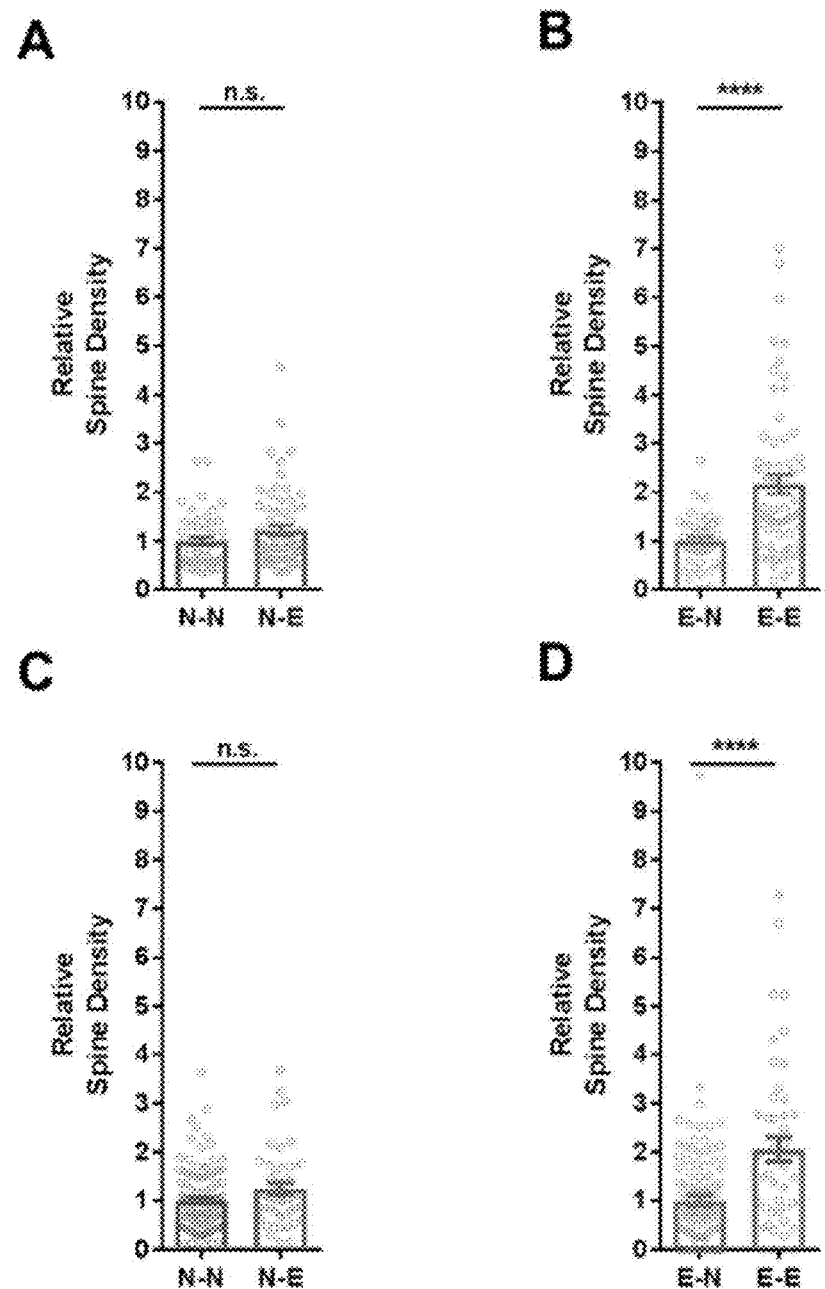

[Fig. 13]
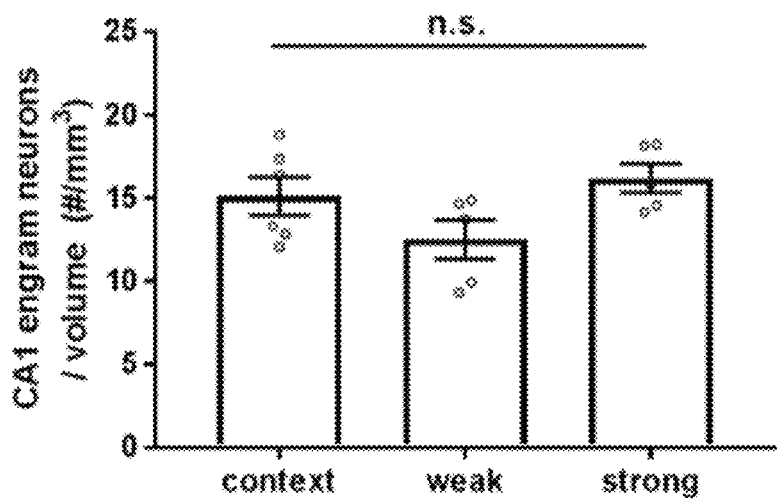
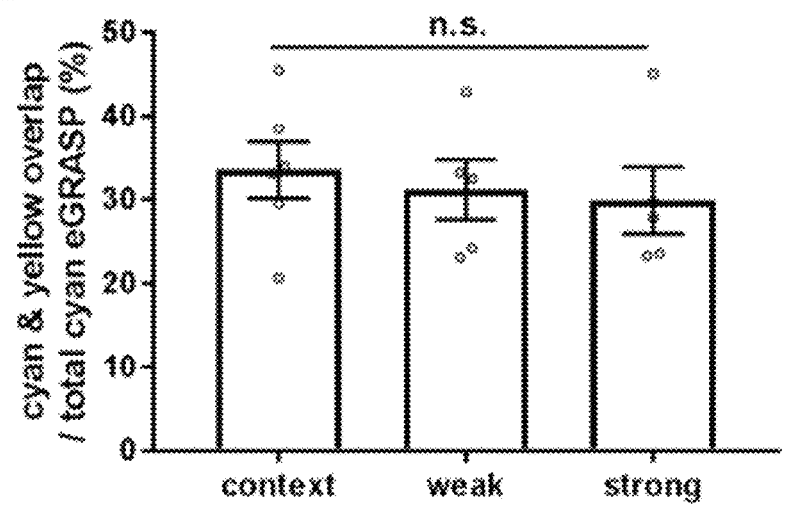

[Fig. 14]
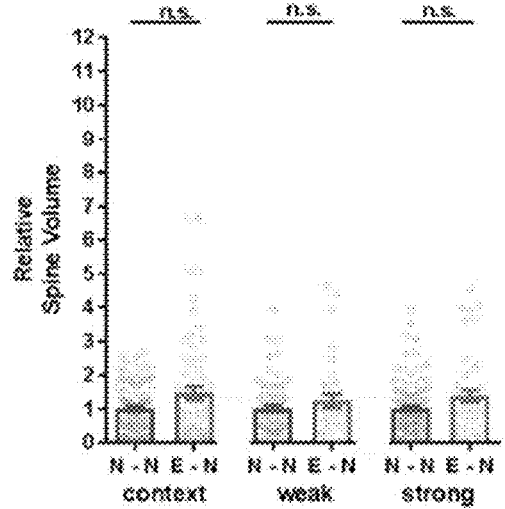
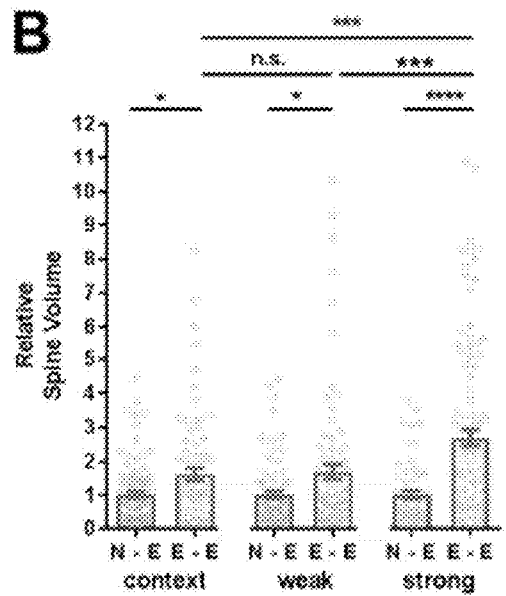

[Fig. 15]

Post-eGRASP: SEQ ID NO.14

IgG kappa signal peptide (italic with line),

Abl Sh3 domain (bold with line), strand 11 (italic and bold with line), neuroligin1 stalk, transmembrane and intracellular domain with deletion (line).

*<u>METDTLLLWVLLLWVPGSTGDAPV</u>*GG<u>NDPNLFVALYDFVASGDNT LSITKGEKLRVLGYNHNGEWCEAQTKNGQGWVPSNYITPVNST</u>GGGSGGGS<u>*RDHMVLHEYVNAAGIT*</u>GGGSGGGSGT<u>LELVPHLHNL NDISQYTSTTTKVPSTDITLRPTRKNSTPVTSAFPTAKQDDPKQQPSP FSVDQRDYSTELSVTIAVGASLLFLNILAFAALYYKKDKRRHDVHR RCSPQRTTTNDLTHAPEEEIMSLQMKHTDLDHECESIHPHEVVLRT ACPPDYTLAMRRSPDDIPLMTPNTITMIPNTIPGIQPLHTFNTFTGGQ NNTLPHPHPHPHSHS</u>

[Fig. 16]

Cyan pre-eGRASP (p30 version): SEQ ID NO.12
IgG kappa signal peptide (italic with line),
strand 1-10 with mutations (bold with line, box for cyan-specific mutated amino acids),
p30 (bold and italic with line),
neurexin1b stalk, transmembrane and intracellular domain (line)
(p32 version has a replacement of APTKPPPLPP to SPSYSPPPPP).

*METDTLLLWVLLLWVPGSTGDAPV*GG**SKGEELFTGVVPILVELDGD
VNGHKFSVRGEGEGDATIGKLTLKFICTTGKLPVPWPTLVTTL
SWGVQCFA\*RYPDHMKRHDFFKSAMPEGYVQERTISFKDDGK
YKTRAVVKFEGDTLVNRIELKGTDFKEDGNILGHKLEYNFNSG
NVYITADKQKNGIKANFTVRHNVEDGSVQLADHYQQNTPIGDG
PVLLPDNHYLSTQSVLSKDPNEK**TGGSGGSGGSR*APTKPPPLPP*G
GGSGGGSGTEVPSSMTTESTATAMQSEMSTSIMETTTTLATSTARR
GKPPTKEPISQTTDDILVASAECPSDDEDIDPCEPSSGGLANPTRVGG
REPYPGSAEVIRESSSTTGMVVGIVAAAALCILILLYAMYKYRNRDE
GSYHVDESRNYISNSAQSNGAVVKEKQPSSAKSANKNKKNKDKEY
YV

[Fig. 17]
pre-eGRASP(p30): SEQ ID NO.11
IgG kappa signal peptide (italic with line),
strand 1-10 with S72A mutation (bold with line, asterisk for S72A),
p30 (bold and italic with line),
neurexin1b stalk, transmembrane and intracellular domain (line)
(p32 version has a replacement of APTKPPPLPP to SPSYSPPPPP).

*METDTLLLWVLLLWVPGSTGDAPV*GG**SKGEELFTGVVPILVELDGD VNGHKFSVRGEGEGDATIGKLTLKFICTTGKLPVPWPTLVTTL TYGVQCFA\*RYPDHMKRHDFFKSAMPEGYVQERTISFKDDGKY KTRAVVKFEGDTLVNRIELKGTDFKEDGNILGHKLEYNFNSHN VYITADKQKNGIKANFTVRHNVEDGSVQLADHYQQNTPIGDGP VLLPDNHYLSTQTVLSKDPNEK**TGGSGGSGGSR*APTKPPPLPP*GG GSGGGSGTEVPSSMTTESTATAMQSEMSTSIMETTTLATSTARRG KPPTKEPISQTTDDILVASAECPSDDEDIDPCEPSSGGLANPTRVGGR EPYPGSAEVIRESSSTTGMVVGIVAAAALCILILLYAMYKYRNRDE GSYHVDESRNYISNSAQSNGAVVKEKQPSSAKSANKNKKNKDKEY YV

[Fig. 18]

Yellow pre-eGRASP(p30) : SEQ ID NO.13

IgG kappa signal peptide (italic with line), strand 1-10 with mutations (bold with line, box for yellow-specific mutated amino acid), p30(bold and italic with line), neurexin1b stalk, transmembrane and intracellular domain (line)

(p32 version has a replacement of APTKPPPLPP to SPSYSPPPPP).

*METDTLLLWVLLLWVPGSTGDAPV*GG**SKGEELFTGVVPILVELDGD VNGHKFSVRGEGEGDATIGKLTLKFICTTGKLPVPWPTLVTTL TYGVQCFA\*RYPDHMKRHDFFKSAMPEGYVQERTISFKDDGKY KTRAVVKFEGDTLVNRIELKGTDFKEDGNILGHKLEYNFNSHN VYITADKQKNGIKANFTVRHNVEDGSVQLADHYQQNTPIGDGP VLLPDNHYLSYQTVLSKDPNEK**TGGSGGSGGSR*APTKPPPLPP*GG GSGGGSGTEVPSSMTTESTATAMQSEMSTSIMETTTLATSTARRG KPPTKEPISQTTDDILVASAECPSDDEDIDPCEPSSGGLANPTRVGGR EPYPGSAEVIRESSSTTGMVVGIVAAAALCILILLYAMYKYRNRDE GSYHVDESRNYISNSAQSNGAVVKEKQPSSAKSANKNKKNKDKEY YV

[Fig. 19]
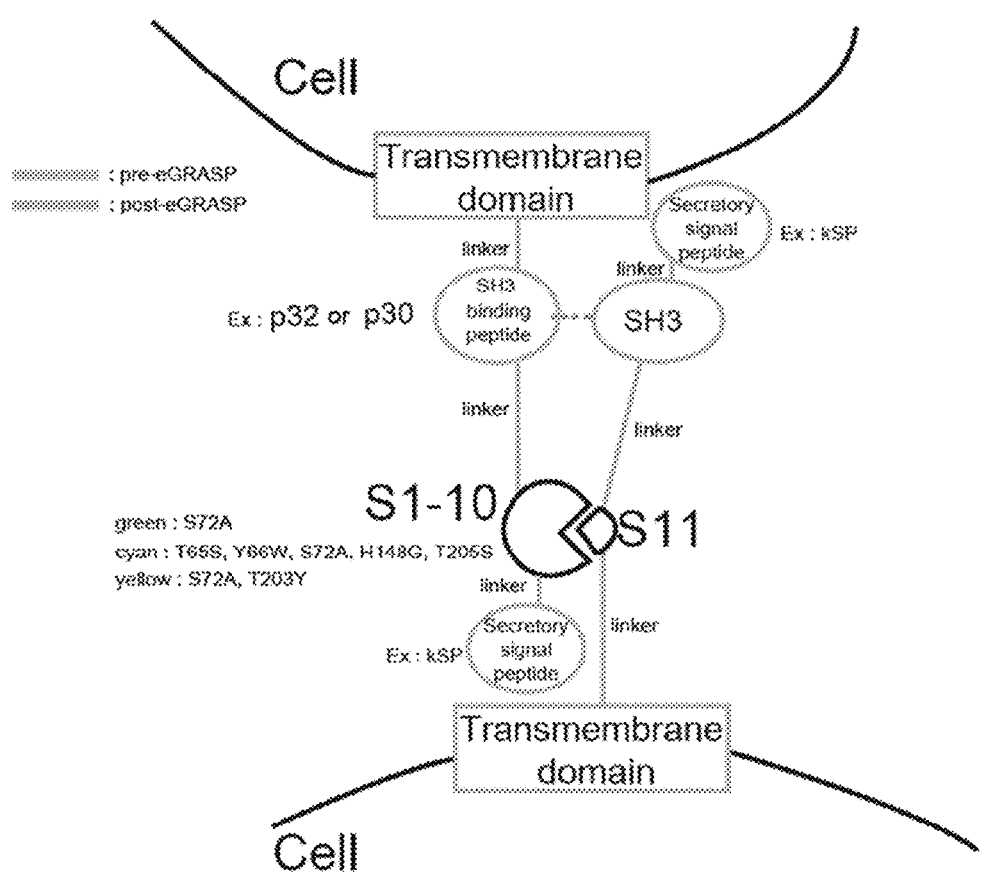

INTERCELLULAR PROXIMITY LABELING USING EGRASP

TECHNICAL FIELD

The present disclosure relates to an intercellular proximity labeling using enhanced dual-GRASP (Green fluorescent protein Reconstitution Across Synaptic Partners) system, and a method for detecting a neural network related to memory using the same.

BACKGROUND ART

Synapse is a connection point that transmits signals between two neurons, that is, between a presynaptic neuron that gives a signal and a postsynaptic neuron that receives a signal, and is known as a minimum functional unit of the nervous system. Not only basic functions of the nervous system such as senses and movement but also advanced abilities such as memory and cognition are all based on synapses. Therefore, it is important to study a nervous system in terms of synaptic units.

Studying in terms of synaptic units can be broadly divided into two meanings. First, since the nervous system is a neural network of neurons, there are attempts to observe connections between neurons up to synaptic units. With the technology up to now, it is possible to know to which part the axon bundle is sent from one part, but it was not possible to know exactly which neuron and synapse are formed. In addition, it was not possible to know what kind of structure they function to form synapses. However, because the structure and function of the nervous system are closely related, it is important to observe the connection structure of nerve cells by synaptic units in order to study the function of the nervous system.

Second, there is an attempt to observe changes in a single synaptic unit. Synapse, especially neural spine which is the postsynaptic site, has plasticity that its structure and function are changed by stimulation. When the nervous system is stimulated by plasticity, it changes in the size and function of the neural spine, which affects subsequent responses. Therefore, studying how a specific stimulus changes synaptic structure and function, and studying molecular mechanisms, are the basis for studying the structure and function of the nervous system.

Through a number of studies so far, it has been possible to observe the effect of a specific stimulus on the change in the size and volume of the neural spine, but there is not yet known about a method to classify neural spines of one nerve cell into two or more types and directly compare them. This is because neural spines could not be classified according to the type of presynaptic neuron. Accordingly, the present inventors have developed the present invention, which is a new technique capable of classifying the types of presynaptic nerve cells and labeling synapses.

DETAILED DESCRIPTION OF THE INVENTION

Technical Problem

When a protein exhibiting fluorescence, for example, a green fluorescent protein (GFP), is divided into two parts (S1-10, S11), each does not exhibit fluorescence, but when reconstructed in close proximity, it exhibits fluorescence. In one embodiment of the present disclosure, this split-fluorescent protein technique can be applied to nerve cells. That is, when S11 is expressed in presynaptic neuron and S1-10 is expressed in postsynaptic neuron, protein fragments of S1-10 and S11 are bound to each other at synapse between two neurons to exhibit fluorescence. Through this, it is possible to specifically label and select only synapses that bind to specific presynaptic neurons among numerous synapses of postsynaptic neurons. However, in this case, the fluorescence intensity is weak and thus, it is hardly applied widely, it is difficult to observe with a microscope, and it is possible to display only fluorescence in the green wavelength band. Therefore, there is a problem that synapses receiving signals from two or more different presynaptic neurons cannot be distinguished.

In terms of the fluorescence intensity, there was a problem that the fluorescence intensity of the fluorescent protein reconstructed by binding the protein fragments of S1-10 and S11 is weak compared with a general fluorescent protein. In order to solve these problems, the present disclosure introduced several mutations to enhance the fluorescence intensity of the reconstructed fluorescent protein, and consequently, the fluorescence intensity of the reconstructed fluorescent protein according to an embodiment of the present disclosure became significantly strong. In addition, by introducing additional mutations, split-cyan fluorescent protein and split-yellow fluorescent protein that are mutually distinguishable without interference were prepared. According to an embodiment of the present disclosure, using these was made possible to display a number of synapses existing in one neuron depending on the type of presynaptic neuronal population.

In other words, the facts that the intensity of the reconstructed fluorescent protein has increased and that a system has been created in which it was excited by lights of wavelengths that are mutually distinguishable can be considered as a remarkable development. This has become applicable to brains of various mammals. In addition, the color of the fluorescence became distinguishable, thus enabling various experimental approaches. With the existing technology, only a single color was possible, but since it was possible to label two or more colors through the present disclosure, the observations that was impossible with the existing technology, such as the point capable of directly comparing an experimental group and a control group, or experiments comparing what alignment functions in two different brain regions to form synapses, was made possible.

Memories exist in engram cells scattered across the brain. However, although the fact that synaptic plasticity encodes memories is generally accepted, but site-specific substrates in engram cells remain in theory. The present inventors have developed a dual eGRASP technique that examines synapses between engram cells in order to identify specific nerve regions that play a role in memory storage. As a result of applying one embodiment of the present disclosure to an animal model, the number and size of neural spines of CA1 engram cells receiving signals from CA3 engram cells were increased, and the connections between engram cells that store memory strength under contextual fear conditioning were improved. The connection from the already potentiated CA3 engram to the CA1 engram strongly prevented long-term potentiation. These results indicate that the improved structural and functional connectivity between engram cells across two directly connected brain regions forms a synaptic correlation for memory formation.

Technical Solution

An aspect of the present disclosure relates to a method of confirming intercellular contact, comprising the steps of:

introducing a first labeling material and a second labeling material into a first cell and a second cell, respectively; and detecting a signal, wherein the first labeling material and the second labeling material are bound to each other to generate the signal.

Another aspect of the present disclosure relates to a method of confirming memory storing synapses comprising: a step of introducing a gene being initiated with an activity-dependent promoter and encoding a first labeling material into a presynaptic neuron, and introducing a gene encoding the second labeling material into a postsynaptic neuron; and a step of detecting a signal by the binding of the first labeling material and the second labeling material.

Another aspect of the present disclosure relates to an animal comprising: a first cell into which a gene encoding a first labeling material has been introduced, and a second cell into which a gene encoding the second labeling material has been introduced, wherein the first labeling material and the second labeling material are bound to each other to generate a signal. The animal may be a non-naturally occurring transgenic animal, and may be an animal except human, for example, a mammal except human.

Another aspect of the present disclosure relates to a method of preparing an animal model comprising the steps of: introducing a gene encoding a first labeling material into a first cell of the animal, and introducing a gene encoding a second labeling material into a second cell of the animal, wherein the first labeling material and the second labeling material are bound to each other to generate a signal. The animal may be an animal except human, for example, a mammal except human.

The first and second labeling material are fluorescent materials independently selected from commonly used fluorescent materials (small-molecule compounds and proteins), and may be bound to each other to generate fluorescence, and the signal may be a fluorescent signal.

Hereinafter, the present disclosure will be described in more detail.

According to one embodiment of the present disclosure, there is provided a method of confirming intercellular contact, comprising the steps of: introducing a first labeling material and a second labeling material into a first cell and a second cell, respectively; and detecting a signal, wherein the first labeling material and the second labeling material are bound to each other to generate the signal.

The method of confirming intercellular contact may further comprise a step of determining that the first cell and the second cell are in contact with each other when the signal is detected, after the step of detecting the signal.

The "intercellular contact" means contact or proximity between cells. However, it will be clearly understood by those skilled in the art that when the cells are located adjacent to each other within a certain distance even without physical contact between cells, it is possible to express that intercellular contact has occurred. For example, when the first cell and the second cell are positioned with a distance of 100 nm or less, 90 nm or less, 80 nm or less, 70 nm or less, 60 nm or less, 50 nm or less, 40 nm or less, 30 nm or less, 20 nm or less, 10 nm or less, or 5 nm or less (the lower limit is 0 nm or more or exceeds 0 nm), contact between the first cell and the second cell may be confirmed. In one example, when the distance between the first cell and the second cell is 40 nm or less, contact between the first cell and the second cell may be confirmed.

The "first cell" or the "second cell" may mean the cell to be confirmed for confirming intercellular contact or proximity. According to an embodiment of the present disclosure, the first cell or the second cell may be at least one selected from prokaryotic cells and eukaryotic cells. Specifically, it may be at least one selected from the group consisting of animal cells (e.g., mammalian cells), animal-derived cell lines (e.g., HEK293T), plant cells, plant-derived cell lines, microbial cells (e.g., yeast, eumycetes (fungi), bacteria (*E. coli*, etc.), or the like), animal-derived cultured cell, plant-derived cultured cells, and the like. The mammalian cell may be at least one selected from the group consisting of human cells, mammalian cells except humans (e.g., mouse cells, rat cells, or the like), but is not limited thereto. In one example, the cell may be a cell isolated from a living body or a human body (when it is a human cell). Further, according to one embodiment of the present disclosure, the first cell or the second cell may be the same as or different from each other, and may be each independently at least one selected from the group consisting of neurons, astrocyte, microglia, oligodendrocytes, immune cells, T cells, and B cells, but is not limited thereto. The first cell and the second cell may correspond to a pre-GRASP construct and a post-GRASP construct, respectively, in the dual-eGRASP system according to one embodiment of the present disclosure.

The "first labeling material" is introduced into the first cell, and may generate a signal when it is adjacent to or combined with the second labeling material. According to one embodiment of the present disclosure, the first labeling material may be a fluorescent material selected from commonly used fluorescent materials (small-molecule compounds and proteins), and the signal may be a fluorescent signal. In one example, the first labeling material may be introduced into the first cell, and may generate a fluorescent signal when it is adjacent to or combined with the second labeling material.

According to one embodiment of the present disclosure, the first labeling material may comprise (1) a part of a fluorescent protein. Alternatively, the first labeling material may comprise (2) a gene encoding a part of the fluorescent protein. Alternatively, the first labeling material may comprise (3) a vector including a gene encoding a part of the fluorescent protein. In one example, the first labeling material may be introduced and expressed in the first cell by the gene or a vector containing the gene.

The "second labeling material" is introduced into the second cell, and may generate a signal when it is adjacent to or combined with the first labeling material. According to one embodiment of the present disclosure, the second labeling material may be a fluorescent material selected from commonly used fluorescent materials (small-molecule compounds and proteins), and the signal may be a fluorescent signal. In one example, the second labeling material is introduced into the second cell, and may generate a fluorescent signal when it is adjacent to or combined with the first labeling material.

According to an embodiment of the present disclosure, the second labeling material may comprise (1) the remaining part except a part of the fluorescent protein contained in the first labeling material, or a part of the remaining parts. Alternatively, the second labeling material may comprise (2) the remaining part except a part of the fluorescent protein contained in the first labeling material, or a gene encoding a part of the remaining parts. Alternatively, the second labeling material may comprise (3) the remaining part except a part of the fluorescent protein contained in the first labeling material, or a vector including a gene encoding a part of the remaining parts. In one example, the second labeling material may be introduced and expressed in the first cell by the gene or a vector including the gene.

When the first labeling material and the second labeling material are adjacent to each other, they can be bound to generate a signal. Specifically, the first labeling material comprises (1) a part of a fluorescent protein, (2) a gene encoding a part of the fluorescent protein, or (3) a vector including a gene encoding a part of the fluorescent protein, and the second labeling material comprises (1) the remaining part except a part of the fluorescent protein contained in the first labeling material, or a part of the remaining parts, (2) the remaining part except a part of the fluorescent protein contained in the first labeling material, or a gene encoding a part of the remaining parts, or (3) the remaining part except a part of the fluorescent protein contained in the first labeling material, or a vector including a gene encoding a part of the remaining parts, and when the first labeling material and the second labeling material are adjacent to each other, they may be bound to each other to generate a fluorescent signal.

The signal generated by mutually binding the first labeling material or the second labeling material may be a fluorescent signal by a fluorescent protein, and the fluorescent protein may be at least one selected from the group consisting of green fluorescent protein (GFP), mutant green fluorescent protein (mutant GFP), mutant green fluorescent protein with enhanced fluorescence intensity, yellow fluorescent protein (YFP), and cyan fluorescent protein (CFP), but is not limited thereto.

For example, the first labeling material comprises strands S1-S10 of the mutant green fluorescent protein, and the second labeling material comprises strand S11 of the mutant green fluorescent protein, so that it can exhibit a strong green fluorescence when the first labeling material and the second labeling material are adjacent to each other. In one example, the first labeling material may comprise (1) a polypeptide comprising the amino acid sequence of SEQ ID NO: 2, (2) a gene encoding a polypeptide comprising the amino acid sequence of SEQ ID NO: 2, or (3) a vector including a gene encoding a polypeptide comprising the amino acid sequence of SEQ ID NO: 2. In one example, the second labeling material may comprise (1) a polypeptide comprising the amino acid sequence of SEQ ID NO: 5, (2) a gene encoding a polypeptide comprising the amino acid sequence of SEQ ID NO: 5, or (3) a vector comprising a gene encoding a polypeptide comprising the amino acid sequence of SEQ ID NO: 5. SEQ ID NO: 2 represents the amino acid sequence of the strands S1 to S10 (strands S1-S10) of the mutant green fluorescent protein having the S72A mutation in the wild-type green fluorescent protein (a mutant in which serine, which is the 72nd amino acid based on the sequence of general wild-type GFP, is substituted with alanine), and in SEQ ID NO: 2 of Table 1, the green fluorescent protein-specific S72A mutation with enhanced fluorescence intensity is indicated by an underline. FIG. 5c shows that GRASP signal is increased when an additional mutation of S72A occurs in strands 1-10 of the isolated GFP.

For example, the first labeling material comprises strands S1-510 of cyan fluorescent protein, and the second labeling material comprises strand S11 of cyan fluorescent protein, so that it can exhibit a cyan fluorescence when the first labeling material and the second labeling material are adjacent to each other. In one example, the first labeling material may comprise (1) a polypeptide comprising the amino acid sequence of SEQ ID NO: 3, (2) a gene encoding a polypeptide comprising the amino acid sequence of SEQ ID NO: 3, or (3) a vector including a gene encoding a polypeptide comprising the amino acid sequence of SEQ ID NO: 3. In one example, the second labeling material may comprise (1) a polypeptide comprising the amino acid sequence of SEQ ID NO: 5, (2) a gene encoding a polypeptide comprising the amino acid sequence of SEQ ID NO: 5, or (3) a vector including a gene encoding a polypeptide comprising the amino acid sequence of SEQ ID NO: 5. SEQ ID NO: 3 represents the amino acid sequence of strands S1-S10 of the cyan fluorescent protein further having: T65S mutation (mutation in which threonine, which is the 65th amino acid based on the sequence of a common wild-type GFP, is substituted with serine), Y66W mutation (mutation in which tyrosine, which is the 66th amino acid based on the sequence of a common wild-type GFP, is substituted with tryptophan), H148G mutation (mutation in which histidine, which is the 148th amino acid based on the sequence of a common wild-type GFP, is substituted with glycine), and T205S mutation (mutation in which threonine, which is the 205th amino acid based on the sequence of a common wild-type GFP, is substituted with serine), in addition to S72A mutation in a wild-type green fluorescent protein. In SEQ ID NO: 3 of Table 1, the cyan fluorescent protein-specific T65S mutation, Y66W mutation, H148G mutation, and T205S mutation are indicated by an underline.

For example, the first labeling material comprises strands S1-S10 of yellow fluorescent protein, and the second labeling material comprises strand S11 of yellow fluorescent protein, so that it can exhibit yellow fluorescence when the first labeling material and the second labeling material are adjacent to each other. In one example, the first labeling material may comprise (1) a polypeptide comprising the amino acid sequence of SEQ ID NO: 4, (2) a gene encoding a polypeptide comprising the amino acid sequence of SEQ ID NO: 4, or (3) a vector including a gene encoding a polypeptide comprising the amino acid sequence of SEQ ID NO: 4. In one example, the second labeling material may comprise (1) a polypeptide comprising the amino acid sequence of SEQ ID NO: 5, (2) a gene encoding a polypeptide comprising the amino acid sequence of SEQ ID NO: 5, or (3) a vector including a gene encoding a polypeptide comprising the amino acid sequence of SEQ ID NO: 5. SEQ ID NO: 4 shows the amino acid sequence of strands S1-510 of the yellow fluorescent protein further having T203Y mutation (mutation in which threonine, which is the 203th amino acid based on the sequence of a common wild-type GFP, is substituted with tyrosine) in addition to S72A mutation in the wild-type green fluorescent protein. In SEQ ID NO: 4 of Table 1, the yellow fluorescent protein-specific T203Y mutation is indicated by an underline.

TABLE 1

| Category | Sequence | SEQ ID NO: |
|---|---|---|
| Secretory signal peptide | METDTLLLWVLLLWVPGSTGDAPV | 1 |
| Green strands 1-10 | SKGEELFTGVVPILVELDGDVNGHKFSV RGEGEGDATIGKLTLKFICTTGKLPVPW PTLVTTLTYGVQCFARYPDHMKRHDFF KSAMPEGYVQERTISFKDDGKYKTRAV VKFEGDTLVNRIELKGTDFKEDGNILGH KLEYNFNSHNVYITADKQKNGIKANFTV RHNVEDGSVQLADHYQQNTPIGDGPVL LPDNHYLSTQTVLSKDPNEK | 2 |
| Cyan strands 1-10 | SKGEELFTGVVPILVELDGDVNGHKFSV RGEGEGDATIGKLTLKFICTTGKLPVPW PTLVTTLSWGVQCFARYPDHMKRHDFF | 3 |

TABLE 1-continued

| Category | Sequence | SEQ ID NO: |
|---|---|---|
| | KSAMPEGYVQERTISFKDDGKYKTRAV<br>VKFEGDTLVNRIELKGTDFKEDGNILGH<br>KLEYNFNSGNVYITADKQKNGIKANFTV<br>RHNVEDGSVQLADHYQQNTPIGDGPVL<br>LPDNHYLSTQSVLSKDPNEK | |
| Yellow strands 1-10 | SKGEELFTGVVPILVELDGDVNGHKFSV<br>RGEGEGDATIGKLTLKFICTTGKLPVPW<br>PTLVTTLTYGVQCFARYPDHMKRHDFF<br>KSAMPEGYVQERTISFKDDGKYKTRAV<br>VKFEGDTLVNRIELKGTDFKEDGNILGH<br>KLEYNFNSHNVYITADKQKNGIKANFTV<br>RHNVEDGSVQLADHYQQNTPIGDGPVL<br>LPDNHYLSYQTVLSKDPNEK | 4 |
| Common strand 11 | RDHMVLHEYVNAAGIT | 5 |
| Abl SH3-binding peptide (p30) | APTKPPPLPP | 6 |
| Abl SH3-binding peptide (p32) | SPSYSPPPPP | 7 |
| Abl SH3 domain | NDPNLFVALYDFVASGDNTLSITKGEKL<br>RVLGYNHNGEWCEAQTKNGQGWVPS<br>NYITPVNS | 8 |
| neurexin 1b | EVPSSMTTESTATAMQSEMSTSIMETT<br>TLATSTARRGKPPTKEPISQTTDDILVA<br>SAECPSDDEDIDPCEPSSGGLANPTRV<br>GGREPYPGSAEVIRESSSTTGMVVGIV<br>AAAALCILILLYAMYKYRNRDEGSYHVD<br>ESRNYISNSAQSNGAVVKEKQPSSAKS<br>ANKNKKNKDKEYYV | 9 |
| neuroligin1 | LELVPHLHNLNDISQYTSTTTKVPSTDIT<br>LRPTRKNSTPVTSAFPTAKQDDPKQQP<br>SPFSVDQRDYSTELSVTIAVGASLLFLNI<br>LAFAALYYKKDKRRHDVHRRCSPQRTT<br>TNDLTHAPEEEIMSLQMKHTDLDHECE<br>SIHPHEVVLRTACPPDYTLAMRRSPDDI<br>PLMTPNTITMIPNTIPGIQPLHTFNTFTG<br>GQNNTLPHPHPHPHSHS | 10 |

According to still another embodiment of the present disclosure, the first labeling material or the second labeling material may further comprise a first binding-enhancing site or a second binding-enhancing site, respectively. Specifically, when the first labeling material and the second labeling material are located in close proximity, the first labeling material and the second labeling material are bound to each other to generate a signal. In order to assist the binding, the first labeling material and the second labeling material may further comprise a first binding-enhancing site and a second binding-enhancing site, respectively. The first binding-enhancing site and the second binding-enhancing site may form a binding with each other. Therefore, when the first labeling material and the second labeling material are adjacent to each other, the first binding-enhancing site and the second binding-enhancing site are bound to assist the binding of the first labeling material and the second labeling material. For example, referring to FIG. 5a, the upper figure of FIG. 5a shows the results when either post-mGRASP or mCherry-binding pre-mGRASP co-expressing mTagBFP2 was transduced into HEK293T cells through nucleofection, respectively. The interface between mCherry-positive cells and mTagBFP2-positive cells showed faint GRASP signals. On the other hand, the lower figure of FIG. 5a shows the result when either post-eGRASP (SH3-S11-Nlg) co-expressed with iRFP670 or (S1-10)-p40-Nrx co-expressed with mCherry was transduced into HEK293T cells through nucleofection. Peptide p40 (APTYSPPPPP) was bound to a SH3 domain in the post-eGRASP structure to potentiate GRASP signals, and the interface between mCherry-positive cells and iRFP670-positive cells shows strong GRASP signals.

According to an embodiment of the present disclosure, the first binding-enhancing site and the second binding-enhancing site may be Abl SH3 binding peptide or Abl SH3 peptide, respectively. In one example, the Abl SH3 binding peptide may be at least one selected from the group consisting of p32, p30, p41, p40, p8, and 3BP-1. In one example, the first binding-enhancing site may be a polypeptide having an amino acid sequence of SEQ ID NO: 6 or SEQ ID NO: 7. In one example, the second binding-enhancing site may be a polypeptide having an amino acid sequence of SEQ ID NO: 8.

The first binding-enhancing site and the second binding-enhancing site may determine the strength of the bonding force depending on the purpose. For example, when an experiment is designed so that the first labeling material is continuously expressed, the first labeling material may comprise a binding-enhancing site which forms a weaker bond. For example, when an experiment is designed so that the first labeling material is expressed from a specific time zone, the first labeling material may comprise a binding-enhancing site which forms a stronger bond. In one example, when the first labeling material is continuously expressed, it is designed to comprise p30 as the first binding-enhancing site, and when the first labeling material is expressed from a specific time zone, it is designed to comprise p32 as the first binding-enhancing site, thereby appropriately adjusting the balance of signal or fluorescence intensity (FIG. 5b).

According to another embodiment of the present disclosure, the first labeling material and the second labeling material may further comprise a secretory signal peptide and/or a cellular transmembrane region, respectively. The secretory signal peptide performs the function of directing the first labeling material and the second labeling material to the outside of the cell membrane. The cellular transmembrane region performs a function that allows the first labeling material and the second labeling material to be located through the cell membrane of the first cell and the second cell.

For example, the secretory signal peptide may be at least one selected from the group consisting of IgG kappa signal peptide, SAP1 signal peptide, BiP1 signal peptide, ARS1 signal peptide, and CAH1 signal peptide. In one example, the secretory signal peptide may be a peptide having the amino acid sequence of SEQ ID NO: 1.

For example, the cellular transmembrane region may comprise at least one selected from the group consisting of a transmembrane region of neuroligin1, a stalk of neurexin 1b, a transmembrane region of neurexin 1b, an intracellular region of neurexin 1b, a transmembrane region of M2, a transmembrane region of Kdpf, a transmembrane region of CorA, and a transmembrane region of PDGFR. In one example, the cellular transmembrane region may be a peptide having an amino acid sequence of SEQ ID NO: 9 or SEQ ID NO: 10.

According to another embodiment of the present disclosure, the first labeling material may comprise (1) a polypeptide comprising the amino acid sequence of SEQ ID NO: 2, SEQ ID NO: 3, or SEQ ID NO: 4, (2) a gene encoding a polypeptide comprising the amino acid sequence of SEQ ID NO: 2, SEQ ID NO: 3, or SEQ ID NO: 4, or (3) a vector including a gene encoding a polypeptide comprising the amino acid sequence of SEQ ID NO: 2, SEQ ID NO: 3, or SEQ ID NO: 4.

The polypeptide contained in the first labeling material or encoded by the first labeling material may further comprise at least one selected from the group consisting of an amino acid sequence of SEQ ID NO: 1, an amino acid sequence of SEQ ID NO: 6, an amino acid sequence of SEQ ID NO: 7, an amino acid sequence of SEQ ID NO: 8, an amino acid sequence of SEQ ID NO: 9, and an amino acid sequence of SEQ ID NO: 10. For example, the polypeptide contained in the first labeling material or encoded by the first labeling material may further comprise (1) at least one selected from the group consisting of SEQ ID NO: 2 to SEQ ID NO: 4, (2) at least one selected from the group consisting of SEQ ID NO: 6 to SEQ ID NO: 8, and/or (3) at least one amino acid sequence selected from the group consisting of SEQ ID NO: 9 to SEQ ID NO: 10. In one example, the polypeptide contained in the first labeling material or encoded by the first labeling material may have or comprise at least one amino acid sequence selected from the group consisting of SEQ ID NOs: 11 to 13.

According to another embodiment of the present disclosure, the second labeling material may comprise (1) a polypeptide comprising the amino acid sequence of SEQ ID NO: 5, (2) a gene encoding a polypeptide comprising the amino acid sequence of SEQ ID NO: 5, or (3) a vector including a gene encoding a polypeptide comprising the amino acid sequence of SEQ ID NO: 5.

The polypeptide contained in the second labeling material or encoded by the second labeling material may further comprise an amino acid sequence of SEQ ID NO: 1, an amino acid sequence of SEQ ID NO: 6, an amino acid sequence of SEQ ID NO: 7, an amino acid sequence of SEQ ID NO: 8, an amino acid sequence of SEQ ID NO: 9, and an amino acid sequence of SEQ ID NO: 10. For example, the polypeptide contained in the second labeling material or encoded by the second labeling material may further comprise (1) SEQ ID NO: 5, (2) at least one selected from the group consisting of SEQ ID NO: 6 to SEQ ID NO: 8, and/or (3) at least one amino acid sequence selected from the group consisting of SEQ ID NO: 9 to SEQ ID NO: 10. In one example, the polypeptide contained in the second labeling material or encoded by the second labeling material may have or comprise the amino acid sequence of SEQ ID NO: 14.

According to another embodiment of the present disclosure, the first labeling material may be at least two types of labeling materials that are different from each other, and the two or more first labeling materials may generate mutually different fluorescent signals. For example, the first labeling material may be two or more labeling materials that generate mutually different fluorescent signals.

For example, the first labeling material may comprise (1) a part of at least two types selected from the group consisting of green fluorescent protein (GFP), mutant green fluorescent protein (mutant GFP), mutant green fluorescent protein with enhanced fluorescence intensity, yellow fluorescent protein (YFP), and cyan fluorescent protein (CFP), (2) a gene encoding a part of the selected at least two types, or (3) a vector including a gene encoding a part of the selected at least two types. For example, the first labeling material may comprise (1) two or more types of polypeptides selected from the group consisting of a polypeptide having an amino acid sequence of SEQ ID NO: 11, a polypeptide having an amino acid sequence of SEQ ID NO: 12, and a polypeptide having an amino acid sequence of SEQ ID NO: 13, (2) two or more types of genes encoding the selected two or more types of polypeptides, or (3) two or more types of vectors including genes encoding the selected two or more types of polypeptides.

When the first labeling material is two or more types that generate different signals, it can be distinguished according to the type of pre-synaptic neurons among numerous synapses by a distinguishable signal, for example, by light of a distinguishable wavelength, and can be used to confirm which mechanism forms a synapse.

According to another embodiment of the present disclosure, the first labeling material is introduced into the first cell, and the first labeling material may be operably linked to an activity-dependent promoter. The first labeling material may comprise a gene encoding a part of the fluorescent protein, or a vector including a gene encoding a part of the fluorescent protein. For example, the first labeling material may be introduced into the first cell by being operably linked to a gene encoding a part of the fluorescent protein by an activity-dependent promoter. The details concerning the fluorescent protein or a part of the fluorescent protein is as described above.

When the first labeling material is operably linked to an activity-dependent promoter, the point of time when the first labeling material is activated or expressed can be arbitrarily adjusted, and therefore, it can be utilized to confirm proximity or contact between the first cell and the second cell formed from a specific point of time. For example, to distinguish presynaptic cells involved in memory formation, when the activity dependent promoter is initiated at the point of time of forming a specific memory to thereby activate or express the first labeling material, it can be distinguished or determined that presynaptic cells in which signal or fluorescence by the binding of the first labeling material and the second labeling material are detected are memory storing cells involved in the formation of a specific memory, that is, engram cells.

According to another embodiment of the present disclosure, a gene encoding the first labeling material or the second labeling material is introduced into the first cell or the second cell, respectively, and the gene introduced into the first cell or the second cell may be operably linked to a promoter. For example, the gene encoding the first labeling material or the second labeling material may be operably linked to a CaMKII promoter, an EF1a promoter, a CMV promoter, a trp promoter, a lac promoter, a tac promoter, a T7 promoter, a metallothionein promoter, an adenovirus late promoter, a vaccinia virus 7.5K promoter, a SV40 promoter, a cytomegalovirus promoter, a HSV-tk promoter, and the like.

According to another embodiment of the present disclosure, the first labeling material is two or more types that are different from each other, and genes encoding each of the two or more types of the first labeling material are introduced into the first cell, and at least one of the genes introduced into the first cell may be operably linked to a activity-dependent promoter. In this case, the first labeling material operably linked to a promoter having no activity dependency (hereinafter, "first labeling material having no activity-dependency") is allowed to be continuously expressed, and the first labeling material operably linked to a promoter having an activity dependence (hereinafter, "first labeling material having activity-dependency") is regulated to be expressed at a specific point of time, thereby further increasing the accuracy of confirming proximity or contact between the first cell and the second cell formed from a specific point of time. At this time, the first labeling material having activity dependence and the first labeling material having no activity dependence may be different types of labeling materials. For example, in order to distinguish the synapses of neurons according to the type of presynaptic cells and so distinguish the synapses involved in the memory formation, in a state in which the first labeling material having no activity dependence is continuously expressed, when the activity-dependent promoter (a labeling material different from the first labeling material having no activity dependence) is initiated a the point of time when a specific memory is formed, thereby operating the first labeling material having activity dependence, it can be distinguished or determined that the synapse in which fluorescence is detected due to the binding of the first labeling material and the second labeling material having activity dependence is a memory storing synapse involved in the specific memory formation. It can be distinguished or determined that the synapse in which only fluorescence is detected due to the binding of the first labeling material having no activity dependence (a labeling material different from the first labeling material having activity dependence) and the second labeling material is not involved in the specific memory formation.

According to another embodiment of the present disclosure, the second labeling material is introduced into the second cell, and the second labeling material may be operably linked to an activity-dependent promoter. The second labeling material may comprise a gene encoding the remaining part of the fluorescent protein contained in the first labeling material or expressed by the first labeling material, or a vector including a gene encoding the remaining part of the fluorescent protein contained in the first labeling material or expressed by the first labeling material. For example, the gene encoding the remainder of the fluorescent protein contained in the first labeling material or expressed by the first labeling material is operably linked by an activity-dependent promoter, and thereby, the second labeling material can be introduced into the second cell. The details concerning the fluorescent protein or a part of the fluorescent protein is as described above.

When the second labeling material is operably linked to an activity-dependent promoter, the point of time when the second labeling substance is activated or expressed by using the Tet-On system can be arbitrarily adjusted through intraperitoneal injection of doxycycline, and thus, engram cells that store specific memories can be labeled, and used to differentiate the types of synapses (non-engram to engram (N-E), engram to engram (N-N), engram to non-engram (E-N), and non-engram to non-engram (N-N) synapses). For example, the second labeling material may be designed to be expressed together with a fluorescent protein (e.g., mScarlet-I, iRFP670, etc.) capable of differentiating from fluorescence generated by binding with the first labeling material. In one example, the second labeling material is expressed at two or more gene regions, the second labeling material may be expressed together with a fluorescent protein that is mutually distinguishable, at least one of the gene regions expressing the second labeling material may be operably linked to an activity-dependent promoter. Specifically, referring to FIG. 3a, in the CA1 region into which a vector including a gene encoding the second labeling material is introduced, the second labeling material is expressed at two or more gene regions, and each second labeling material was designed to be expressed together with mScarlet-I or iRFP670. In this case, at least one region (a second labeling material expressed together with mScarlet-I) is operably linked to an activity-dependent promoter (e.g., c-fos in FIG. 3A), and postsynaptic cells involved in the formation of a specific memory can be distinguished and labeled. At this time, when a fluorescent signal designed to be operably linked to an activity-dependent promoter is generated, the postsynaptic cells can be distinguished as engram cells that are involved in the formation of specific memories. In particular, when a signal generated by binding with the first labeling material having activity dependence is generated together, the synapse can be distinguished from engram to engram (E-E) synapse.

Thousands of synapses exist in one neuron. Since synapse is the smallest functional unit of the nervous system, studying at the synapse level is important. However, until now, it was impossible to classify the synapses of one neuron according to presynaptic cells. By using the dual-eGRASP system according to an embodiment of the present disclosure, synapses of one neuron can be distinguished according to the type of presynaptic cells. For example, by using the present disclosure, it is possible to distinguish synapses in one neuron receiving input from different brain regions, which was impossible in the past, thus comparing and analyzing its function and location distribution, to distinguish synapses in one neuron receiving input from different cell types, thus comparing and analyzing its function and location distribution, or to distinguish synapses in one neuron receiving input from cells showing different activities, thus comparing and analyzing its function and location distribution, or the like. In addition, the degree and intensity of the expression may be greatly affected by the virus injection surgery deviation for expressing the first labeling material, which can affect the interpretation of the results. However, using two or more colors (fluorescence) has an effect capable of being used as an internal control.

The activity-dependent promoter may be at least one selected from the group consisting of fos promoter, Fos-rtTA, Fos-creERT2, Arc promoter, and the other immediate early gene promoters. The activity-dependent promoter may be operated by doxycycline or tamoxifen. Specifically, the activity-dependent promoter expresses a transcription factor, and the transcription factor may activate a drug-dependent promoter. For example, the activity-dependent promoter expresses rtTA (reverse tTA), and the drug-dependent promoter may operate in the presence of a specific drug by the rtTA. The drug-dependent promoter may be tetO promoter (operates to be dependent on doxycycline), or EF1a-DIO-promoter (expression is induced by creERT2 which is dependently activated by tamoxifen). In one example, the activity-dependent promoter expresses rtTA that operates the drug-dependent promoter, and the drug-dependent promoter (e.g., TRE3G) may be operated by the rtTA in the presence of doxycycline, so that the activity-dependent promoter may be operated in the presence of doxycycline. Alternatively, the drug-dependent promoter (e.g., EF1a-DIO-promoter), expression of the DIO sequence is induced by Cre recombinase (creERT2) which is activated in the presence of tamoxifen, and the activity-dependent promoter may be operated in the presence of tamoxifen.

According to another embodiment of the present disclosure, there is provided a method of confirming a memory storage synapse comprising: a step of introducing a gene being initiated with an activity-dependent promoter and encoding a first labeling material into a presynaptic neuron, and introducing a gene encoding the second labeling material into a postsynaptic neuron; and a step of detecting a signal by the binding of the first labeling material and the second labeling material.

The method of confirming the memory storage synapse may, after the introducing step, further comprise a step of operating the activity-dependent promoter; and a step of forming a specific memory.

The method of confirming the memory storage synapse may, after the step of detecting the signal, further comprise a step of determining a pre-synaptic neuron in which the signal is generated as an engram cell involved in the formation of the specific memory.

For example, the method of confirming the memory storage synapse may comprise: a step of introducing a gene being initiated with an activity-dependent promoter and encoding a first labeling material into a presynaptic neuron, and introducing a gene encoding the second labeling material into a post-synaptic neuron; a step of operating the activity-dependent promoter; a step of forming a specific memory; a step of detecting a signal by the binding of the first labeling material and the second labeling material; and a step of determining the presynaptic neuron in which the signal is generated as the memory storage cell (Engram Cell) involved in the formation of the specific memory.

The first labeling material, the second labeling material, the first cell, the second cell, the signal, the fluorescent protein, a part of the fluorescent protein, or an activity-dependent promoter are as described above.

The method of confirming the memory storage synapse may be performed in animals, fish, amphibians, reptiles, birds, mammals, rats, mice, guinea pigs, hamsters, primates, dogs, rats, sheep, cow, chicken, horses, monkeys, gorilla, human, mammals except humans, or primates except humans According to another embodiment of the present disclosure, there is provided a composition for detecting an intercellular proximity comprising: a first labeling material including a part of a fluorescent protein, a gene encoding a part of the fluorescent protein, or a vector including a gene encoding a part of the fluorescent protein; and a second labeling material including the other part of the fluorescent protein, a gene encoding the other part of the fluorescent protein, or a vector including a gene encoding the other part of the fluorescent protein.

According to another embodiment of the present disclosure, there is provided an animal comprising: a first cell into which a gene encoding a first labeling material has been introduced, and a second cell into which the gene encoding the second labeling material has been introduced, wherein the first labeling material and the second labeling material are bound to each other to generate a signal.

The animal may be a non-naturally occurring transgenic animal, and may be animals except humans, mammals except humans, primates except humans, mammals, primates, rodent, mouse, rats, hamsters, guinea pigs, monkeys, gorilla, for example animals except humans.

According to another embodiment of the present disclosure, there is provided a method of preparing an animal model comprising the steps of: introducing a gene encoding a first labeling material into a first cell of the animal, and introducing a gene encoding a second labeling material into a second cell of the animal, wherein the first labeling material and the second labeling material are bound to each other to generate a signal.

Advantageous Effects

The present disclosure provides an eGRASP technique that examines synapses between neurons of a brain by using a recombinant fluorescent protein that enhances fluorescence intensity and can distinguish by two or more colors, and furthermore, can distinguish the types of presynaptic neurons of numerous synapses present in neurons. In addition, it provides a method of analyzing synaptic correlation related to the memory formation using the eGRASP technique.

BRIEF DESCRIPTION OF THE DRAWINGS

FIG. 1a to FIG. 1e show the results of experiments differentiating two population of synapses on a single neuron using Dual-eGRASP of the present disclosure. FIG. 1a shows a schematic illustration of cyan and yellow eGRASP. Common post-eGRASP is expressed in a single postsynaptic cell, whereas cyan pre-eGRASP and yellow pre-EGRASP are expressed in two different presynaptic populations.

FIG. 1b shows photographs of co-expression of either cyan or yellow pre-eGRASP with post-eGRASP and iRFP670 in HEK293T cells.

FIG. 1c shows three populations of HEK293T cells separately transduced using nucleofection. One population expresses cyan pre-eGRASP and mCherry, another population expresses yellow pre-eGRASP and mCherry, and the third population expresses post-eGRASP and iRFP670.

FIG. 1d shows that cyan pre-eGRASP and yellow pre-eGRASP are expressed in the LEC and MEC, respectively. Post-eGRASP is expressed together with myristoylated TagRFP-T (myr_TagRFP-T) in the DG.

FIG. 1e shows that cyan pre-eGRASP and yellow pre-eGRASP are expressed in the right CA3 and left CA3, respectively. Post-eGRASP was expressed together with myrTagRFP-T in CA1.

FIGS. 2a to 2e show the results of experiments confirming that the synapse from the CA3 engram toward the CA1 engram exhibits a higher synaptic density and a larger spine size after memory formation. The left figure of FIG. 2a shows a schematic illustration of the injected AAV, the middle figure shows the location of virus injection, and injections at each location consisted of the final mixture of virus injected at each location. The right figure shows a schematic illustration of the experimental method.

The left figure of FIG. 2b shows a schematic illustration of four synaptic groups that can occur between engrams and non-engram cells. The right figure shows the classification of four synaptic groups recognized by four colors. Cyan represents N-N, orange represents E-N, blue represents N-E, and red represents E-E. The colors of each group were applied to FIGS. 2 and 3.

FIG. 2c shows a representative diagram of an actual confocal fluorescence image and 3D modeling.

FIG. 2d shows the results of normalized cyan/yellow eGRASP per dendritic length. The densities of cyan-only (left) or yellow puncta (right) on red dendrites are normalized to the corresponding cyan-only or yellow puncta on near-infrared dendrites from same images in order to exclude the effect of different number of CA3 cells expressing respective presynaptic components. Each data point represents a dendrite. N=43 for CA1 non-engram dendrites; n=45 for CA1 engram dendrites; 9 images from 3 mice. Mann Whitney two-tailed test, n.s.: not significant, **p=0.0017.

FIG. 2e shows normalized spine head diameters and spine volumes together with a schematic illustration. The left-hand side shows dendrites of CA1 non-engram cells, and the right-hand side shows the dendrites from engram cells. Sizes of the spines with yellow puncta of the same were normalized to those of the spines with cyan-only puncta of the same dendrites. Each data point represents a spine. N-N, n=81; E-N, n=107; N-E, n=93; E-E, n=55, Mann Whitney two-tailed test, n.s.: not significant, p=0.0014, **p<0.0001. Data are expressed as mean±SEM.

FIGS. 3a to 3f show the results of experiments confirming that the synaptic connectivity between pre- and post-synaptic engram cells is proportional to the memory strength. FIG. 3a shows a schematic illustration of injected AAVs, virus injection location, and experimental protocol.

FIG. 3b shows a schematic illustration of contextual fear conditioning and memory retrieval process.

FIG. 3c shows the results of one-way ANOVA and Tukey test for multiple comparison under fear response level, context n=6, weak shock n=5, strong shock n=5 of each group. F(2,13)=15.85, *p<0.05, ***p<0.001.

FIG. 3d is a schematic illustration of hypothesized results showing higher density of E-E synapses with increasing memory strength.

FIG. 3e shows the synaptic density of each connection. n=74, context N-N; n=67, context N-E; n=79, weak shock N-N; n=80, weak shock N-E; n=92, strong shock N-N; n=91, strong shock N-E; n=74, context E-N; n=67, context E-E; n=79, weak shock E-E; n=80, weak shock E-N; n=92, strong shock E-E; n=91, strong shock E-N. 15 images were obtained from 6 mice for the group exposed only to the context, 16 images from 5 mice for the group that received a weak shock, and 19 images from 5 mice for the group that received a strong shock. Mann Whitney two-tailed test, n.s.: not significant, *p<0.05, p<0.01, *p<0.001, ****p<0.0001.

FIG. 3f shows spine head diameters of each connection. n=107, context N-N; n=64, context E-N; n=72, weak shock N-N; n=34, weak shock E-N; n=112, strong shock N-N; n=46, strong shock E-N; n=103, context N-E; n=77, context E-E; n=85, weak shock N-E; n=84, weak shock E-E; n=57, strong shock N-E; n=110, strong shock E-E. Six mice for the group exposed only to the context, five mice for the group exposed to a weak shock, and five mice for the group exposed to a strong shock were used. Mann Whitney two-tailed test, n.s.: not significant, *p<0.05, p<0.01, *p<0.001, ****p<0.0001. The result values were expressed as mean±SEM.

FIG. 4a shows the improved synaptic transmission between CA3 engram and CA1 engram cells through pre- and post-synaptic mechanisms. The left-hand side of FIG. 4a shows a schematic illustration of injected AAVs, and the right-hand side shows illustration of virus injection sites and experimental protocol.

The left figure of FIG. 4B is diagram of whole cell-cell recording experiments, the right figure shows the classification of four synaptic populations indicated by four colors. Cyan, T-N; orange, E-N; blue, T-E; red, E-E. The color for each group applies to FIG. 4.

FIG. 4c shows the tracking results from PPR recordings.

FIG. 4d shows the results from PPR recordings. T-N, n=11; T-E, n=10; E-N, n=11; E-E, n=12.

FIG. 4e shows the average PPR at the indicated inter-stimulus intervals. *p<0.05, p<0.01, *p<0.001, Tukey's multiple comparison test after one-way ANOVA; (25 ms) F(3,40)=8.259, *p=0.0276; (50 ms) F(3,40)=7.989, *p=0.0003; (75 ms) F(3,40)=7.517, *p=0.0004.

FIG. 4f shows the results of tracking mEPSCs induced with $Sr^{2+}$ light. Arrows indicate discontinuous release phenomena.

FIG. 4g shows the average amplitude of $Sr^{2+}$ light-evoked mEPSCs. T-N, n=15; T-E, n=18; E-N, n=12; E-E, n=13; p<0.01, Tukey's multiple comparison test after one-way ANOVA, F(3,54)=8.540, *p<0.0001.

FIG. 4h shows the results of pairing LTP with stimulus given after 5 minutes of baseline recording. T-N, n=14; T-E, n=10; E-N, n=11; E-E, n=9.

FIG. 4i shows the results of average EPSC amplitude of the last 5 min of recording. *p<0.05, Tukey's multiple comparison test after one-way ANOVA. F(3,40)=3.683, *p=0.0197. The result values were expressed as mean±SEM.

FIG. 5 shows the experimental results confirming the effect of improving the GRASP signal. The upper figure of FIG. 5a is a result when either post-mGRASP or mCherry-binding pre-mGRASP co-expressing mTagBFP2 was transduced into HEK293T cells through nucleofection. The interface between mCherry-positive cells and mTagBFP2-positive cells showed only faint GRASP signals, which were detectable only in stronger release. The lower figure shows the result when either post-eGRASP (SH3-S11-Nlg) co-expressed with iRFP670 or (S1-10)-p40-Nrx co-expressed with mCherry was transduced into HEK293T cells through nucleofection. Peptide p40 (APTYSPPPPP) was bound to a SH3 domain in the post-eGRASP structure to enhance GRASP signals. The interface between mCherry-positive cells and iRFP670-positive cells shows strong GRASP signals.

FIG. 5b shows a remarkable GRASP signal compared to mGRASP when the SH3 binding peptide is changed to have low binding strength, but shows the result that the GRASP signal is reduced. The dissociation constant of each peptide for SH3 domain was indicated under each peptide.

FIG. 5c shows that when an additional mutation of S72A occurs in 1-10 strands of the isolated GFP, the GRASP signal increases.

The upper figure of FIG. 5d shows that pre-mGRASP was expressed in CA3 and post-mGRASP with the membrane target TagRFP-T was rarely expressed in CA1. The lower figure shows that pre-eGRASP with the weakest binding peptide (p30) was expressed in CA3, and post-eGRASP with the membrane target TagRFP-T is rarely expressed in CA1. mGRASP signal was not detected in this experimental condition, and the eGRASP signal was clearly visible in the CA1 dendrite spine even to the weakest binding peptide.

FIG. 6a shows the pre-eGRASP results for the indicated mutations when post-eGRASP and iRFP670 are co-expressed in HEK293T cells. Pre-eGRASP with T65S, Y66W, S72A, H148G and T205S shows the brightest cyan fluorescence.

FIG. 6b shows pre-eGRASP results for the indicated mutations in which post-eGRASP and iRFP670 were co-expressed in HEK293T cells. Pre-eGRASP containing S72A and T203Y showed bright signals in both GFP and YFP filters, but not in CFP filters. The original pre-eGRASP showed a signal when all filters were used, and showed the brightest in GFP filter. This result showed that the T203Y mutation showed a red shifted fluorescence separable from the CFP signal.

FIGS. 7a to 7c are views confirming that the expression of the dual-eGRASP components does not affect basic synaptic transmission, and FIG. 7a shows the tracking results from representative miniature EPSC (mEPSC) recordings. FIGS. 7b and 7c show the amplitude and frequency of mEPSCs of CA1 pyramidal neurons in fragments expressing eGRASP components in the CA3 and CA1 as indicated, respectively. No eGRASP (no eGRASP component in both CA3 and CA1), n=12; Post eGRASP (post-eGRASP in CA1), n=10; Pre eGRASP (pre-eGRASP in CA3), n=12; Pre-Post eGRASP (pre-eGRASP in CA3d and post-eGRASP in CA1), n=11. One-way ANOV of amplitude, n.s.: not significant, $F(3,41)=1.074$, $p=0.3705$. One-way ANOVA of frequency, n.s.: not significant, $F(3,41)=2.167$, $p=0.1065$. The result values were expressed as mean±SEM.

FIGS. 8a to 8c show the results of validation experiments of the Fos-rtTA system with seizures. FIG. 8a is a schematic illustration of the injected AAV, in which the nuclear target mEmerald (mEmerald-Nuc) was regulated by the TRE3G promoter that were regulated by rtTA3G expressed by the Fos promoter, and the nuclear target mCherry regulated by CaMKIIα was used for an expression control.

FIG. 8b is a diagram showing a timetable of actions used in the experiments.

FIG. 8c is a diagram showing that injection of seizure-induced Pentylenetetrazol (PTZ) induces a strong mEmerald-Nuc signal in DG.

FIGS. 9a to 9d show the results of verification experiments of the Fos-rtTA system using CFC. FIG. 9a shows a schematic illustration of the injected AAV.

FIG. 9b is a diagram showing a timetable of actions used in the experiments.

FIG. 9c is a representative diagram showing that the activity-dependent promoter operates well.

FIG. 9d is a diagram showing that CA3 induces a significant increase in mEmerald-Nuc under contextual fear conditioning and shows the tendency to strongly increase in CA1. n=6, CA3 Homecage; n=5, CA3 Conditioned; n=8, CA1 Homecage; n=5, CA1 Conditioned. Unpaired two-tailed t test, **$p<0.01$. The result values were expressed as mean±SEM.

FIGS. 10a and 10b show the results of verification experiments of expression of yellow eGRASP regulated by doxycycline. FIGS. 10a and 10b show representative diagrams of cyan and yellow eGRASP expression in the absence of doxycycline (FIG. 10A) or when doxycycline was injected (FIG. 10B). MyrTagRFP-T-P2A-post-eGRASP as well as cyan pre-eGRASP were also continuously expressed using the DIO/Cre system expressing each component in a random group of CA1 and CA3 neurons, and yellow pre-eGRASP was expressed only in CA3 using the Fos-rtTA system.

FIG. 11 is a table showing the overlapping ratio of the neuron group. According to FIG. 11a, the ratio of cyan signals including the yellow signal in iRFP670 positive dendrites was 40.25%. The ratio of yellow signals including cyan signals in iRFP670 positive dendrites was 78.38%. n=43, 43 iRFP670 dendrites were obtained from 3 mice. According to FIG. 11b, the ratio of cyan signals including yellow signals in mScarlet-I positive dendrites showed 50.00%. The ratio of yellow signals including cyan signals in mScarlet-I positive dendrites was 80.37%. n=45, 45 mScarlet-I dendrites were obtained from 3 mice. According to FIG. 11c, the proportion of iRFP670 positive cells that also express mScarlet-I is 20.93%. The ratio of mScarlet-I positive cells that also express iRFP670 is 11.61%. n=10, ten CA1 cell layer images were obtained from three mice.

FIG. 12 shows the effect of each interaction on the synaptic density. According to FIGS. 12a and 12b, the synaptic density of the N-N synapse is similar to that of the N-E synapse. However, the density of E-E synapse was significantly higher than that of E-N synapse. Each data point represents one dendrite. CA1 non-engram dendrites n=47, CA1 engram dendrites n=64, and 11 images were obtained from 1 mouse. Mann Whitney two-tailed test, n.s.: not significant, **$p<0.0001$. The binding proteins of cyan and yellow eGRASP are all p32. The experimental design was the same as in FIG. 2 except that the red fluorescent protein was TagRFP-T instead of mScarlet-I. According to FIGS. 12c and 12d, the synaptic density of the N-N synapse is similar to that of the N-E synapse. However, the density of E-E synapse was significantly higher than that of E-N synapse. Each data point represents one dendrite. CA1 non-engram dendrites n=116, CA1 engram dendrites n=48, and 9 images were obtained from 1 mouse. Mann Whitney two-tailed test, n.s.: not significant, **$p<0.0001$. The binding peptide of cyan eGRASP was p30, and yellow was p32. The experimental design was shown similar to FIG. 2 except that the red fluorescent protein was TagRFP-T instead of mScarlet-I. The result values were expressed as mean±SEM.

FIG. 13 shows that the number of CA3 and CA1 engram cells appears similar even in the difference in memory strength. According to FIG. 13a, the number of CA1 engram neurons expressing myr-mScarlet-I was shown to be constant among the three populations. Context n=6; weak shock, n=5; strong shock, n=5, one-way ANOVA, n.s.: not significant, $F(2,13)=2.872$, $p=0.0927$. FIG. 13b shows that the number of CA3 engram neurons measured as the ratio of cyan eGRASP signal and yellow eGRASP signal overlapping was constant among the three populations. Context, n=6; weak shock, n=5; strong shock, n=5.one-way ANOVA, n.s.: not significant, $F(2,13)=0.264$, $p=0.7720$. The result values were expressed as mean±SEM.

FIG. 14 shows that the spine volume between the anterior and posterior engram cells is proportional to the memory strength. FIG. 14a shows that the volumes of N-N and E-N spines appear similar in all groups, and FIG. 14b shows that the increase in spine volume of E-E spine through conditioning was significantly higher in the group exposed to only the context and the group receiving a strong shock than the group receiving a weak shock. In FIGS. 14a and 14b, each data point represents one spine. n=107, context N-N; n=64, context E-N; n=72, weak shock N-N; n=34, weak shock E-N; n=112, strong shock N-N; n=46, strong shock E-N; n=103, context N-E; n=77, context E-E; n=85, weak shock N-E; n=84, weak shock E-E; n=57, strong shock N-E; n=110, strong shock E-E. Six mice were used in the group exposed only to the context, 5 mice in the group exposed to the weak shock, and 5 mice in the group exposed to the strong shock. Mann Whitney two-tailed test, n.s.: not significant, *$p<0.05$, $p<0.01$, *$p<0.001$, ****$p<0.0001$. The result values were expressed as mean±SEM.

FIG. 15 is a diagram showing the amino acid sequence of post-eGRASP having the amino acid sequence of SEQ ID NO: 14 according to an embodiment of the present disclosure, and discriminately represents (1) IgG kappa signal peptide (underlined in italics), (2) Abl Sh3 area (indicated in bold and underlined), (3) 11 strands of mutant GFP (indicated in italic and bold and underlined), (4) the stalk, transmembrane, and intracellular regions of neuroligin1 (underlined).

FIG. 16 is a view showing the amino acid sequence of cyan pre-eGRASP having the amino acid sequence of SEQ ID NO: 12 according to an embodiment of the present disclosure, and discriminately represents (1) IgG kappa signal peptide (indicated in italics and underlined), (2) 1-10 strands of GFP with S72A (indicated in bold, underlined, boxed in cyan specific mutations T65S, Y66W, H148G, T205S), (3) p30 (indicated in italic bold and underlined), (4) neurexin 1b's stalk, transmembrane, and intracellular regions (underlined).

FIG. 17 is a view showing the amino acid sequence of Pre-eGRASP (p30) having the amino acid sequence of SEQ ID NO: 11 according to an embodiment of the present disclosure, and discriminately represents (1) IgG kappa signal peptide (underlined in italics), (2) 1-10 strands of GFP with S72A (underlined in bold, indicated by an asterisk in S72A), (3) p30 (indicated in italic bold and underlined), (4) neurexin 1 b's stalk, transmembrane, and intracellular domain (underlined).

FIG. 18 is a diagram showing the amino acid sequence of yellow pre-eGRASP (p30) having the amino acid sequence of SEQ ID NO: 13 according to an embodiment of the present disclosure, and is a diagram discriminately showing (1) IgG kappa signal peptide (indicated in italics and underlined), (2) strand 1-10 containing S72A (indicated in bold, underlined, boxed in the yellow specific mutant T203Y), (3) p30 (indicated in italic bold and underlined), (4) neurexin 1 b's stalk, transmembrane, and intracellular regions (underlined).

FIG. 19 shows a schematic illustration of eGRASP according to an embodiment of the present disclosure.

DETAILED DESCRIPTION OF THE EMBODIMENTS

The storage and retrieval of memories requires a specific neuronal population with increased neuronal activity during memory formation. Several studies have confirmed these engram cells across multiple brain regions and have demonstrated that activated engram cells can induce artificial retrieval of stored memories. To explain how memory is stored in the engram, Donald O. Hebb has presented a hypothesis often expressed as "fire together, wire together". This hypothesis suggests that synaptic potentiation between co-activated neurons forms a neural substrate for memory. However, since it is not possible to distinguish whether the entire synapse derives from engram cells or non-engram cells, it is impossible to explain whether memory formation potentiates synapses between engram cells in connected brain regions.

In order to identify specific nerve regions that serve as memory storage, the present inventors have developed a dual eGRASP technique that examines synapses between engram cells.

Hereinafter, the present disclosure is described in more detail with reference to examples. However, these examples are provided for illustrative purposes only, and the scope of the present disclosure is not limited thereby.

Example 1

Preparation of Pre-eGRASP and Post-eGRASP 1-1. Preparation of Pre-eGRASP

Pre-eGRASP was prepared so as to be composed of (1) IgG kappa signal peptide kSP, (2) strands 1-10 of mutant GFP, (3) Abl SH3 binding peptide, and (4) stalk, transmembrane region and intracellular region of neurexin 1b (see FIG. 19).

(3) Abl SH3 binding peptide contained in Pre-eGRASP had p30 (APTKPPPLPP) or p32 (SPSYSPPPPP) sequence. p32 was bound more strongly to Abl SH3 peptide of post-eGRASP than p30. Therefore, in this example, a cyan pre-eGRASP designed to be continuously expressed was prepared using p30, and in this example, yellow pre-eGRASP designed to start to be expressed from a specific time point when memory starts to be formed was prepared using p32, thereby matching the balance of cyan fluorescence and yellow fluorescence.

Pre-eGRASP added a mutation of S72A (based on the number of amino acids in GFP sequence) of strands 1-10 of GFP to the existing GRASP mutation (see FIG. 17). FIG. 17 shows the amino acid sequence of Pre-eGRASP (p30), and discriminately represents (1) IgG kappa signal peptide (indicated in orange letters), (2) strands 1-10 of GFP with S72A (indicated in green letters, highlighted in S72A with green highlights), (3) p30 (indicated in red letters), (4) stalk, transmembrane, and intracellular domain (indicated in blue letters) of neurexin 1 b. The p32 version is a modification of the sequence of APTKPPPLPP to SPSYSPPPPP. The amino acid sequence of Pre-eGRASP (p30) was shown in Table 2 as SEQ ID NO: 11 (S72A is underlined in bold).

TABLE 2

| Category | Sequence | SEQ ID NO: |
|---|---|---|
| Pre-eGRASP (p30) | METDTLLLWVLLLWVPGSTGDAPVGGSKGEELFTGVVPIL VELDGDVNGHKFSVRGEGEGDATIGKLTLKFICTTGKLPV PWPTLVTTLTYGVQCFARYPDHMKRHDFFKSAMPEGYV QERTISFKDDGKYKTRAVVKFEGDTLVNRIELKGTDFKED GNILGHKLEYNFNSHNVYITADKQKNGIKANFTVRHNVED GSVQLADHYQQNTPIGDGPVLLPDNHYLSTQTVLSKDPN EKTGGSGGSGGSRAPTKPPPLPPGGGSGGGSGTEVPSS MTTESTATAMQSEMSTSIMETTTTLATSTARRGKPPTKEPI SQTTDDILVASAECPSDDEDIDPCEPSSGGLANPTRVGGR EPYPGSAEVIRESSSTTGMVVGIVAAAALCILILLYAMYKYR NRDEGSYHVDESRNYISNSAQSNGAVVKEKQPSSAKSAN KNKKNKDKEYYV | 11 |
| Cyan pre-eGRASP (p30) | METDTLLLWVLLLWVPGSTGDAPVGGSKGEELFTGVVPIL VELDGDVNGHKFSVRGEGEGDATIGKLTLKFICTTGKLPV PWPTLVTTLSWGVQCFARYPDHMKRHDFFKSAMPEGYV QERTISFKDDGKYKTRAVVKFEGDTLVNRIELKGTDFKED GNILGHKLEYNFNSGNVYITADKQKNGIKANFTVRHNVED GSVQLADHYQQNTPIGDGPVLLPDNHYLSTQSVLSKDPN EKTGGSGGSGGSRAPTKPPPLPPGGGSGGGSGTEVPSS MTTESTATAMQSEMSTSIMETTTTLATSTARRGKPPTKEPI SQTTDDILVASAECPSDDEDIDPCEPSSGGLANPTRVGGR EPYPGSAEVIRESSSTTGMVVGIVAAAALCILILLYAMYKYR NRDEGSYHVDESRNYISNSAQSNGAVVKEKQPSSAKSAN KNKKNKDKEYYV | 12 |

TABLE 2-continued

| Category | Sequence | SEQ ID NO: |
|---|---|---|
| Yellow pre-eGRASP (p30) | METDTLLLWVLLLWVPGSTGDAPVGGSKGEELFTGVVPIL VELDGDVNGHKFSVRGEGEGDATIGKLTLKFICTTGKLPV PWPTLVTTLTYGVQCFARYPDHMKRHDFFKSAMPEGYV QERTISFKDDGKYKTRAVVKFEGDTLVNRIELKGTDFKED GNILGHKLEYNFNSHNVYITADKQKNGIKANFTVRHNVED GSVQLADHYQQNTPIGDGPVLLPDNHYLSYQTVLSKDPN EKTGGSGGSGGSRAPTKPPPLPPGGGSGGGSGTEVPSS MTTESTATAMQSEMSTSIMETTTTLATSTARRGKPPTKEPI SQTTDDILVASAECPSDDEDIDPCEPSSGGLANPTRVGGR EPYPGSAEVIRESSSTTGMVVGIVAAAALCILILLYAMYKYR NRDEGSYHVDESRNYISNSAQSNGAVVKEKQPSSAKSAN KNKKNKDKEYYV | 13 |
| Post-eGRASP | METDTLLLWVLLLWVPGSTGDAPVGGNDPNLFVALYDFV ASGDNTLSITKGEKLRVLGYNHNGEWCEAQTKNGQGWV PSNYITPVNSTGGGSGGGSGRDHMVLHEYVNAAGITGGG SGGGSGTLELVPHLHNLNDISQYTSTTTKVPSTDITLRPTR KNSTPVTSAFPTAKQDDPKQQPSPFSVDQRDYSTELSVTI AVGASLLFLNILAFAALYYKKDKRRHDVHRRCSPQRTTTN DLTHAPEEEIMSLQMKHTDLDHECESIHPHEVVLRTACPP DYTLAMRRSPDDIPLMTPNTITMIPNTIPGIQPLHTFNTFTG GQNNTLPHPHPHPHSHS | 14 |

1-2. Preparation of cyan pre-eGRAS

Cyan pre-eGRASP added T65S, Y66W, H148G, T205S mutations in addition to the S72A mutation of the mutant GFP (FIG. 16). FIG. 16 shows the amino acid sequence of cyan pre-eGRASP(p30), and discriminately represents (1) IgG kappa signal peptide (indicated in orange letters), (2) strands 1-10 of GFP with S72A (indicated in green letters, highlighted by cyan highlights on cyan-specific mutants T65S, Y66W, H148G, T205S), (3) p30 (indicated in red letters), (4) stalk, transmembrane, and intracellular domain of neurexin 1 b (indicated in blue letters). The p32 version is a modification of the APTKPPPLPP sequence to the p32 SPSYSPPPPP. The amino acid sequence of cyan pre-eGRASP was shown as SEQ ID NO: 12 in Table 2 (T65S, Y66W, H148G, T205S are underlined and indicated in bold).

1-3. Preparation of yellow pre-eGRASP

Yellow pre-eGRASP has a T203Y mutation in addition to S72A mutation of the mutant GFP (see FIG. 18). FIG. 18 shows the amino acid sequence of yellow pre-eGRASP (p30), and discriminately represents (1) IgG kappa signal peptide (indicated in orange letters), (2) strands 1-10 containing S72A (indicated in green letters, highlighted by yellow highlights on the yellow specific mutation T203Y), (3) p30 (indicated in red letters), (4) stalk, transmembrane and intracellular domain of neurexin 1b (indicated in blue letters). The p32 version is a modification of the sequence of APTKPPPLPP to SPSYSPPPPP. The amino acid sequence of yellow pre-eGRASP is shown as SEQ ID NO: 13 in Table 2 (T203Y is underlined and indicated in bold).

1-4. Preparation of Post-eGRASP

Post-eGRASP is composed of (1) IgG kappa signal peptide, (2) Abl SH3 peptide, (3) 11 strands of mutant GFP, and (4) stalk, transmembrane domain of neuroligin1, and an intracellular domain in which the last 4 amino acids were removed. To avoid binding of unwanted proteins and receptors, the last 4 amino acids having the PDZ domain binding site were removed. FIG. 15 shows the amino acid sequence of Post-eGRASP, and discriminately represents (1) IgG kappa signal peptide (indicated in orange letters), (2) Abl Sh3 domain (indicated in red letters), (3) strand 11 of mutant GFP (indicated in green letters), (4) stalk, transmembrane, and intracellular domain of neuroligin1 (indicated by blue letters). The amino acid sequence of Post-eGRASP was shown as SEQ ID NO: 14 in Table 2.

Example 2

Design of Fos-rtTA System

Temporally-controlled activity dependent transgene expression, which is regulated to have activity only at a specific time, utilized rtTA3G expression expressed by Fos promoter. For rapid degradation of mRNA, rtTA3G with an additional AU-rich element of fos mRNA was used. The introduced gene was expressed by the TRE3G promoter, was dependent on rtTA3G expression, and was doxycycline-dependent. FIG. 3a is a diagram showing the Fos-rtTA system designed in this example, in which yellow pre-eGRASP began to be expressed by TRE3G when injected with doxycycline. On the other hand, cyan pre-eGRASP was in a state of being always expressed. Therefore, when the memory was formed by intraperitoneally injecting doxycycline about 2 hours before the memory formation process, doxycycline spreads to a brain, thereby leading to a state that can affect the promoter. It was designed so that the process of memory formation can be visualized by observing the part in which yellow pre-eGRASP was expressed.

Example 3

Production of Adeno-Associated Virus (AAV)

AAV serotype 1/2 containing both AAV serotype 1 and 2 capsids was used. AAV1/2 was extracted from HEK293T cells transfected with genes between AAV2 ITRs, p5E18, p5E18-RXC1 and pAd-ΔF6, and the extracts were cultured in 18 ml and 8 ml of Opti-MEM (Gibco-BRL/Invitrogen, cat# 31985070), respectively, in 150 mm and 100 mm dishes.

After 4 days, the media containing AAV1/2 was centrifuged at 3000 rpm for 10 minutes. 1 ml of heparin-agarose suspension (Sigma, cat# H6508) was added to a poly-prep chromatography column (Bio-Rad Laboratories, Inc. cat# 731-1550), and then the supernatant was carefully poured.

Impurities were removed from the column with 4 ml of Buffer 4-150 (150 mM NaCl, pH4 10 mM citrate buffer) and 12 ml of Buffer 4-400 (400 mM NaCl, pH4 10 mM citrate buffer).

Virus was eluted with 4 ml of Buffer 4-1200 (1.2 M NaCl, pH4 10 mM citrate buffer). The eluted solution was changed to PBS using an Amicon Ultra-15 centrifugal filter unit (Millipore, cat# UFC910024) and concentrated. Virus concentration was determined via quantitative RT-PCR.

Example 4

Preparation of Animal Model

All experiments were performed using 8-10 week old male C57BL/6N mice purchased from Samtako Bio Korea. Mice were housed in a standard laboratory cage every 12 hours on a day/night cycle, and food and water were supplied freely. All experimental procedures and animal care were performed according to the guidelines issued by the Institutional Animal Care and Use Committee (IACUC) in Seoul National University.

The mouse was anesthetized with ketamine/xylazine, and then placed on a stereotaxic apparatus (Stoelting Co.), and the virus was injected into the desired site at a rate of 0.1 µl/min using a 33 gauge Hamilton syringe. At this time, it entered 0.05 mm deeper than the desired depth, waited for 2 minutes, and then returned to the desired location and injected. In that state, after injecting the virus and waiting for 7 minutes, the needle was slowly removed. The coordinates for each area are as follows: in FIG. 1d, the lateral entorhinal cortex (AP: −3.4/ML: −4.4/DV: −4.1), medial entorhinal cortex (AP: −4.6/ML: −3.5/DV −3.5), DG (AP: −1.75/ML: −1.5/DV: −2.2, from the skull surface); in FIG. 1e, CA3 (AP: −1.9/ML: ±2.35/DV: −2.45), CA1 (AP: −1.9/ML: −1.5/DV: −1.6); in FIGS. 2 and 3, left CA3 (AP: −1.75/ML: −2.35/DV: −2.45), CA1 (AP: −1.8/ML: +1.5/DV: −1.65, from the skull surface); in FIG. 4, double injection: AP: −1.75/ML: −2.35/DV: −2.45, AP: −2.25/ML: −2.7/DV: −2.65), right CA1 (AP: −1.8/ML: +1.5/DV: −1.65, from the skull surface).

FIG. 2a shows a schematic illustration of virus injection. In FIG. 2a, in order to express the cyan pre-eGRASP prepared in Example 1-2 and the yellow Pre-eGRASP prepared in Example 1-3 in an animal model, 0.5 ul of virus mixture (Fos-rtTA3G 1.6×10$^6$ virus genome (vg)/ul, TRE3G-Yellow 2.0×10$^8$vg/ul, CaMKIIα-iCre 4.0×10$^7$ vg/µl, EF1α-DIO-Cyan pre-eGRASP 7.5×10$^8$ vg/µl) was injected into the left CA3. Further, in order to express the Post-eGRASP prepared in Example 1-4 in an animal model, 0.5 ul of virus mixture (Fos-rtTA3G 1.6×10$^6$ vg/µl, TRE3G-myr_mScarlet-I-P2A-post-eGRASP 8.0×10$^9$ vg/µl, CaMKIIα-iCre 1.0×10$^6$ vg/µl, EF1α-DIO-myr_iRFP670-P2A-post-eGRASP 8.0×10$^8$ vg/µl) was injected into the right CA1.

In FIG. 3a, 0.5 ul of virus mixture (Fos-rtTA3G 1.6×10$^6$ vg/µl, TRE3G-Yellow pre-eGRASP 2.0×10$^8$ vg/µl, CaMKIIα-iCre 3.0×10$^7$ vg/µl, and EF1α-DIO-Cyan pre-eGRASP 7.5×10$^8$ vg/µl) was injected into the left CA3, and 0.5 ul of virus mixture (Fos-rtTA3G 1.6×10$^6$ vg/µl, TRE3G-myr_mScarlet-I-P2A-post-eGRASP 8.0×10$^9$ vg/µl, CaMKIIα-iCre 1.0×10$^6$ vg/µl, EF1α-DIO-myr_iRFP670-P2A-post-eGRASP 8.0×10$^8$ vg/µl) was injected into the right CA1.

Example 5

Generation of Contextual Fear Memory

All rats were trained 2 to 4 weeks after AAV injection. Each rat was singly housed 10 days before training (learning), and the experimenter and the anesthesia barrel were acclimated for 3 minutes each for 7 consecutive days. Training was conducted two days after the last adaptation date. On the day of training, 250 µl of 5 mg/ml doxycycline solution was injected intraperitoneally under anesthesia 2 hours before training.

Doxycycline was injected 2 hours before seizure induction or contextual fear conditioning (CFC) to successfully label activated cells during each event (FIGS. 8A to 8C and FIGS. 9A to 9D). FIGS. 8a to 8c show the results of validation experiments of the Fos-rtTA system with seizures. FIG. 8a is a schematic illustration of the injected AAV, in which the nuclear target mEmerald (mEmerald-Nuc) was regulated by the TRE3G promoter regulated by rtTA3G expressed by the Fos promoter, and the nuclear target mCherry regulated by CaMKIIα was used as an expression control. FIG. 8b is a diagram showing a timetable of actions used in the experiment, and FIG. 8c is a diagram showing that injection of Pentylenetetrazol (PTZ) induced by seizures induces a strong mEmerald-Nuc signal in DG. FIGS. 9a to 9d show the results of the verification experiment of the Fos-rtTA system using CFC. FIG. 9a shows a schematic illustration of an injected AAV. FIG. 9b is a diagram showing a timetable of actions used in the experiment. FIG. 9c shows a representative diagram. FIG. 9d is a diagram showing that CA3 induces a significant increase in mEmerald-Nuc in the contextual fear and shows a strong increase in CA1.

In FIG. 2a, the training process was performed in a square chamber with a steel grid (Med Associates Inc., St Albans, VT) for a total of 300 seconds, and an shock of 0.6 mA was applied to 208 s, 238 s, and 268 s for 2 seconds. After completion of the training, the rats were immediately transferred to their original cages. Two days after learning, the brain was extracted.

In FIG. 3a, an electric shock of 0.35 mA once and an electric shock of 0.75 mA three times were applied to 268 s, 208 s, 238 s, and 268 s, respectively, for weak and strong shocks. For the contextual exposure only, it was exposed to the same space for 300 seconds. After 2 days, the fear reaction was measured, and then the brain was extracted.

Example 6

Sample Preparation and Imaging

The extracted brain was fixed in 4% paraformaldehyde (PFA) overnight, then immersed in 30% sucrose and dehydrated for 2 days. After freezing the brain, it was sectioned to a thickness of 50 µm using a Cryostat, and mounted with VECTASHIELD® mounting medium (Vector Laboratories) or Easy-index mounting medium (Live Cell Instrument). The CA1 dendrites of the brain sections were immersed in distilled water and imaging was performed using a 63× lens of a Leica SP8 or Zeiss LSM700 confocal microscope. The second/third dendrites were imaged with Z-stack.

Example 7

Image Analysis

The Imaris (Bitplane, Zurich, Switzerland) program was used for analysis through 3D modeling. Among the dendrites expressing myr_mScarlet-I and myr_iRFP670, those capable of tracking were selected and designated as filaments. At this time, the other three channels were made invisible to eliminate the experimenter's prejudice. Further, cyan or yellow eGRASP signals were designated as cyan and yellow spheres, respectively. At this time, if the cyan and yellow signals overlap, they were considered to be yellow signals. This is because the presynaptic neurons are cells showing activity during training. Further, if there was no cyan signal or myr_mScarlet-I and myr_iRFP670 were visible at the same time, the filaments were excluded from the analysis.

Next, for eGRASP density analysis, cyan and yellow spheres were directly manually counted for each filament. The length of the dendrites was measured via Imaris FilamentTracer. The density of cyan or yellow eGRASP of each dendrite was normalized by the average of the density of cyan or yellow eGRASP of the dendrites expressed with myr_iRFP670 within one image. For structural analysis, the dendrites and eGRASP signals were labeled by the method as described above, and then only the spines with eGRASP signals were measured after 3D modeling using Imaris FilamentTracer. The 3D modeling experimenter minimized the prejudice by not knowing the color of the eGRASP signal.

Example 8

Electrophysiology

To improve the condition of adult hippocampal sections, N-methyl-D-glucamine (NMDG) solution (93 mM NMDG, 2.5 mM KCl, 1.2 mM $NaH_2PO_4$, 30 mM $NaHCO_3$, 20 mM HEPES, 25 mM Glucose, 5 mM sodium ascorbate, 2 mM Thiourea, 3 mM sodium pyruvate, 10 mM $MgSO_4$, 0.5 mM $CaCl_2$) was used for cerebral dissection and recovery. Mice were deeply anesthetized by intraperitoneal injection of a Ketamine/Xylazine mixture, and cardiac perfusion was performed with ice-cold NMDG solution. After cardiac perfusion, coronal sections (300-400 um thick) were prepared using a vibratome (VT1200S; Leica) in ice-cold NMDG solution, and recovered in an NMDG solution at 32-34° C. for 10 minutes. After recovery, the sections were transferred to modified HEPES containing normal temperature ACSF (92 mM NaCl, 2.5 mM KCl, 1.2 mM $NaH_2PO_4$, 30 mM $NaHCO_3$, 20 mM HEPES, 25 mM Glucose, 5 mM sodium ascorbate, 2 mM Thiourea, 3 mM sodium pyruvate, 2 mM $MgSO_4$, 2 mM $CaCl_2$) and recovered for at least 1 hour. After recovery, the sections were transferred to a recording room sprayed with standard ACSF (124 mM NaCl, 2.5 mM KCl, 1 mM $NaH_2PO_4$, 25 mM $NaHCO_3$, 10 mM glucose, 2 mM $CaCl_2$, and 2 mM $MgSO_4$) at RT. The recording pipettes (3-5 MΩ) were filled with the contents containing 145 mM K-gluconate, 5 mM NaCl, 10 mM HEPES, 1 mM $MgCl_2$, 0.2 mM EGTA, 2 mM MgATP, and 0.1 mM Na3GTP (280-300 mOsm, adjusted to pH 7.2 with KOH). Picrotoxin (100 uM) was added to ACSF to block GABA-R-mediated currents. Cyan light was used a 473 nm DPSS laser (Laserglow Technologies Inc.), and yellow light used a 593 nm DPSS laser (OEM Laser Systems). The intensity of light was adjusted to induce a stable synaptic response. For mEPSC experiment with $Sr^{2+}$ light, ACSF containing 4 mM $MgCl_2$ and 4 mM $SrCl_2$ was used instead of $CaCl_2$. The light was irradiated for 300 ms. In order to remove the simultaneous release factors, mEPSC events for 60-400 ms after light stimulation were analyzed with the MiniAnalysis program (Synaptosoft).

In the pairing (pair)-LTP experiment, EPSCs were evoked at 0.05 Hz, and three consecutive EPSCs were averaged and presented for a normalized baseline. To induce pairing-LTP, four short high-frequency *tetani* (50 pulses of 20 Hz each at 4 second intervals) and long depolarization (0 mV, 3 min) were paired and performed after long depolarization. Hippocampal neurons were fixed at voltage at −70 mV using Axopatch 200B (Molecular Devices). Only cells with less than 20% change in access resistance were used for analysis. Expression of mEmerald-nuc was confirmed by a cooled CCD camera (PROGRES MF COOL®; Jenoptik) and a fluorescence microscope (BX51W1; Olympus).

Example 9

Statistical Analysis

The data was analyzed via the Prism program. After Mann Whitney two-tailed test and one-way ANOVA, Tukey's multiple comparison test was used to determine the statistical significance.

Experimental Example 1

Synaptic Labeling Derived from Engram Cells of Specific Events

To apply Dual-eGRASP on synaptic connections between engram cells derived from two different regions, the present inventors utilized a Fos promoter-driven reverse tetracycline-controlled transactivator (rtTA) delivered by adeno-associated virus (AAV) to express specific genes of interest in engram cells at a specific time point. Doxycycline injection 2 hours before seizure induction or contextual fear conditioning (CFC) successfully labeled the cells activated during these events (FIGS. 8 and 9). Using this Fos-rtTA system, the inventors expressed post-eGRASP together with membrane-targeted mScarlet-I unilaterally in CA1 engram cells, and expressed yellow pre-eGRASP in the contralateral CA3 engram cells to avoid possible co-expression of pre-eGRASP and post-eGRASP. This system labeled CA3 engram to CA1 engram (E-E) synapses with yellow eGRASP signals on red fluorescently labeled dendrites.

To compare these synapses with other synapses [non-engram to engram (N-E), engram to non-engram (E-N), and non-engram to non-engram (N-N) synapses], the inventors expressed post-eGRASP together with membrane-targeted iRFP670 in a neuronal population from the ipsilateral CA1, while expressing cyan pre-eGRASP in a random neuronal population from the contralateral CA3. Strong expression was achieved in the random neuronal population using a high titer of double-floxed inverted open reading frame (DIO) AAV with a lower titer of Cre recombinase expressing AAV (FIG. 2a).

It was confirmed that yellow pre-eGRASP expression is doxycycline dependent, demonstrating that the system designed in the example of the present disclosure can label synapses originating from engram cells of a specific event (FIGS. 10a and 10b). It shows a representative diagram of the expression of cyan and yellow eGRASP, when doxycycline was not injected (FIG. 10a), and when doxycycline was injected (FIG. 10b). The inventors successfully distinguished four types of synapses in the same brain slice after contextual fear conditioning experiment. Based on the percentage of overlapping fluorescence, CA3 cells expressing cyan pre-eGRASP, yellow pre-eGRASP, CA1 cells expressing iRFP and mScarlet-I were estimated to be 78.38%, 40.25%, 11.61%, and 20.93%, respectively (FIG. 11). Cyan and yellow puncta on near-infrared (iRFP670) dendrites indicated N-N and E-N synapses, respectively, while cyan and yellow puncta on red (mScarlet-I) dendrites indicated N-E and E-E synapses, respectively (FIGS. 2b and 2c). Puncta expressing both cyan and yellow fluorescence was considered as synapses originating from engram cells. This is because these synapses originate from CA3 cells expressing both cyan pre-eGRASP (randomly selected population) and yellow pre-eGRASP (engram cells).

No significant differences were found between the density of N-N and N-E synapses (FIG. 2d, FIGS. 12, a and c); however, the density of E-E synapses was significantly higher than E-N synapses (FIG. 2d, FIGS. 12b and 12d). This difference indicates that presynaptic terminals from CA3 engram cells predominantly synapsed on CA1 engram cells rather than CA1 non-engram cells.

The size of spines was also examined in each synapse population. N-N and E-N did not show any significant differences, whereas E-E spine head diameter and spine volume were significantly greater than N-E synaptic spines (FIG. 2e). These results indicate that the spines of CA1 cells receiving connections from CA3 engram cells were selectively potentiated.

Experimental Example 2

Establishment of Dual-eGRASP System

In order to compare one post-synaptic neuron with two other pre-synaptic populations, the present inventors have complemented green fluorescent protein reconstitution across synaptic partners (GRASP). GRASP used complementary mutation GFP fragments, which were expressed in the pre- and post-synaptic membranes, respectively, and bound to the synaptic cleft to form complete GFP.

The GFP signal indicates a synapse formed between neurons expressing the pre-synaptic portion and neurons expressing the post-synaptic portion. The present inventors developed an improved GRASP technique (eGRASP) with increased GRASP signal strength by introducing a weakly interacting domain that facilitates GFP reconstitution and a single mutation commonly found on most improved mutant GFP (see FIG. 5). Furthermore, eGRASP was developed by reconstituting a cyan or yellow fluorescent protein (FIGS. 1a and 1 b, FIG. 6). Color determining domains were placed in pre-synaptic neurons (blue/yellow pre-eGRASP) and common domains were placed in post-synaptic neurons (post-eGRASP), thus enabling visualization of the two synapse populations derived from two different synaptic neurons toward one post-synapse neuron. The present inventors named the technique as dual-eGRASP (FIG. 1a).

Experimental Example 3

Application of Dual-eGRASP System

In order to confirm whether the dual-eGRASP system established in Experimental Example 2 is actually applicable, the dual-eGRASP system was applied to human kidney cells, nerve cells, and the like.

3-1: Application of Dual-eGRASP System in HEK293T Cells

FIG. 1c shows three populations of HEK293T cells separately transduced using nucleofection. One population expressed cyan pre-eGRASP and mCherry, another population expresses yellow pre-eGRASP and mCherry, and the third population expresses post-eGRASP and iRFP670. According to FIG. 1c, it could be confirmed that when the dual-eGRASP pre constructs (cyan, yellow) and post constructs were separately expressed in HEK293T cells, and then mixed together and contacted, eGRASP signal was generated. In addition, it was found that the two colors represent the contact connections of HEK293T cells expressing a common domain and cells expressing any one of the color-determining domain.

3-2: Application of Dual-eGRASP System in Neurons

FIG. 1d is a diagram showing an application example of dual-eGRASP in neurons. Pre cyan GRASP was expressed in the lateral entorhinal cortex (LEC), pre yellow GRASP was expressed in the medial entorhinal cortex (MEC), and the post eGRASP construct was expressed in the dental gyrus (DG). FIG. 1d shows that cyan pre-eGRASP and yellow pre-eGRASP were expressed in the LEC and MEC, respectively. Post-eGRASP was expressed together with myristoylated TagRFP-T (myr_agRFP-T) in the DG.

As a result, it was confirmed that the dual-eGRASP system was successfully applied to synapses on dental gyrus (DG) granule cells originating from either the lateral entorhinal cortex (LEC) or the medial entorhinal cortex (MEC) that projected to the outer or inner molecular layers of the dental gyrus (DG) (FIG. 1d). Therefore, the utility of dual-eGRASP technique capable of confirming projections from different brain regions was confirmed.

In the case of FIG. 1e, cyan pre GRASP was expressed in the right CA3 and yellow pre GRASP was expressed in the left CA3, so that connections from both CA3s was confirmed in CA1 expressing post GRASP. In FIG. 1e, cyan pre-eGRASP and yellow pre-eGRASP were expressed in the right CA3 and left CA3, respectively. Post-eGRASP was expressed together with myrTagRFP-T in CA1. Therefore, it was possible to separately label intermixed synapses that did not show a unique spatial distribution on CA1 pyramidal neurons that originate from either the contralateral CA3 or ipsilateral CA3 (FIG. 1e).

3-3: Dual-eGRASP system does not affect the electrophysiology of cells

FIGS. 7a to 7c are views confirming that the expression of the dual-eGRASP components does not affect basic synaptic transmission, and FIG. 7a shows the tracking results from representative miniature EPSC (mEPSC) recordings. FIGS. 7b and 7c show the amplitude and frequency of mEPSCs of CA1 pyramidal neurons in fragments expressing eGRASP components in the CA3 and CA1 as indicated, respectively.

As a result, even if the dual-eGRASP system according to an embodiment of the present disclosure is introduced into a cell or an animal, it could label the desired without affecting existing electrophysiological characteristics of the cell or animal. Specifically, even when the eGRASP system was applied, the eGRASP system did not enhance synaptic transmission between neurons expressing pre-eGRASP and post-eGRASP, which indicates that the dual-eGRASP system according to an embodiment of the present disclosure does not affect the existing electrophysiological characteristics.

Experimental Example 4

Investigating Correlation Between Memory Strength and Connectivity of Engram Cells Next, the present inventors hypothesized that even if the number of engram cells remains constant at various memory intensities, the connectivity between the engram cells before and after may encode the memory strength. The combination AAV and injection position as shown in FIG. 2 was made to be the same and it was observed whether the memory strength was proportional to the connectivity between engram cells (FIG. 3a).

Specifically, mice were divided into three groups in order to induce memories of different intensity. One group exposed only to the context of on the foot part of the mouse without electric shock, while the other group of mice were exposed to electric shocks, either weak (0.35 mA, 1 shock) or strong (0.75 mA, 3 shocks), to the foot parts to generate contextual fear memories (FIG. 3b).

As a result, increasing the intensity of the electric shock during memory generation showed a higher fear response level (freezing) (FIG. 3c). On the other hand, when quantifying the number of CA3 and CA1 engram cells, no significant differences between the three groups were found (FIG. 13).

There was no significant difference in the density between N-N and N-E synapses in all groups. However, the E-E synaptic density significantly increased in the strong-shocked group compared to the non-shocked or low-shocked group (FIGS. 3d and 3e). In addition, the spine size showed a correlation between memory strength and volume. N-N and E-N did not show any significant changes in all groups, whereas the E-E spine head diameter and spine volume were significantly greater in the group receiving a stronger impact than in the other groups (FIGS. 3f and FIG. 14).

Experimental Example 5

Investigation of Synaptic Strength

Next, the present inventors observed increased structural connectivity between CA3 and CA1 memory cells after memory formation, and therefore, investigated synaptic strength of these synapses. Two different inputs from CA3 neurons were selectively stimulated using two opsins, Chronos and ChrimsonR, that can be independently activated using blue and yellow wavelength lasers, respectively. First, Chronos was expressed in CA3 excitatory neurons under the calcium/calmodulin-dependent protein kinase type II alpha (CaMKIIα) promoter, while ChrimsonR was expressed in CA3 engram neurons using Fos-rtTA (FIG. 4a). CA1 engram neurons were labeled with nucleustargeted mEmerald (mEmerald-Nuc) using FosrTA, and then whole-cell recordings were performed from either CA1 engram or non-engram neurons. The following four combinations of synaptic responses in a single hippocampal slice after contextual fear conditioning: total excitatory to non-engram (T-N), total excitatory to engram (T-E), engram to non-engram (E-N), and engram to engram (E-E) were investigated (FIG. 4b).

First, presynaptic transmission was investigated using paired-pulse ratios (PPR) (FIGS. 4c and 4d). PPR from CA3 engram inputs were significantly decreased at 25-, 50-, and 75-ms interstimulus intervals, which confirmed increased release probability from CA3 engram inputs to CA1. Such decrease was most prominent in E-E synaptic responses (FIG. 4e). Postsynaptic α-amino-3-hydroxy-5-methyl-4-isoxazolepropionic acid (AMPA) receptor levels in individual synapses were measured from the four combinations of synaptic responses by replacing $Ca^{2+}$ with $Sr^{2+}$ in the external recording solution.

$Sr^{2+}$ desynchronized evoked release and induced prolonged asynchronous release, which enabled measurement of quantal synaptic response (FIG. 4f). The amplitude of evokedminiature excitatory post-synaptic currents (mEPSCs) 60 to 400 ms after light stimulation was measured. Synapses from CA1 engram cells exhibited significantly increased levels of postsynaptic AMPA receptors compared with CA1 non-engram cell levels (FIG. 4G). These results indicate that the synapses of CA1 engram cells were potentiated after memory formation but not the synapses of CA1 non-engram cells. Alterations in both presynaptic release probability and post-synaptic potentiation play an important role in long-term potentiation (LTP). To measure the existence of LTP during memory formation, the extent of LTP occlusion was examined by inducing pairing LTP separately in the four synaptic types (FIG. 4H). After 5 min of baseline recording, pairing LTP stimuli was delivered. Robustly potentiated T-N synaptic responses was observed (~150%). T-E and E-N synaptic responses were potentiated to a lower extent than T-N synaptic responses (-120%), but these differences were not significant. Interestingly, it was found that pairing LTP in E-E synaptic responses was completely blocked and potentiation was significantly lower than T-N synaptic responses (FIG. 4i).

Our finding that synaptic populations that fired together during memory formation showed the strongest connections demonstrates that classical Hebbian plasticity indeed occurs during the learning and memory process at CA3 to CA1 synapses. The present inventors propose the hypothesis that cells with higher connectivity are allocated together into a memory circuit, in contrast to enhanced connectivity after learning. However, the allocated cell number remains constant regardless of the memory strength, whereas the connectivity is significantly enhanced with a stronger memory. This finding indicates a significant contribution of post-learning enhancement over the predetermined connectivity. The relationship between memory strength and synaptic connectivity suggests that these specific connections between engram cells across two directly connected brain regions form the synaptic substrate for memory.

The invention claimed is:

1. A method of confirming intercellular contact, comprising the steps of:
introducing a first labeling material and a second labeling material into a first cell and a second cell, respectively, wherein the first labeling material and the second labeling material are bound to each other to generate a signal; and
detecting the signal,
wherein the first labeling material is at least two types of labeling materials that are different from each other, and the two or more first labeling materials generate mutually different fluorescent signals, and
wherein the second labeling material is at least two types of labeling materials, each of which binds to the corresponding at least two types of the first labeling materials,
wherein the first labeling material is at least one selected from the group consisting of:
a polypeptide of SEQ ID NO: 11, a gene encoding the polypeptide of SEQ ID NO: 11, or a vector including a gene encoding the polypeptide of SEQ ID NO: 11;
a polypeptide of SEQ ID NO: 12, a gene encoding the polypeptide of SEQ ID NO: 12, or a vector including a gene encoding the polypeptide of SEQ ID NO: 12; and
a polypeptide of SEQ ID NO: 13, a gene encoding the polypeptide of SEQ ID NO: 13, or a vector including a gene encoding the polypeptide of SEQ ID NO: 13,
wherein the second labeling material is at least one selected from the group consisting of: a polypeptide of SEQ ID NO: 14, a gene encoding the polypeptide of SEQ ID NO: 14, or a vector including a gene encoding the polypeptide of SEQ ID NO: 14.

2. The method of claim 1, further comprising a step of determining that the first cell and the second cell are in contact with each other when the signal is detected, after the step of detecting the signal.

3. The method of claim 1, wherein the first labeling material comprises a part of a fluorescent protein, a gene encoding a part of the fluorescent protein, or a vector including a gene encoding a part of the fluorescent protein, the second labeling material comprises the remaining part of the fluorescent protein, a gene encoding the remaining part of the fluorescent protein, or a vector including a gene encoding the remaining part of the fluorescent protein.

4. The method of claim 1, wherein the genes encoding each of at least two different first labeling materials are introduced into the first cell, and at least one or more of the genes introduced into the first cell is operably linked to an activity-dependent promoter.

5. The method of claim 1, wherein the second labeling material is expressed at two or more gene regions in the second cell, the second labeling material is expressed together with a fluorescent protein that is mutually distinguishable, and at least one of the second labeling material is expressed by a gene which is operably linked to an activity-dependent promoter.

6. The method of claim 4, wherein the activity-dependent promoter is at least one selected from the group consisting of fos promoter, Arc promoter, and immediate early gene promoter.

7. The method of claim 5, wherein the activity-dependent promoter is at least one selected from the group consisting of fos promoter, Arc promoter, and immediate early gene promoter.

8. The method of claim 1, wherein the intercellular contact is that the first cell and the second cell are positioned with a distance of 40 nm or less.

9. The method of claim 1, wherein the cell is at least one selected from the group consisting of: neurons, astrocyte, microglia, oligodendrocytes, immune cells, T cells, and B cells.

* * * * *

SEQUENCE LISTING

<160> NUMBER OF SEQ ID NOS: 14

<210> SEQ ID NO 1
<211> LENGTH: 24
<212> TYPE: PRT
<213> ORGANISM: Artificial Sequence
<220> FEATURE:
<223> OTHER INFORMATION: (synthetic) IgG kappa signal peptide

<400> SEQUENCE: 1

Met Glu Thr Asp Thr Leu Leu Leu Trp Val Leu Leu Leu Trp Val Pro
1               5                   10                  15

Gly Ser Thr Gly Asp Ala Pro Val
            20

<210> SEQ ID NO 2
<211> LENGTH: 213
<212> TYPE: PRT
<213> ORGANISM: Artificial Sequence
<220> FEATURE:
<223> OTHER INFORMATION: (synthetic) pre-eGRASP strand 1-10 with S72A
      mutation

<400> SEQUENCE: 2

Ser Lys Gly Glu Glu Leu Phe Thr Gly Val Val Pro Ile Leu Val Glu
1               5                   10                  15

Leu Asp Gly Asp Val Asn Gly His Lys Phe Ser Val Arg Gly Glu Gly
            20                  25                  30

Glu Gly Asp Ala Thr Ile Gly Lys Leu Thr Leu Lys Phe Ile Cys Thr
        35                  40                  45

Thr Gly Lys Leu Pro Val Pro Trp Pro Thr Leu Val Thr Thr Leu Thr
50                  55                  60

Tyr Gly Val Gln Cys Phe Ala Arg Tyr Pro Asp His Met Lys Arg His
65                  70                  75                  80

Asp Phe Phe Lys Ser Ala Met Pro Glu Gly Tyr Val Gln Glu Arg Thr
                85                  90                  95

Ile Ser Phe Lys Asp Asp Gly Lys Tyr Lys Thr Arg Ala Val Val Lys
            100                 105                 110

Phe Glu Gly Asp Thr Leu Val Asn Arg Ile Glu Leu Lys Gly Thr Asp
        115                 120                 125

Phe Lys Glu Asp Gly Asn Ile Leu Gly His Lys Leu Glu Tyr Asn Phe
130                 135                 140

Asn Ser His Asn Val Tyr Ile Thr Ala Asp Lys Gln Lys Asn Gly Ile
145                 150                 155                 160

Lys Ala Asn Phe Thr Val Arg His Asn Val Glu Asp Gly Ser Val Gln
                165                 170                 175

Leu Ala Asp His Tyr Gln Gln Asn Thr Pro Ile Gly Asp Gly Pro Val
            180                 185                 190

Leu Leu Pro Asp Asn His Tyr Leu Ser Thr Gln Thr Val Leu Ser Lys
        195                 200                 205

Asp Pro Asn Glu Lys
    210

<210> SEQ ID NO 3
<211> LENGTH: 213
<212> TYPE: PRT
<213> ORGANISM: Artificial Sequence
<220> FEATURE:
<223> OTHER INFORMATION: (synthetic) Cyan pre-eGRASP strand 1-10

<400> SEQUENCE: 3

Ser Lys Gly Glu Glu Leu Phe Thr Gly Val Val Pro Ile Leu Val Glu
1               5                   10                  15

Leu Asp Gly Asp Val Asn Gly His Lys Phe Ser Val Arg Gly Glu Gly
            20                  25                  30

Glu Gly Asp Ala Thr Ile Gly Lys Leu Thr Leu Lys Phe Ile Cys Thr
        35                  40                  45

Thr Gly Lys Leu Pro Val Pro Trp Pro Thr Leu Val Thr Thr Leu Ser
50                  55                  60

```
Trp Gly Val Gln Cys Phe Ala Arg Tyr Pro Asp His Met Lys Arg His
 65                  70                  75                  80

Asp Phe Phe Lys Ser Ala Met Pro Glu Gly Tyr Val Gln Glu Arg Thr
                 85                  90                  95

Ile Ser Phe Lys Asp Asp Gly Lys Tyr Lys Thr Arg Ala Val Val Lys
            100                 105                 110

Phe Glu Gly Asp Thr Leu Val Asn Arg Ile Glu Leu Lys Gly Thr Asp
        115                 120                 125

Phe Lys Glu Asp Gly Asn Ile Leu Gly His Lys Leu Glu Tyr Asn Phe
    130                 135                 140

Asn Ser Gly Asn Val Tyr Ile Thr Ala Asp Lys Gln Lys Asn Gly Ile
145                 150                 155                 160

Lys Ala Asn Phe Thr Val Arg His Asn Val Glu Asp Gly Ser Val Gln
                165                 170                 175

Leu Ala Asp His Tyr Gln Gln Asn Thr Pro Ile Gly Asp Gly Pro Val
            180                 185                 190

Leu Leu Pro Asp Asn His Tyr Leu Ser Thr Gln Ser Val Leu Ser Lys
        195                 200                 205

Asp Pro Asn Glu Lys
    210

<210> SEQ ID NO 4
<211> LENGTH: 213
<212> TYPE: PRT
<213> ORGANISM: Artificial Sequence
<220> FEATURE:
<223> OTHER INFORMATION: (synthetic) Yellow pre-eGRASP strand 1-10

<400> SEQUENCE: 4

Ser Lys Gly Glu Glu Leu Phe Thr Gly Val Val Pro Ile Leu Val Glu
 1               5                  10                  15

Leu Asp Gly Asp Val Asn Gly His Lys Phe Ser Val Arg Gly Glu Gly
                20                  25                  30

Glu Gly Asp Ala Thr Ile Gly Lys Leu Thr Leu Lys Phe Ile Cys Thr
            35                  40                  45

Thr Gly Lys Leu Pro Val Pro Trp Pro Thr Leu Val Thr Thr Leu Thr
 50                  55                  60

Tyr Gly Val Gln Cys Phe Ala Arg Tyr Pro Asp His Met Lys Arg His
 65                  70                  75                  80

Asp Phe Phe Lys Ser Ala Met Pro Glu Gly Tyr Val Gln Glu Arg Thr
                 85                  90                  95

Ile Ser Phe Lys Asp Asp Gly Lys Tyr Lys Thr Arg Ala Val Val Lys
            100                 105                 110

Phe Glu Gly Asp Thr Leu Val Asn Arg Ile Glu Leu Lys Gly Thr Asp
        115                 120                 125

Phe Lys Glu Asp Gly Asn Ile Leu Gly His Lys Leu Glu Tyr Asn Phe
    130                 135                 140

Asn Ser His Asn Val Tyr Ile Thr Ala Asp Lys Gln Lys Asn Gly Ile
145                 150                 155                 160

Lys Ala Asn Phe Thr Val Arg His Asn Val Glu Asp Gly Ser Val Gln
                165                 170                 175

Leu Ala Asp His Tyr Gln Gln Asn Thr Pro Ile Gly Asp Gly Pro Val
            180                 185                 190

Leu Leu Pro Asp Asn His Tyr Leu Ser Tyr Gln Thr Val Leu Ser Lys
        195                 200                 205
```

Asp Pro Asn Glu Lys
    210

<210> SEQ ID NO 5
<211> LENGTH: 16
<212> TYPE: PRT
<213> ORGANISM: Artificial Sequence
<220> FEATURE:
<223> OTHER INFORMATION: (synthetic) Post-eGRASP strand 11

<400> SEQUENCE: 5

Arg Asp His Met Val Leu His Glu Tyr Val Asn Ala Ala Gly Ile Thr
1               5                   10                  15

<210> SEQ ID NO 6
<211> LENGTH: 10
<212> TYPE: PRT
<213> ORGANISM: Artificial Sequence
<220> FEATURE:
<223> OTHER INFORMATION: (synthetic) p30

<400> SEQUENCE: 6

Ala Pro Thr Lys Pro Pro Pro Leu Pro Pro
1               5                   10

<210> SEQ ID NO 7
<211> LENGTH: 10
<212> TYPE: PRT
<213> ORGANISM: Artificial Sequence
<220> FEATURE:
<223> OTHER INFORMATION: (synthetic) p32

<400> SEQUENCE: 7

Ser Pro Ser Tyr Ser Pro Pro Pro Pro Pro
1               5                   10

<210> SEQ ID NO 8
<211> LENGTH: 61
<212> TYPE: PRT
<213> ORGANISM: Artificial Sequence
<220> FEATURE:
<223> OTHER INFORMATION: (synthetic) Abl Sh3 domain

<400> SEQUENCE: 8

Asn Asp Pro Asn Leu Phe Val Ala Leu Tyr Asp Phe Val Ala Ser Gly
1               5                   10                  15

Asp Asn Thr Leu Ser Ile Thr Lys Gly Glu Lys Leu Arg Val Leu Gly
                20                  25                  30

Tyr Asn His Asn Gly Glu Trp Cys Glu Ala Gln Thr Lys Asn Gly Gln
            35                  40                  45

Gly Trp Val Pro Ser Asn Tyr Ile Thr Pro Val Asn Ser
        50                  55                  60

<210> SEQ ID NO 9
<211> LENGTH: 179
<212> TYPE: PRT
<213> ORGANISM: Artificial Sequence
<220> FEATURE:
<223> OTHER INFORMATION: (synthetic) neurexin 1b

<400> SEQUENCE: 9

Glu Val Pro Ser Ser Met Thr Thr Glu Ser Thr Ala Thr Ala Met Gln
1               5                   10                  15

Ser Glu Met Ser Thr Ser Ile Met Glu Thr Thr Thr Thr Leu Ala Thr
                20                  25                  30

```
Ser Thr Ala Arg Arg Gly Lys Pro Pro Thr Lys Glu Pro Ile Ser Gln
            35                  40                  45

Thr Thr Asp Asp Ile Leu Val Ala Ser Ala Glu Cys Pro Ser Asp Asp
    50                  55                  60

Glu Asp Ile Asp Pro Cys Glu Pro Ser Ser Gly Gly Leu Ala Asn Pro
65                  70                  75                  80

Thr Arg Val Gly Gly Arg Glu Pro Tyr Pro Gly Ser Ala Glu Val Ile
                85                  90                  95

Arg Glu Ser Ser Ser Thr Thr Gly Met Val Val Gly Ile Val Ala Ala
                100                 105                 110

Ala Ala Leu Cys Ile Leu Ile Leu Leu Tyr Ala Met Tyr Lys Tyr Arg
            115                 120                 125

Asn Arg Asp Glu Gly Ser Tyr His Val Asp Glu Ser Arg Asn Tyr Ile
            130                 135                 140

Ser Asn Ser Ala Gln Ser Asn Gly Ala Val Val Lys Glu Lys Gln Pro
145                 150                 155                 160

Ser Ser Ala Lys Ser Ala Asn Lys Asn Lys Lys Asn Lys Asp Lys Glu
                165                 170                 175

Tyr Tyr Val

<210> SEQ ID NO 10
<211> LENGTH: 213
<212> TYPE: PRT
<213> ORGANISM: Artificial Sequence
<220> FEATURE:
<223> OTHER INFORMATION: (synthetic) neuroligin1

<400> SEQUENCE: 10

Leu Glu Leu Val Pro His Leu His Asn Leu Asn Asp Ile Ser Gln Tyr
1               5                   10                  15

Thr Ser Thr Thr Thr Lys Val Pro Ser Thr Asp Ile Thr Leu Arg Pro
                20                  25                  30

Thr Arg Lys Asn Ser Thr Pro Val Thr Ser Ala Phe Pro Thr Ala Lys
            35                  40                  45

Gln Asp Asp Pro Lys Gln Gln Pro Ser Pro Phe Ser Val Asp Gln Arg
    50                  55                  60

Asp Tyr Ser Thr Glu Leu Ser Val Thr Ile Ala Val Gly Ala Ser Leu
65                  70                  75                  80

Leu Phe Leu Asn Ile Leu Ala Phe Ala Ala Leu Tyr Tyr Lys Lys Asp
                85                  90                  95

Lys Arg Arg His Asp Val His Arg Arg Cys Ser Pro Gln Arg Thr Thr
                100                 105                 110

Thr Asn Asp Leu Thr His Ala Pro Glu Glu Glu Ile Met Ser Leu Gln
            115                 120                 125

Met Lys His Thr Asp Leu Asp His Glu Cys Glu Ser Ile His Pro His
            130                 135                 140

Glu Val Val Leu Arg Thr Ala Cys Pro Pro Asp Tyr Thr Leu Ala Met
145                 150                 155                 160

Arg Arg Ser Pro Asp Asp Ile Pro Leu Met Thr Pro Asn Thr Ile Thr
                165                 170                 175

Met Ile Pro Asn Thr Ile Pro Gly Ile Gln Pro Leu His Thr Phe Asn
            180                 185                 190

Thr Phe Thr Gly Gly Gln Asn Asn Thr Leu Pro His Pro His Pro His
            195                 200                 205
```

Pro His Ser His Ser
    210

<210> SEQ ID NO 11
<211> LENGTH: 449
<212> TYPE: PRT
<213> ORGANISM: Artificial Sequence
<220> FEATURE:
<223> OTHER INFORMATION: (synthetic) Pre-eGRASP (p30)

<400> SEQUENCE: 11

Met Glu Thr Asp Thr Leu Leu Leu Trp Val Leu Leu Trp Val Pro
1               5                   10                  15

Gly Ser Thr Gly Asp Ala Pro Val Gly Gly Ser Lys Gly Glu Leu
                20                  25                  30

Phe Thr Gly Val Val Pro Ile Leu Val Glu Leu Asp Gly Asp Val Asn
                35                  40                  45

Gly His Lys Phe Ser Val Arg Gly Glu Gly Glu Gly Asp Ala Thr Ile
    50                      55                  60

Gly Lys Leu Thr Leu Lys Phe Ile Cys Thr Thr Gly Lys Leu Pro Val
65                  70                  75                  80

Pro Trp Pro Thr Leu Val Thr Thr Leu Thr Tyr Gly Val Gln Cys Phe
                85                  90                  95

Ala Arg Tyr Pro Asp His Met Lys Arg His Asp Phe Phe Lys Ser Ala
                100                 105                 110

Met Pro Glu Gly Tyr Val Gln Glu Arg Thr Ile Ser Phe Lys Asp Asp
                115                 120                 125

Gly Lys Tyr Lys Thr Arg Ala Val Val Lys Phe Glu Gly Asp Thr Leu
    130                 135                 140

Val Asn Arg Ile Glu Leu Lys Gly Thr Asp Phe Lys Glu Asp Gly Asn
145                 150                 155                 160

Ile Leu Gly His Lys Leu Glu Tyr Asn Phe Asn Ser His Asn Val Tyr
                165                 170                 175

Ile Thr Ala Asp Lys Gln Lys Asn Gly Ile Lys Ala Asn Phe Thr Val
                180                 185                 190

Arg His Asn Val Glu Asp Gly Ser Val Gln Leu Ala Asp His Tyr Gln
    195                 200                 205

Gln Asn Thr Pro Ile Gly Asp Gly Pro Val Leu Leu Pro Asp Asn His
    210                 215                 220

Tyr Leu Ser Thr Gln Thr Val Leu Ser Lys Asp Pro Asn Glu Lys Thr
225                 230                 235                 240

Gly Gly Ser Gly Gly Ser Gly Gly Ser Arg Ala Pro Thr Lys Pro Pro
                245                 250                 255

Pro Leu Pro Pro Gly Gly Gly Ser Gly Gly Ser Gly Thr Glu Val
                260                 265                 270

Pro Ser Ser Met Thr Thr Glu Ser Thr Ala Thr Ala Met Gln Ser Glu
                275                 280                 285

Met Ser Thr Ser Ile Met Glu Thr Thr Thr Leu Ala Thr Ser Thr
    290                 295                 300

Ala Arg Arg Gly Lys Pro Pro Thr Lys Glu Pro Ile Ser Gln Thr Thr
305                 310                 315                 320

Asp Asp Ile Leu Val Ala Ser Ala Glu Cys Pro Ser Asp Asp Glu Asp
                325                 330                 335

Ile Asp Pro Cys Glu Pro Ser Ser Gly Gly Leu Ala Asn Pro Thr Arg
                340                 345                 350

Val Gly Gly Arg Glu Pro Tyr Pro Gly Ser Ala Glu Val Ile Arg Glu
            355                 360                 365

Ser Ser Ser Thr Thr Gly Met Val Val Gly Ile Val Ala Ala Ala
370                 375                 380

Leu Cys Ile Leu Ile Leu Leu Tyr Ala Met Tyr Lys Tyr Arg Asn Arg
385                 390                 395                 400

Asp Glu Gly Ser Tyr His Val Asp Glu Ser Arg Asn Tyr Ile Ser Asn
                405                 410                 415

Ser Ala Gln Ser Asn Gly Ala Val Val Lys Glu Lys Gln Pro Ser Ser
            420                 425                 430

Ala Lys Ser Ala Asn Lys Asn Lys Asn Lys Asp Lys Glu Tyr Tyr
        435                 440                 445

Val

<210> SEQ ID NO 12
<211> LENGTH: 449
<212> TYPE: PRT
<213> ORGANISM: Artificial Sequence
<220> FEATURE:
<223> OTHER INFORMATION: (synthetic) Cyan pre-eGRASP (p30)

<400> SEQUENCE: 12

Met Glu Thr Asp Thr Leu Leu Leu Trp Val Leu Leu Leu Trp Val Pro
1               5                   10                  15

Gly Ser Thr Gly Asp Ala Pro Val Gly Ser Lys Gly Glu Glu Leu
            20                  25                  30

Phe Thr Gly Val Val Pro Ile Leu Val Glu Leu Asp Gly Asp Val Asn
        35                  40                  45

Gly His Lys Phe Ser Val Arg Gly Glu Gly Glu Gly Asp Ala Thr Ile
    50                  55                  60

Gly Lys Leu Thr Leu Lys Phe Ile Cys Thr Thr Gly Lys Leu Pro Val
65                  70                  75                  80

Pro Trp Pro Thr Leu Val Thr Thr Leu Ser Trp Gly Val Gln Cys Phe
                85                  90                  95

Ala Arg Tyr Pro Asp His Met Lys Arg His Asp Phe Phe Lys Ser Ala
            100                 105                 110

Met Pro Glu Gly Tyr Val Gln Glu Arg Thr Ile Ser Phe Lys Asp Asp
        115                 120                 125

Gly Lys Tyr Lys Thr Arg Ala Val Val Lys Phe Glu Gly Asp Thr Leu
    130                 135                 140

Val Asn Arg Ile Glu Leu Lys Gly Thr Asp Phe Lys Glu Asp Gly Asn
145                 150                 155                 160

Ile Leu Gly His Lys Leu Glu Tyr Asn Phe Asn Ser Gly Asn Val Tyr
                165                 170                 175

Ile Thr Ala Asp Lys Gln Lys Asn Gly Ile Lys Ala Asn Phe Thr Val
            180                 185                 190

Arg His Asn Val Glu Asp Gly Ser Val Gln Leu Ala Asp His Tyr Gln
        195                 200                 205

Gln Asn Thr Pro Ile Gly Asp Gly Pro Val Leu Leu Pro Asp Asn His
    210                 215                 220

Tyr Leu Ser Thr Gln Ser Val Leu Ser Lys Asp Pro Asn Glu Lys Thr
225                 230                 235                 240

Gly Gly Ser Gly Gly Ser Gly Gly Ser Arg Ala Pro Thr Lys Pro Pro
                245                 250                 255

Pro Leu Pro Pro Gly Gly Gly Ser Gly Gly Gly Ser Gly Thr Glu Val

```
                    260                 265                 270
Pro Ser Ser Met Thr Glu Ser Thr Ala Thr Ala Met Gln Ser Glu
                275                 280                 285
Met Ser Thr Ser Ile Met Glu Thr Thr Thr Leu Ala Thr Ser Thr
                290                 295                 300
Ala Arg Arg Gly Lys Pro Thr Lys Glu Pro Ile Ser Gln Thr Thr
305                 310                 315                 320
Asp Asp Ile Leu Val Ala Ser Ala Glu Cys Pro Ser Asp Glu Asp
                325                 330                 335
Ile Asp Pro Cys Glu Pro Ser Ser Gly Gly Leu Ala Asn Pro Thr Arg
                340                 345                 350
Val Gly Gly Arg Glu Pro Tyr Pro Gly Ser Ala Glu Val Ile Arg Glu
                355                 360                 365
Ser Ser Ser Thr Thr Gly Met Val Val Gly Ile Val Ala Ala Ala
                370                 375                 380
Leu Cys Ile Leu Ile Leu Leu Tyr Ala Met Tyr Lys Tyr Arg Asn Arg
385                 390                 395                 400
Asp Glu Gly Ser Tyr His Val Asp Glu Ser Arg Asn Tyr Ile Ser Asn
                405                 410                 415
Ser Ala Gln Ser Asn Gly Ala Val Val Lys Glu Lys Gln Pro Ser Ser
                420                 425                 430
Ala Lys Ser Ala Asn Lys Asn Lys Asn Lys Asp Lys Glu Tyr Tyr
                435                 440                 445
Val

<210> SEQ ID NO 13
<211> LENGTH: 449
<212> TYPE: PRT
<213> ORGANISM: Artificial Sequence
<220> FEATURE:
<223> OTHER INFORMATION: (synthetic) Yellow pre-eGRASP (p30)

<400> SEQUENCE: 13

Met Glu Thr Asp Thr Leu Leu Leu Trp Val Leu Leu Leu Trp Val Pro
1               5                   10                  15
Gly Ser Thr Gly Asp Ala Pro Val Gly Gly Ser Lys Gly Glu Glu Leu
                20                  25                  30
Phe Thr Gly Val Val Pro Ile Leu Val Glu Leu Asp Gly Asp Val Asn
                35                  40                  45
Gly His Lys Phe Ser Val Arg Gly Glu Gly Glu Gly Asp Ala Thr Ile
                50                  55                  60
Gly Lys Leu Thr Leu Lys Phe Ile Cys Thr Thr Gly Lys Leu Pro Val
65                  70                  75                  80
Pro Trp Pro Thr Leu Val Thr Thr Leu Thr Tyr Gly Val Gln Cys Phe
                85                  90                  95
Ala Arg Tyr Pro Asp His Met Lys Arg His Asp Phe Phe Lys Ser Ala
                100                 105                 110
Met Pro Glu Gly Tyr Val Gln Glu Arg Thr Ile Ser Phe Lys Asp Asp
                115                 120                 125
Gly Lys Tyr Lys Thr Arg Ala Val Val Lys Phe Glu Gly Asp Thr Leu
                130                 135                 140
Val Asn Arg Ile Glu Leu Lys Gly Thr Asp Phe Lys Glu Asp Gly Asn
145                 150                 155                 160
Ile Leu Gly His Lys Leu Glu Tyr Asn Phe Asn Ser His Asn Val Tyr
                165                 170                 175
```

```
Ile Thr Ala Asp Lys Gln Lys Asn Gly Ile Lys Ala Asn Phe Thr Val
            180                 185                 190

Arg His Asn Val Glu Asp Gly Ser Val Gln Leu Ala Asp His Tyr Gln
        195                 200                 205

Gln Asn Thr Pro Ile Gly Asp Gly Pro Val Leu Leu Pro Asp Asn His
210                 215                 220

Tyr Leu Ser Tyr Gln Thr Val Leu Ser Lys Asp Pro Asn Glu Lys Thr
225                 230                 235                 240

Gly Gly Ser Gly Gly Ser Gly Gly Ser Arg Ala Pro Thr Lys Pro Pro
                245                 250                 255

Pro Leu Pro Pro Gly Gly Ser Gly Gly Ser Gly Thr Glu Val
            260                 265                 270

Pro Ser Ser Met Thr Thr Glu Ser Thr Ala Thr Ala Met Gln Ser Glu
        275                 280                 285

Met Ser Thr Ser Ile Met Glu Thr Thr Thr Leu Ala Thr Ser Thr
290                 295                 300

Ala Arg Arg Gly Lys Pro Pro Thr Lys Glu Pro Ile Ser Gln Thr Thr
305                 310                 315                 320

Asp Asp Ile Leu Val Ala Ser Ala Glu Cys Pro Ser Asp Asp Glu Asp
                325                 330                 335

Ile Asp Pro Cys Glu Pro Ser Ser Gly Gly Leu Ala Asn Pro Thr Arg
                340                 345                 350

Val Gly Gly Arg Glu Pro Tyr Pro Gly Ser Ala Glu Val Ile Arg Glu
            355                 360                 365

Ser Ser Ser Thr Thr Gly Met Val Val Gly Ile Val Ala Ala Ala Ala
370                 375                 380

Leu Cys Ile Leu Ile Leu Leu Tyr Ala Met Tyr Lys Tyr Arg Asn Arg
385                 390                 395                 400

Asp Glu Gly Ser Tyr His Val Asp Glu Ser Arg Asn Tyr Ile Ser Asn
                405                 410                 415

Ser Ala Gln Ser Asn Gly Ala Val Val Lys Glu Lys Gln Pro Ser Ser
            420                 425                 430

Ala Lys Ser Ala Asn Lys Asn Lys Asn Lys Asp Lys Glu Tyr Tyr
                435                 440                 445

Val

<210> SEQ ID NO 14
<211> LENGTH: 336
<212> TYPE: PRT
<213> ORGANISM: Artificial Sequence
<220> FEATURE:
<223> OTHER INFORMATION: (synthetic) Post-eGRASP

<400> SEQUENCE: 14

Met Glu Thr Asp Thr Leu Leu Leu Trp Val Leu Leu Leu Trp Val Pro
1               5                   10                  15

Gly Ser Thr Gly Asp Ala Pro Val Gly Gly Asn Asp Pro Asn Leu Phe
            20                  25                  30

Val Ala Leu Tyr Asp Phe Val Ala Ser Gly Asp Asn Thr Leu Ser Ile
        35                  40                  45

Thr Lys Gly Glu Lys Leu Arg Val Leu Gly Tyr Asn His Asn Gly Glu
    50                  55                  60

Trp Cys Glu Ala Gln Thr Lys Asn Gly Gln Gly Trp Val Pro Ser Asn
65                  70                  75                  80
```

-continued

```
Tyr Ile Thr Pro Val Asn Ser Thr Gly Gly Ser Gly Gly Gly Ser
                85                  90              95

Gly Arg Asp His Met Val Leu His Glu Tyr Val Asn Ala Ala Gly Ile
            100             105                 110

Thr Gly Gly Gly Ser Gly Gly Gly Ser Gly Thr Leu Glu Leu Val Pro
            115             120             125

His Leu His Asn Leu Asn Asp Ile Ser Gln Tyr Thr Ser Thr Thr Thr
        130             135             140

Lys Val Pro Ser Thr Asp Ile Thr Leu Arg Pro Thr Arg Lys Asn Ser
145             150             155                         160

Thr Pro Val Thr Ser Ala Phe Pro Thr Ala Lys Gln Asp Asp Pro Lys
            165             170                     175

Gln Gln Pro Ser Pro Phe Ser Val Asp Gln Arg Asp Tyr Ser Thr Glu
            180             185             190

Leu Ser Val Thr Ile Ala Val Gly Ala Ser Leu Leu Phe Leu Asn Ile
            195             200             205

Leu Ala Phe Ala Ala Leu Tyr Tyr Lys Lys Asp Lys Arg Arg His Asp
        210             215             220

Val His Arg Arg Cys Ser Pro Gln Arg Thr Thr Thr Asn Asp Leu Thr
225             230             235                         240

His Ala Pro Glu Glu Glu Ile Met Ser Leu Gln Met Lys His Thr Asp
            245             250             255

Leu Asp His Glu Cys Glu Ser Ile His Pro His Glu Val Val Leu Arg
            260             265             270

Thr Ala Cys Pro Pro Asp Tyr Thr Leu Ala Met Arg Arg Ser Pro Asp
        275             280             285

Asp Ile Pro Leu Met Thr Pro Asn Thr Ile Thr Met Ile Pro Asn Thr
        290             295             300

Ile Pro Gly Ile Gln Pro Leu His Thr Phe Asn Thr Phe Thr Gly Gly
305             310             315                         320

Gln Asn Asn Thr Leu Pro His Pro His Pro His Pro His Ser His Ser
                325             330             335
```